(12) United States Patent
Song et al.

(10) Patent No.: US 9,598,735 B2
(45) Date of Patent: Mar. 21, 2017

(54) DETECTION OF A PANEL OF URINE DNA MARKERS FOR HCC SCREENING AND DISEASE MANAGEMENT

(71) Applicant: JBS Science Inc., Doylestown, PA (US)

(72) Inventors: Wei Song, Audubon, PA (US); Batbold Boldbaatar, Coatesville, PA (US); Lijia Xie, Lansdale, PA (US); Sitong Chen, Audubon, PA (US)

(73) Assignee: JBS Science Inc., Doylestown ( * ) Notice: Subject to any disclaimer, the term of this patent is extended or adjusted under 35 U.S.C. 154(b) by 0 days.

(21) Appl. No.: 14/079,649

(22) Filed: Nov. 14, 2013

(65) Prior Publication Data

US 2014/0155279 A1  Jun. 5, 2014

Related U.S. Application Data

(60) Provisional application No. 61/726,052, filed on Nov. 14, 2012, provisional application No. 61/726,056, filed on Nov. 14, 2012, provisional application No. 61/732,531, filed on Dec. 3, 2012.

(51) Int. Cl.
*C12Q 1/68* (2006.01)

(52) U.S. Cl.
CPC ..... *C12Q 1/6886* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2006/0246433 A1* | 11/2006 | Adorjan et al. | 435/6 |
| 2008/0081338 A1* | 4/2008 | Lo et al. | 435/6 |
| 2009/0197250 A1* | 8/2009 | Cottrell et al. | 435/6 |
| 2010/0221723 A1* | 9/2010 | Santella et al. | 435/6 |
| 2011/0207129 A1* | 8/2011 | Su et al. | 435/6.11 |
| 2013/0130244 A1* | 5/2013 | Su et al. | 435/6.11 |

FOREIGN PATENT DOCUMENTS

WO    WO2006071466    *  7/2006

OTHER PUBLICATIONS

Jain et al.PloS one 7.4 (2012): e35789: 11 pages and supplemental materials.*
Lin et al. The Journal of Molecular Diagnostics 13.5 (2011): 474-484.*
Lowe et al. Nucleic Acids Research, vol. 18, No. 7, p. 1757-1761,1990.*
Iizuka et al. (Clinica Chimica Acta 412 (2011) 152-158).*
Burbee et al.(Journal of the National Cancer Institute 93.9 (2001): 691-699.).*
Zhang et al.( Cancer Letters 221 (2005) 135-143).*
Yan et al. (Cancer Research, 63, 6178-6189).*

* cited by examiner

*Primary Examiner* — Juliet Switzer
(74) *Attorney, Agent, or Firm* — Syncoda, LLC; Junjie Feng

(57) ABSTRACT

Provided herein is a method for detecting the presence or absence of a cancer in a biological sample of an individual, by determining the level of mutation and methylation of one or more genes from a group of genes comprising TP53, CTNNB1, hTERT, RASSF1A, GSTP1, p16, p15 and SFRP-1. Also provided herein is an assay to detect p53 mutations suitable for DNA isolated from biological body fluid in order to screen cancer patients.
Also provided is a method for detecting the presence or absence of a liver cancer in an individual by determining the level of methylation.
Also provided is a suitable method for detecting the presence or absence of a liver cancer in an individual by determining the level of methylation of the promoter of the GSTP1 gene in body fluid such as urine or blood.
Also provided is a suitable method for detecting the presence or absence of a liver cancer in an individual by determining the level of methylation of the promoter of the RASSF1A gene in body fluid such as urine or blood.

7 Claims, 18 Drawing Sheets

FIGURE 1
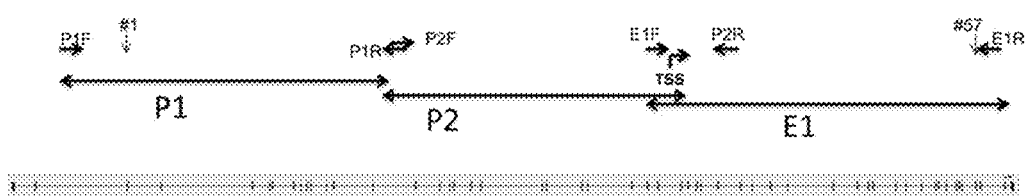
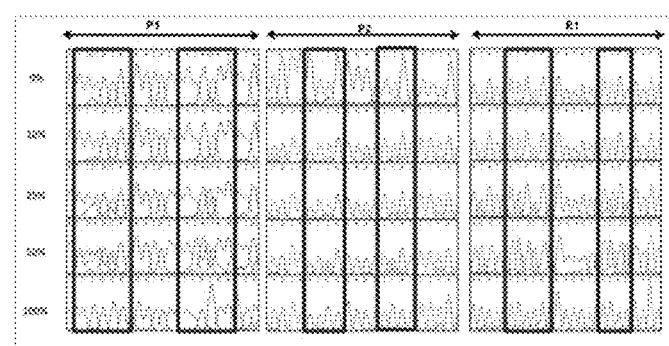

| > or = 50% meth | P1 | P2 | E1 |
|---|---|---|---|
| Hepatitis | 14 (25.5) | 62 (77.5) | 84 (57.9) |
| Cirrhosis | 13 (23.6) | 54 (67.5) | 56 (38.6) |
| Adj non-HCC | 34 (61.8) | 70 (87.5) | 105 (72.4) |
| HCC | 47 (85.5) | 79 (98.8) | 140 (96.6) |

FIGURE 3
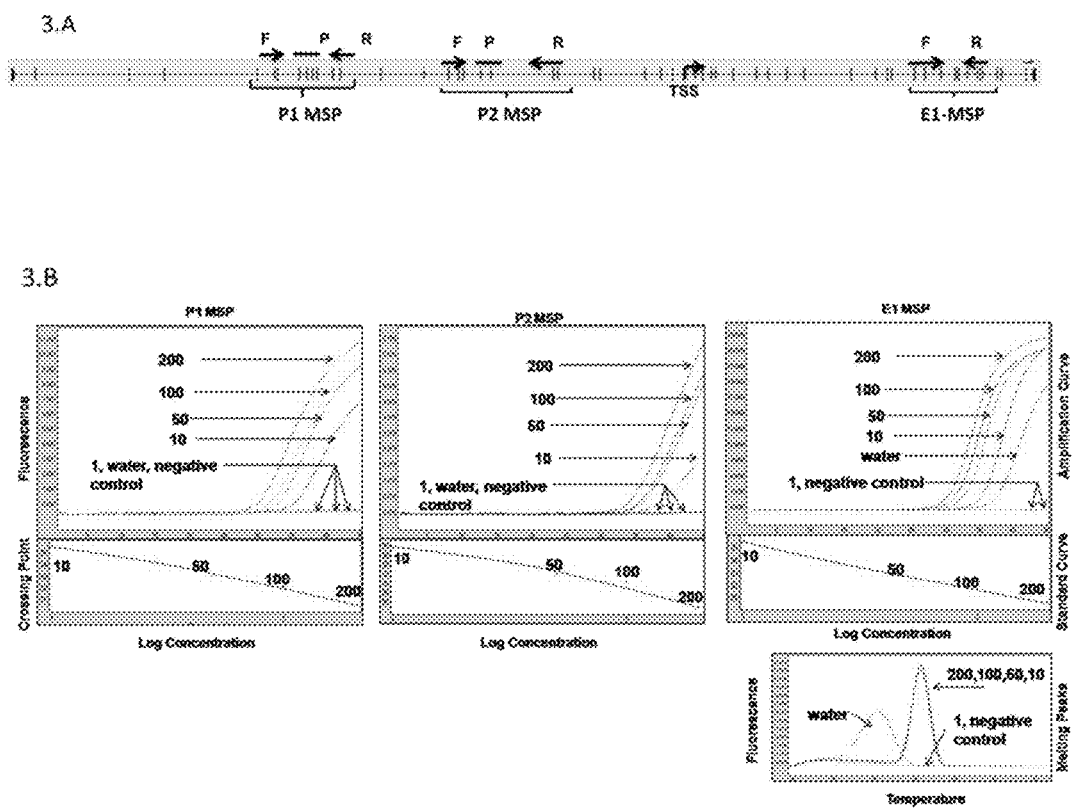
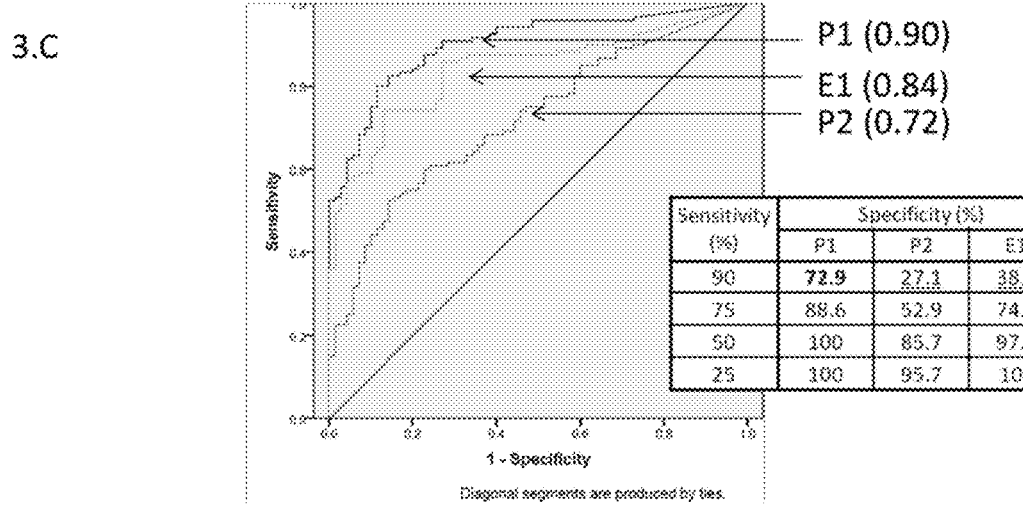

FIGURE 5
5.A
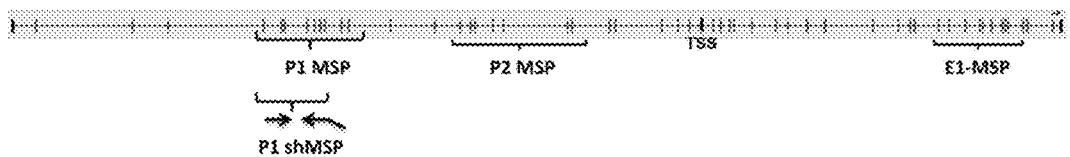
5.B
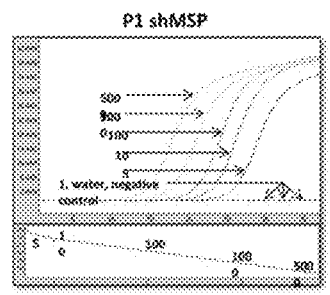
5.C
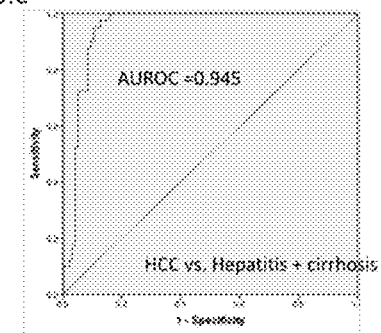

FIGURE 10A

Sequence of GenBank accession # M24485

```
   1 aacaagagat caatatctag aataaatgga gatctgcaaa tcaacagaaa gtaggcagca
  61 aagccaaaga aaatagccta aggcacagcc actaaaagga acgtgatcat gtcctttgca
 121 gggacatggg tggagctgga agccgttagc ctcagcaaac tcacacagga acagaaaacc
 181 agcgagaccg catggtctca cttataagtg ggagctgaac aatgagaaca catggtcaca
 241 tggcggcgat caacacacac tggtgcctgt tgagcggggt gctggggagg gagagtacca
 301 ggaagaatag ctaagggata ctgggcttaa tacctgggtg atgggatgat ctgtacagca
 361 aaccatcatg gcgcacacac ctatgtaaca aacctgcaca tcctgcacat gtaccccaga
 421 acttcaaata aaagttggac ggccaggcgt ggtggctcac gcctgtaatc ccagcacttt
 481 gggaagccga ggcgtgcaga tcacctaagg tcaggagttc gagaccagcc cggccaacat
 541 ggtgaaaccc cgtctctact aaaaatacaa aaatcagcca gatgtggcac gcacctataa
 601 ttccacctac tcgggaggct gaagcagaat tgcttgaacc cgagaggcgg aggttgcagt
 661 gagccgccga gatcgcgcca ctgcactcca gcctgggcca cagcgtgaga ctacgtcata
 721 aaataaaata aaataacaca aaataaaata aaataaaata aaataaaata aaataataaa
 781 ataaaataaa ataaaataaa ataaaataaa ataaagcaat ttccttttcct ctaagcggcc
 841 tccaccccctc tcccctgccc tgtgaagcgg gtgtgcaagc tccgggatcg cagcggtctt
 901 agggaatttc ccccgcgat gtcccggcgc gccagttcgc tgcgcacact tcgctgcggt
 961 cctcttcctg ctgtctgttt actccctagg ccccgctggg gacctgggaa agagggaaag
1021 gcttccccgg ccagctgcgc ggcgactccg gggactccag ggcgcccctc tgcggccgac
1081 gcccggggtg cagcggccgc cggggctggg gccggcggga gtccgcggga ccctccagaa
1141 gagcggccgg cgccgtgact cagcactggg gcggagcggg gcgggaccac ccttataagg
1201 ctcggaggcc gcgaggcctt cgctggagtt cgccgccgc agtcttcgcc accagtgagt
1261 acgcgcggcc cgctccccgg ggatggggct cagagctccc agcatggggc caacccgcag
1321 catcaggccc gggctcccgg cagggctcct cgcccacctc gagacccggg acggggcct
1381 aggggaccca ggacgtcccc agtgccgtta gcggctttca ggggggcccgg agcgcctcgg
1441 ggagggatgg gacccggggg gcggggaggg ggggcaggct gcgctcaccg cgccttggca
1501 tcctccccccg ggctccagca aactttttctt tgttcgctgc agtgccgccc tacaccgtgg
1561 tctatttccc agttcgaggt aggagcatgt gtctggcagg gaagggaggc aggggctggg
1621 gctgcagccc acagcccctc gcccacccgg agagatccga acccccttat ccctccgtcg
1681 tgtggcttt accccgggcc tccttcctgt tccccgcctc tcccgccatg cctgctcccc
1741 gccccagtgt tgtgtgaaat cttcggagga acctgtttac ctgttccctc cctgcactcc
1801 tgaccccctcc ccgggttgct gcgaggcgga gtcggcccgg tccccacatc tcgtacttct
1861 ccctcccccgc aggccgctgc gcggccctgc gcatgctgct ggcagatcag gccagagct
1921 ggaaggagga ggtggtgacc gtggagacgt ggcaggaggg ctcactcaaa gcctcctgcg
1981 taagtgacca tgcccgggca aggggagggg gtgctgggcc ttaggggct gtgactagga
2041 tcggggacg cccaagctca gtgcccctcc ctgagccatg cctcccccaa cagctatacg
2101 ggcagctccc caagttccag gacggagacc tcaccctgta ccagtccaat accatcctgc
2161 gtcacctggg ccgcacccett ggtgagtctt gaacctccaa gtccaggggca ggcatgggca
2221 agcctctgcc cccggagccc tttttgtttaa atcagctgcc ccgcagccct ctggagtgga
2281 ggaaactgag acccactgag gttacgtagt ttgcccaagg tcaagcctgg gtgcctgcaa
2341 tccttgccct gtgccaggct gcctccccagg tgtcaggtga gctctgagca cctgctgtgt
2401 ggcagtctct catccttcca cgcacatcct cttcccctcc tcccaggctg ggctcacag
2461 acagccccct ggttggccca tccccagtga ctgtgtgttg atcaggcgcc cagtcacgcg
```

FIGURE 10B

```
2521 gcctgctccc ctccacccaa ccccagggct ctatgggaag gaccagcagg aggcagccct
2581 ggtggacatg gtgaatgacg gcgtggagga cctccgctgc aaatacatct ccctcatcta
2641 caccaactat gtgagcatct gcaccagggt tgggcactgg gggctgaaca aagaaagggg
2701 cttcttgtgc cctcaccccc cttacccctc aggtggcttg ggctgacccc ttcttgggtc
2761 agggtgcagg ggctgggtca gctctgggcc aggggcccag gggcctggga caagacacaa
2821 cctgcaccct tattgcctgg gacatcaacc agccaagtaa cgggtcatgg gggcgagtgc
2881 aaggacagag acctccagca actggtggtt tctgatctcc tggggtggcg agggcttcct
2941 ggagtagcca gaggtggagg aggatttgtc gccagtttct ggatggaggt gctggcactt
3001 ttagctgagg aaaatatgca gacacagagc acatttgggg acctgggacc agttcagcag
3061 aggcagcgtg tgtgcgcgtg cgtgtgcgtg tgtgtgcgtg tgtgtgtgta cgcttgcatt
3121 tgtgtcgggt gggtaaggag atagagatgg gcgggcagta ggcccaggtc ccgaaggcct
3181 tgaacccact ggtttggagt ctcctaaggg caatgggggc cattgagaag tctgaacagg
3241 gctgtgtctg aatgtgaggt ctagaaggat cctccagaga agccagctct aaagcttttg
3301 caatcatctg gtgagagaac ccagcaagga tggacaggca gaatggaata gagatgagtt
3361 ggcagctgaa gtggacagga tttggtacta gcctggttgt ggggagcaag cagaggagaa
3421 tctgggactc tggtgtctgg cctggggcag acggggtgt ctcagggct gggagggatg
3481 agagtaggat gatacatggt ggtgtctggc aggaggcggg caaggatgac tatgtgaagg
3541 cactgcccgg gcaactgaag ccttttgaga ccctgctgtc ccagaaccag ggaggcaaga
3601 ccttcattgt gggagaccag gtgagcatct ggccccatgc tgttccttcc tcgccaccct
3661 ctgcttccag atggacacag gtgtgagcca tttgtttagc aaagcagagc agacctaggg
3721 gatgggctta ggcctctgc ccccaattcc tccagcctgc tcccgctggc tgagtcccta
3781 gcccccctgc cctgcagatc tccttcgctg actacaacct gctggacttg ctgctgatcc
3841 atgaggtcct agccctggc tgcctggatg cgttcccct gctctcagca tatgtggggc
3901 gcctcagtgc ccggcccaag ctcaaggcct tcctggcctc cctgagtac gtgaacctcc
3961 ccatcaatgg caacgggaaa cagtgagggt tggggggact ctgagcggga ggcagagttt
4021 gccttccttt ctccaggacc aataaaattt ctaagagagc tactatgagc actgtgtttc
4081 ctgggacggg gcttaggggt tctcagcctc gaggtcggtg ggagggcaga gcagaggact
4141 agaaaacagc tcctccagca cagtcagtgg cttcctggag ccctcagcct ggctgtgttt
4201 actgaacctc acaaactaga agaggaagaa aaaaaagag agagagaaac aaagagaaat
4261 a
```

P53 249T quantitative assays

DETECTION OF A PANEL OF URINE DNA MARKERS FOR HCC SCREENING AND DISEASE MANAGEMENT

RELATED APPLICATIONS INFORMATION

The present application claims priority to U.S. Application Ser. Nos. 61/726,052, 61/726,056 and 61/732,531, which were filed on Nov. 14, 2013, Nov. 14, 2013 and Dec. 3, respectively. The disclosures of these three applications are hereby incorporated by reference in their entirety.

GOVERNMENT FUNDING

This work was funded in part by the grants from the National Cancer Institute (R43 CA165312 and 2R44CA165312-02).

SEQUENCE LISTING

The instant application contains a Sequence Listing which has been submitted in ASCII format via EFS-Web and is hereby incorporated by reference in its entirety. Said ASCII copy, created on Feb. 3, 2014, is named JBS0527720005.txt, and is 5,269 bytes in size.

TECHNICAL FIELD

The invention relates to biotechnology, particularly molecular biology and early molecular cancer detection and disease management, including detecting and quantitatively measuring mutations and methylation in nucleic acid sequences associated with cancer using samples from tissue and biological fluid.

BACKGROUND

Hepatocellular carcinoma (HCC) is an aggressive malignancy that has a survival rate of 14% [1]. HCC is the fifth most common cancer in the world, and is the third leading cause of cancer mortality, responsible for between 250,000 and 800,000 deaths per year. Most HCC patients are diagnosed at a late stage using conventional methods of detection, with a survival rate less than 5% after the diagnosis and subsequent treatment. The prognosis is much better if HCC patients are diagnosed at an early stage and treated with surgical and chemotherapeutic intervention. Unfortunately, the early stage of liver cancer is mostly asymptomatic, making the early detection of liver cancer a challenge.

Current methods in detecting HCC include monitoring high risk groups—such as those infected with HBV or HCV—with regular (usually annual or biannual) physical examinations, serum liver function tests (LFTs), ultrasound and other imaging studies. These methods all have their shortcomings. For example, ultrasound imaging is not sensitive for detecting small liver lesions. Other imaging methods, such as CT scan and MRI scan, are very expensive and submit patients to radiation exposure, prohibiting routine use of such methods.

In addition to imaging techniques, elevated serum concentrations of alpha-fetoprotein (AFP) is a useful surrogate marker for HCC, because at least 60% of HCC patients have elevated AFP level at the time of diagnosis. However, elevated level of AFP is influenced by and can result from a number of non-malignant conditions. It is nearly impossible to detect HCC sufficiently early using current methods.

Thus, there is a clear and urgent need for non-invasive, sensitive, reliable methods for the early detection of HCC.

SUMMARY

The present application relates to a method of detecting the presence or absence of a cancer in a biological sample of a subject in need thereof, comprising:
(i) preparing DNA from the biological sample;
(ii) determining the level of mutation or methylation of one or more genes from a group of genes comprising TP53, CTNNB1, hTERT, RASSF1A, GSTP1, p16, p15 and SFRP-1 from the biological sample of the subject;
(iii) comparing the level of mutation or methylation of the one or more genes with the level of mutation or methylation of the one or more genes in one or more control samples from subjects known not to have said cancer; and
(iv) detecting the presence or absence of the cancer, with elevated mutation or methylation levels in the one or more genes of the individual as compared to the level of mutation or methylation in the one or more genes in the one or more control samples indicating the presence of the cancer, and the absence of elevated mutation or methylation levels indicating the absence of the cancer. The method claim of 1, wherein the biological sample comprises tissue or body fluid selected from the group consisting of serum, plasma, and urine.

In one embodiment, the cancer is hepatocellular carcinoma (HCC) and the biological sample is tissue, serum, plasma, or urine.

In another embodiment, the level of mutation is the level of TP53 249T mutation.

In another embodiment, the levels of methylation is the levels of methylation of RASSF1A or GSTP1.

In another embodiment, the level of methylation is the level of methylation of the regulatory region of the RASSF1A gene or GSTP1 gene.

In another embodiment, the regulatory region is the promoter and the first exon of the RASSF1A gene or GSTP1 gene.

In another embodiment, the regulatory region is the promoter and the first exon of the RASSF1A gene, and the regulatory region is selected from the groups consisting of: (i) P1 region of the promoter of the RASSF1A gene; (ii) P2 region of the promoter of the RASSF1A gene and (iii) E1 region of the first exon of the RASSF1A gene.

In another embodiment, the level of methylation is determined by methylation specific PCR (MSP) assays or a two-step short-amplicon methylation specific PCR (shMSP).

In another embodiment, the regulatory region is P1 region and the methylation specific PCR (MSP) for the P1 region uses primers of the nucleotide sequences as set forth in SEQ ID NO:7 and SEQ ID NO:8 and is probed by a probe of the nucleotide sequence as set forth in SEQ ID NO:9.

In another embodiment, the regulatory region is P1 region and the two-step short-amplicon methylation specific PCR (shMSP) for the P1 region uses primers of the nucleotide sequences as set forth in SEQ ID NO:15 and SEQ ID NO:16 for the first step PCR and SEQ ID NO:17 and SEQ ID NO:18 for the second step PCR.

In another embodiment, the selected regulatory region is P2 region and the methylation specific PCR (MSP) for the P2 region uses primers of the nucleotide sequences as set forth in SEQ ID NO:10 and SEQ ID NO:11 and is probed by a probe of the nucleotide sequence as set forth in SEQ ID NO:12.

In another embodiment, the level of methylation of the P1, P2, and E1 regions is determined by bisulfite specific PCR (BSP) and sequencing.

In another embodiment, the bisulfite specific PCR (BSP) uses primers of the nucleotide sequences as set forth in SEQ ID NO: 1 and SEQ ID NO:2 for P1, in SEQ ID NO: 3 and SEQ ID NO:4 for P2, and in SEQ ID NO:5 and SEQ ID NO:6 for E1.

In another embodiment, in step (ii) the level of the mutation is the level of mutation in the coding region of TP53, or the coding region of CTNNB1, or the promoter region of the hTERT, or a combination thereof.

In another embodiment, in step (ii) the level of methylation is the level of methylation in the promoter and first exon regions of the one or more genes.

In another embodiment, the level of mutation is the level of mutation of TP53 gene, the biological sample is urine, and the level of mutation is deemed elevated when the copies of mutated TP53 is greater than 50 copies per milliliter of urine.

In another embodiment, the level of methylation is the level of methylation of mRASSF1A gene, the biological sample is urine, and the level of methylation is deemed elevated when the copies of methylated mRASSF1A is greater than 50 copies per milliliter of urine.

In another embodiment, the level of methylation is the level of methylation of mGSTP1 gene, the biological sample is urine, and the level of methylation is deemed elevated when the copies of methylated mGSTP1 is greater than 1,000 copies per milliliter of urine.

In another embodiment, the biological sample is urine, and the level of mutation is the level of mutation of TP53 and the levels of methylation are the levels of methylations of RASSF1A and GSTP1.

In another embodiment, the subject's probability of having HCC is determined by logistic regression modeling based on three predictor variables: (1) the number of copies of mutated TP53 per milliliter of urine; (2) the number of copies of methylated RASSF1A per milliliter of urine; and (3) the number of copies of methylated mGSTP1 per milliliter of urine, wherein the categorical dependent variable of the logistic regression model is whether the subject has HCC.

In another embodiment, the subject's probability of having HCC is calculated by taking the logistic regression of the three predictor variables and a fourth predictor variable, wherein the fourth variable is 1 when the concentrations of alpha-fetoprotein (AFP) in urine is above 20 ng/ml, and the fourth variable is 0 when the AFP concentration is below 20 ng/ml.

In one embodiment, the level of methylation is the methylation level of CpG sites in a selected regulatory region of the one or more gene.

In another embodiment, the selected regulatory region is SEQ ID NO: 29 and the level of methylation is determined by two-step short-amplicon methylation specific PCR (shMSP), wherein the shMSP uses primers of the nucleotide sequences as set forth in SEQ ID NO:19 and SEQ ID NO:20 for the first step PCR and in SEQ ID NO:21, SEQ ID NO:22 and SEQ ID NO:23 for the second step PCR reaction.

Another aspect of the present application relates to a method for identifying and quantifying at least one nucleic acid sequence from a biological sample of a subject, comprising: (1) isolating the at least one nucleic acid sequence from the biological sample; (2) contacting one or more LNA clamps with the at least one nucleic acid sequence, wherein the one or more LNA clamps correspond to the wildtype allele of the at least one nucleic acid sequence and thereby prevents amplification of the wildtype sequence but not the non-wildtype sequence; (3) amplifying the at least one nucleic acid sequence; and (4) quantifying the at least one nucleic acid sequence.

In one embodiment, the biological sample comprises tissue or body fluid wherein the tissue or body fluid is selected from the group consisting of serum, plasma, and urine.

In another In another embodiment, the LNA clamp comprises a methylene bridge connecting a 2'-oxygen and 4'-carbon (locked nucleic acid (LNA) clamp) in the wildtype nucleic acid sequence.

In another In another embodiment, the nucleotide sequence is p53 and the biological sample is urine or blood.

In another embodiment, the cancer is selected from the group consisting of hepatocellular carcinoma, colon cancer, breast cancer, lung cancer, prostate cancer, ovarian cancer, bladder cancer, lymphoma and stomach cancer.

In another embodiment, the cancer is hepatocellular carcinoma.

In another embodiment, the mutation is a p53 249T mutation.

Another aspect of the present application relates to a kit for identifying and quantifying a nucleic acid sequence from a biological sample, comprising a LNA (locked nucleic acid) clamp for a wildtype nucleic acid sequence a 5' and a 3' primer for the wildtype nucleic acid sequence, wherein the LNA clamp sequence is modified at a ribose to prevent amplification of the wildtype nucleic acid sequence in a nucleotide amplification reaction assay.

In one embodiment, the nucleic acid sequence is DNA sequence, and the modification of the LNA clamp is a methylene bridge connecting a 2'-oxygen and 4'-carbon (locked nucleic acid (LNA) clamp) in the wildtype nucleic acid sequence.

In another embodiment, the nucleic acid sequence is p53.

In another embodiment, the LNA clamp sequence is SEQ ID NO:27.

In another embodiment, the biological sample is urine or blood of a subject being tested for cancer.

BRIEF DESCRIPTION OF THE DRAWINGS

FIG. 1 shows establishment of a methylation reference index for BS-PCR sequencing of the promoter and first exon region of the RASSF1a gene using a reconstituted standards. (A) Schematic of the RASSF1A promoter region (Genbank accession #DQ444319.1) and position of bisulfite sequencing primers for three regions P1 (nt. 357-548), P2 (nt. 530-736), and E1 (nt. 680-981). Vertical lines represent CpG sites, and the transcription start site (TSS) is also indicated. CpG sites designated as #1 to #57 are indicated with arrows. (B) The representative chromatograms of BS-PCR sequencing of the reconstituted standards: 0% methylated+100% unmethylated DNA (0%); 10% methylated DNA+90% unmethylated DNA (10%); 25% methylated DNA+75% unmethylated DNA (25%); 50% methylated DNA+50% unmethylated DNA (50%); and 100% methylated DNA (100%), for P1, P2 and E1 regions are shown. The boxed areas are the areas of the examples showing the relative "C" and "T" peaks in the chromatogram from each sample of the reconstituted standards by each primer set as indicated. (C) Reference index for P1, P2 and E1 showing percentage of methylation based on the relative peak heights of cytosine and thymine at CpG sites obtained from bisulfite sequencing data.

FIG. 1(A) shows the schematic of the RASSF1A promoter region (Genbank accession #DQ444319.1) and position of bisulfite sequencing primers for three regions P1 (nt. 357-548), P2 (nt. 530-736), and E1 (nt. 680-981). Vertical lines represent CpG sites, and the transcription start site (TSS) is also indicated. CpG sites designated as #1 to #57 are indicated with arrows on the basis of the sense strand 5' to 3' direction.

FIG. 1(B) shows the chromatograms of BS-PCR sequencing data from the reconstituted standards: 0% methylated+ 100% unmethylated DNA (0%); 10% methylated DNA+ 90% unmethylated DNA (10%); 25% methylated DNA+ 75% unmethylated DNA (25%); 50% methylated DNA+ 50% unmethylated DNA (50%); and 100% methylated DNA (100%). The P1, P2, and E1 regions are shown. The boxed areas show relative "C" and "T" peaks in the chromatogram for each sample with each primer set, as indicated.

FIG. 1(C) shows the reference index for P1, P2, and E1 used to analyze the methylation status of each CpG site in the RASSF1A promoter, with percent methylation values assigned based on the relative peak heights of cytosine and thymine in bisulfite sequencing data of reconstituted standards. At each CpG site, four results are possible: (1) only C was detected (C only, black box); (2) the C peak was higher than the T peak (C>T, hatched box); (3) the C peak was equal to or lower than the T peak (C≤T, dotted box); and (4) only T was detected (T only, open box). The darker the square, the heavier the methylation present.

FIG. 2(A) shows the methylation status of each CpG site in the promoter and first exon region of the RASSF1A gene based on BS-PCR DNA sequencing in HCC tissue, matched adjacent non-HCC liver tissue (Adj. Non-HCC), and normal, hepatitic, and cirrhotic liver tissues. The data were analyzed as described in FIG. 1(C). Because of the large amount of T in the DNA template after bisulfite conversion, sequencing results from some CpG sites were not available and are designated as x.

FIG. 2(B) shows the percentages of CpG sites with high (> or = to 50%) methylation in each liver tissue type in each region are represented in FIG. 2(A).

FIG. 3 shows methylation-specific PCR (MSP) assays for P1, P2, and E1 regions of the RASSF1a gene. A. Schematic of the RASSF1A promoter, where vertical lines represent CpG sites. Forward and reverse primers and probes are indicated for the three MSP assays in each of the three regions. The transcription start site is also indicated. B. Various concentrations of Huh7 (positive control) with copy numbers as indicated and Hela (negative control), bisulfite converted DNA, were amplified by the MSP assays as detailed in Materials and Methods. (C) Receiver operating curves (ROC) for the MSP assays of the P1, P2 and E1 regions of the RASSF1A gene.

FIG. 3(A) shows the location of the primers and probes for detecting the methylated RASSF1A gene, where vertical lines represent CpG sites. Forward (F) and reverse (R) primers and TaqMan probes (P) are indicated for the three MSP assays in each of the three regions. The transcription start site is also indicated.

FIG. 3(B) shows various concentrations of bisulfite-converted Huh7 (positive control)—with copy numbers indicated—and HeLa (negative control) amplified by the MSP assays.

FIG. 3(C) shows the comparison of the specificity of the methylated P1, P2, and E1 regions of the RASSF1A gene as a biomarker for distinguishing HCC samples from tissue samples of other liver diseases, as determined by MSP assays. Receiver operating characteristic (ROC) curves of the methylated RASSF1A gene as a marker to discriminate HCC (n=120) from non-HCC liver tissues including hepatitis (n=35) and cirrhosis (n=35) (B), or hepatitis, cirrhosis, and adjacent non-HCC (C), were generated by each MSP assay, respectively, as indicated. The area under the ROC curves were indicated and the specificity and sensitivity determined are shown in the inserted table.

FIG. 5 shows methylation-specific PCR (MSP) assays for P1, P2, and E1 regions of the RASSF1a gene. A. Schematic of the RASSF1A promoter, where vertical lines represent CpG sites. Forward and reverse primers and probes are indicated for the three MSP assays in each of the three regions. The transcription start site is also indicated. B. Various concentrations of Huh7 (positive control) with copy numbers as indicated and Hela (negative control), bisulfite converted DNA, were amplified by the MSP assays as detailed in Materials and Methods. (C) Receiver operating curves (ROC) for the MSP assays of the P1, P2 and E1 regions of the RASSF1A gene.

FIG. 5(A) shows the location of the primers for detecting the methylated RASSF1A gene with a shorter amplicon (P1 shMSP) where vertical lines represent CpG sites. Forward and reverse primers are indicated for the P1 shMSP assays in the P1 region. The transcription start site is also indicated.

FIG. 5(B) shows various concentrations of bisulfite converted Huh7 (positive control)—with copy numbers indicated—and HeLa (negative control) amplified by the P1 shMSP assay.

FIG. 5(C) shows the ROC curve for the methylated P1 region of the RASSF1A gene as a biomarker to distinguish urine of patients with HCC (n=40) from patients with other liver diseases (cirrhosis, n=50; hepatitis, n=44), as determined by P1 shMSP assays. The area under the ROC curve was indicated.

Figure 8:
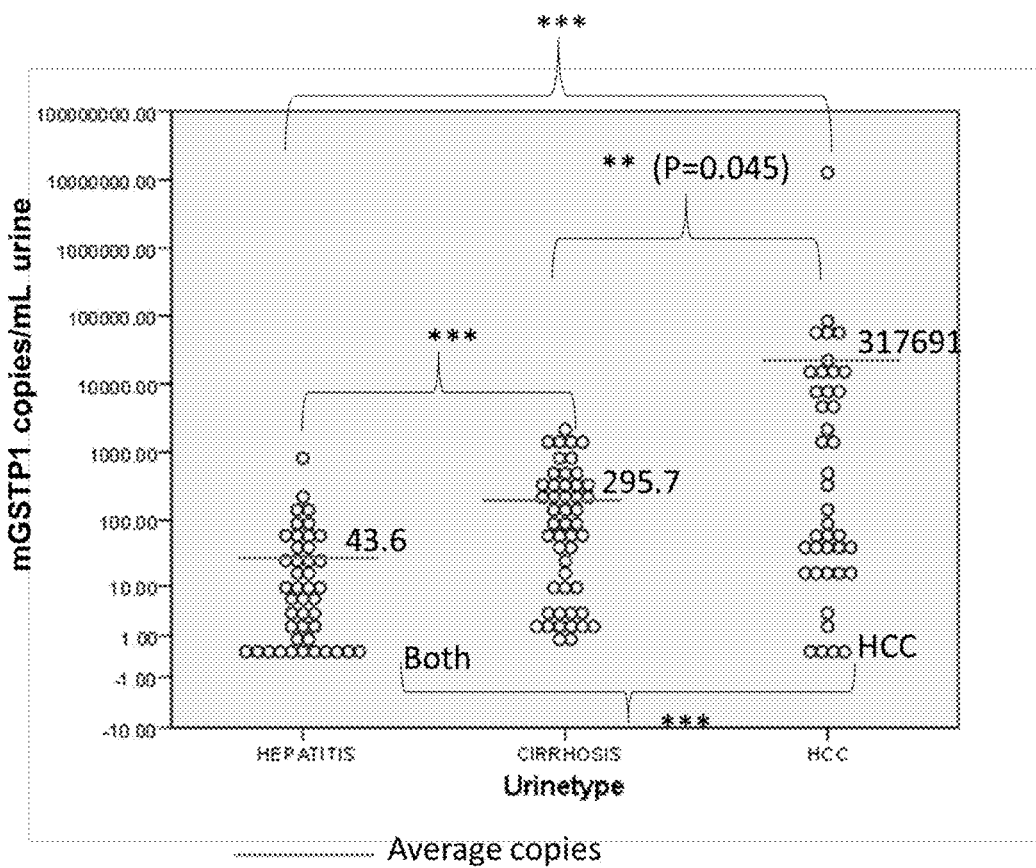

FIG. 8 shows the comparison of the amount of mGSTP1 DNA in urine of patients with HCC (n=44) and other liver diseases including hepatitis (n=58) and cirrhosis (n=35). Each circle represents the data from each patient urine. The quantity of mGSTP1 DNA detected is shown as per mL urine. The average amounts of mGSTP1 in each disease group are indicated. *** indicates that p values is less than 0.001 by a Fisher exact t-test.

Figure 9:
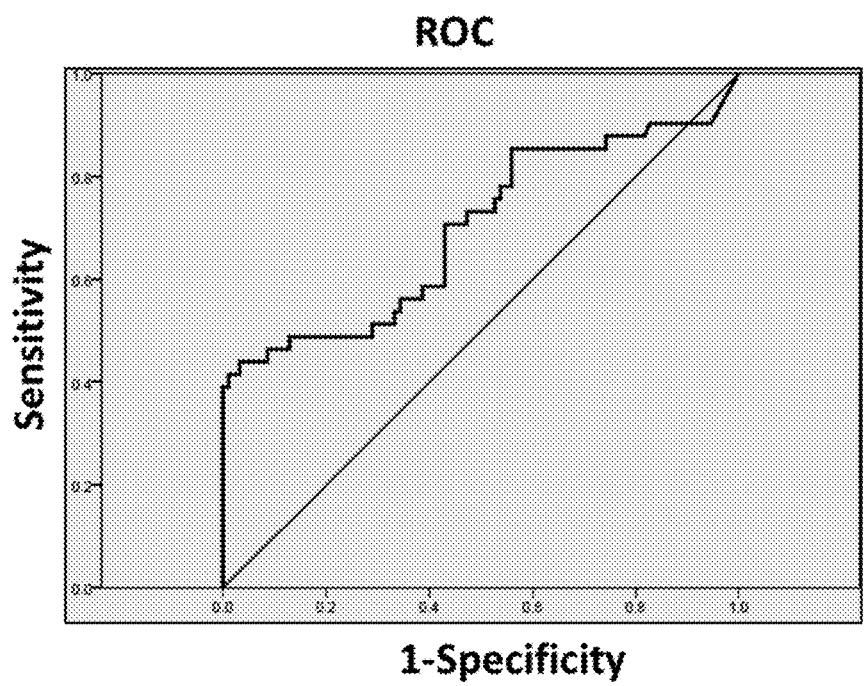

FIG. 9 shows the receiver operating characteristic (ROC) curves of the methylated GSTP1 gene as a urine marker to discriminate patients with HCC (n=44) from patients with non-HCC liver diseases including hepatitis (n=58) and cirrhosis (n=35). The area under the curve of ROC (AUROC) was determined as listed.

FIG. 10 shows the full sequence of GenBank accession #M24485.

Figure 11:
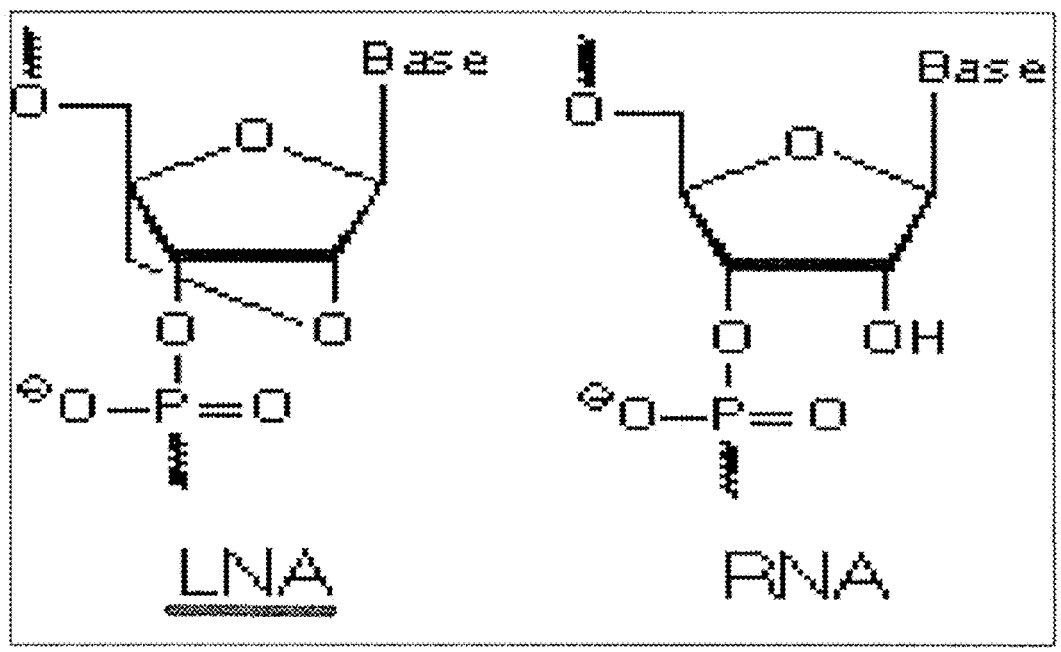

FIG. 11 is a chemical structure drawing illustrating a locked nucleic acid (LNA) and unmodified RNA.

Figure 12:
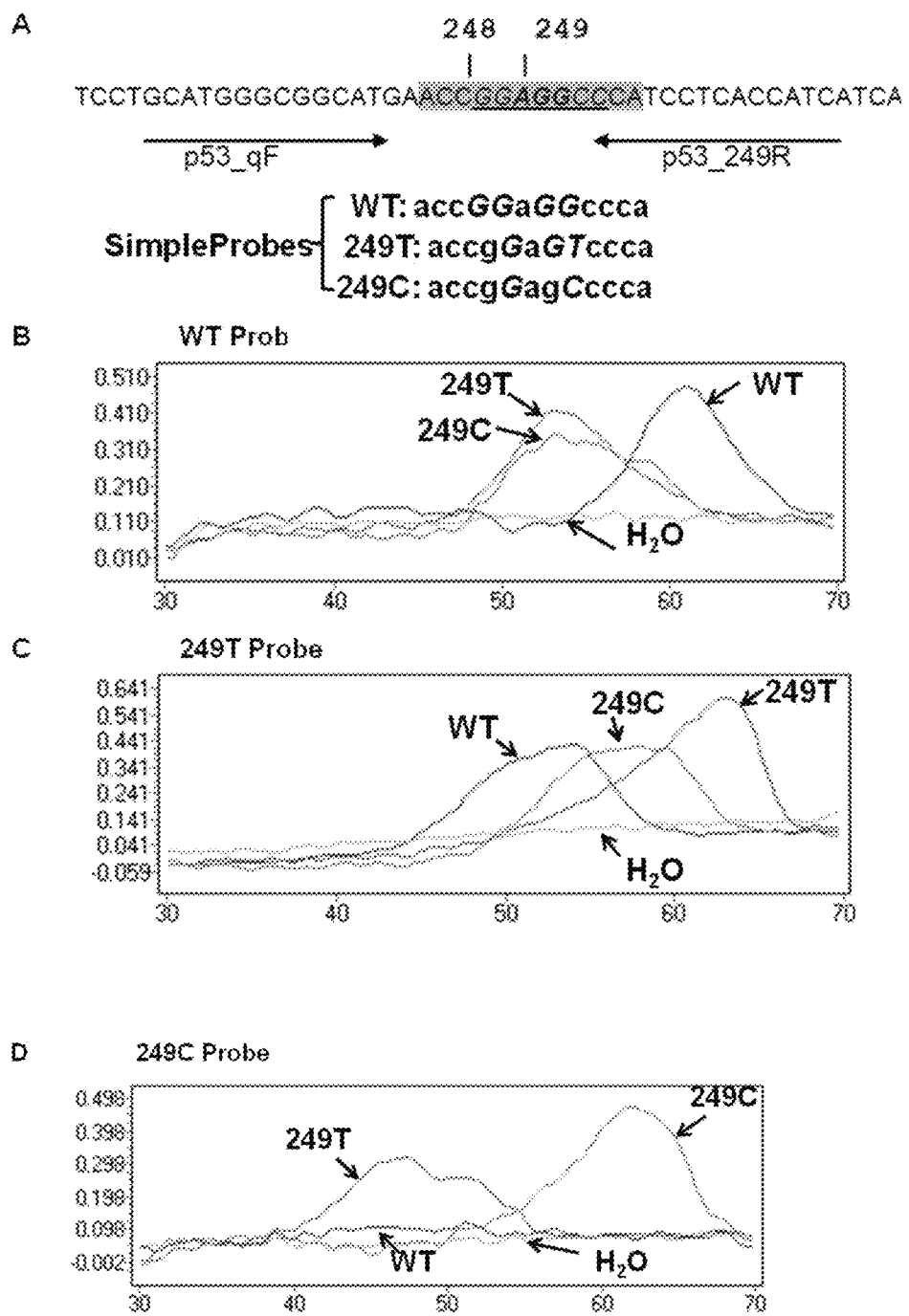
Figure 13:
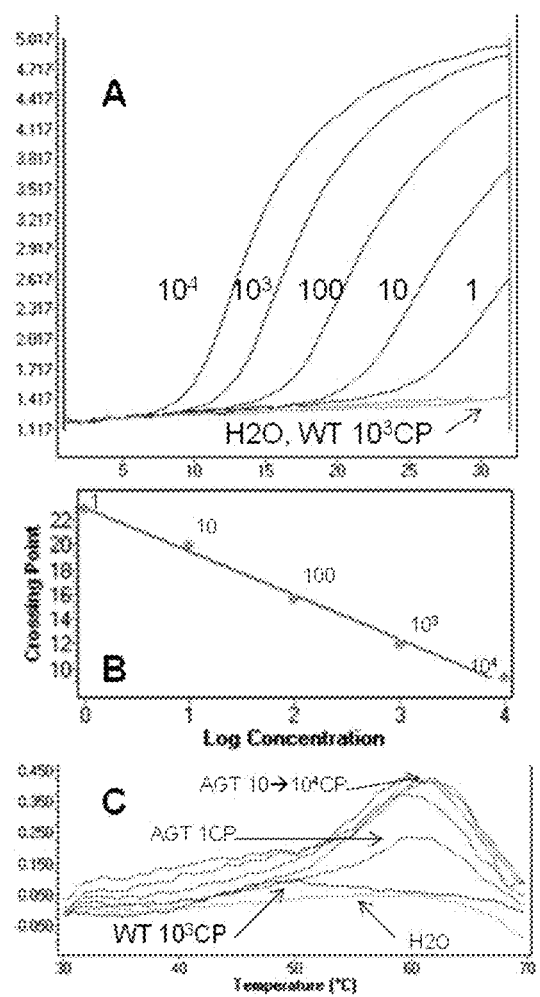

FIG. 12 is an illustration of the template sequences designed to assay for the TP53 249T quantitative mutation modified from a published assay in Lin et al., Journal of Molecular Diagnostics 13: 474-484 (2011), showing detection of p53 codon 249 mutations by an LNA clamp-mediated PCR assay and melting curve analysis with SimpleProbes. A: Locations and sequences of primers (arrows), clamp (underlined), and probes (shaded) used in the assay. Codons 248 and 249 are indicated by vertical lines. LNAs are italicized. SimpleProbe sequences shown with LNA are italicized and capitalized. PCR products derived from plasmids p53 WT (red), p53_249T (blue), p53_249C (green), or water (light blue) were determined by the melting curve analysis, as indicated by the arrows, with the SimpleProbes 249WT (B), 249T (C), and 249C (D). LNA, locked nucleic acid; WT, wild-type. The following sequences are shown: tcctgcatgggcggcatgaaccggaggcccatcctcaccatcatcacactg-gaagactcc; LNA clamp: GGAGGCC; 249T probe: accg-GaGTccca; WT probe: accGGaggccca; 249C probe: accg-GagCccca FIG. 13 are graph results from a TP53 gene real-time PCR Assay quantifying the p53 gene including codon 249. Graph A) Amplification curves; Graph B) Standard curve; Graph C) Melting curves. The assay generated a linear range from 10 to $10^4$ copies.

Figure 14:
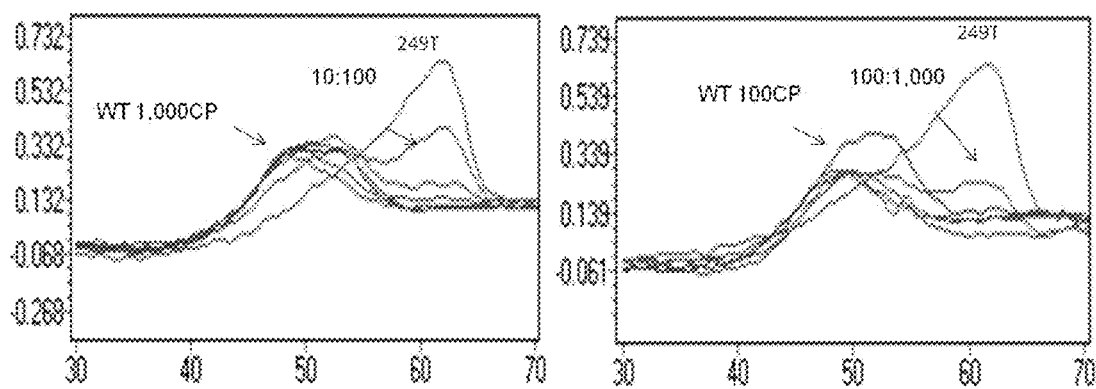

FIG. 14 illustrates the specificity of the TP53 249T mutation assay by using SimpleProbe® Melt Curve analysis with 249T probe. The specificity of TP53 249T mutation assay was determined by reconstitution of 10 CP of plasmid 249T with $10^3$ of WT plasmid in the presence of the WT LNA clamp (green wt; blue 249T 10:100). The LNA suppressed amplification of the WT plasmid up to $10^7$ CP.

Figure 15:
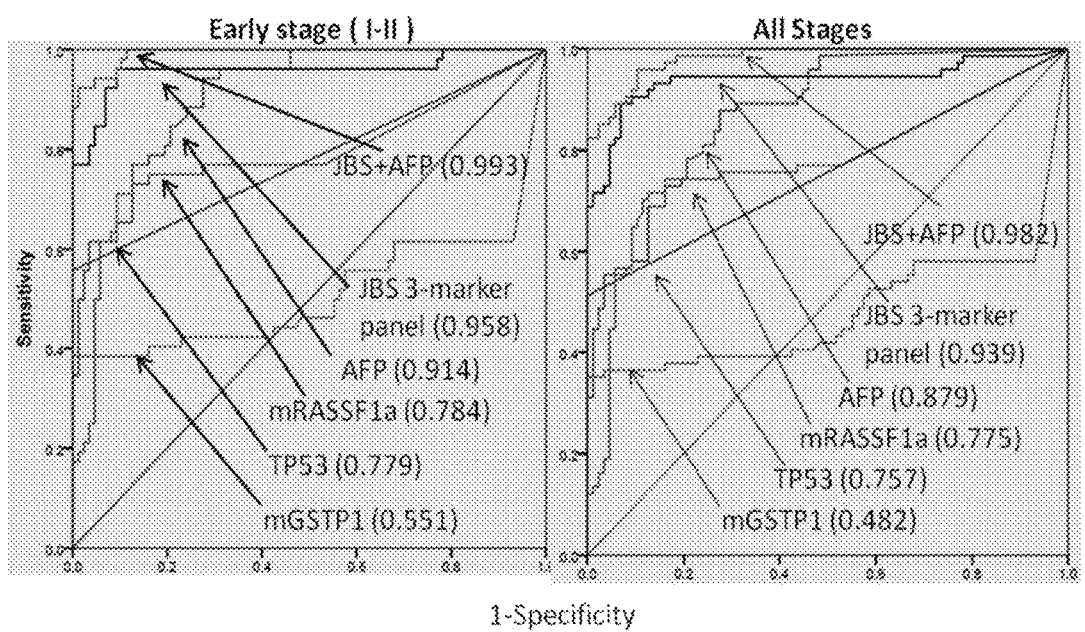

FIG. 15 illustrates the performance of 3-DNA marker panel (i.e., RASSF1a, TP53 and mGSTP1) alone or with AFP to distinguish the early stage (stage I-II, n=52, left panel) HCC or all stages (n=74, right panel) HCC from cirrhosis (n=45) and hepatitis (n=42) in urine. The AUROC of each curve is indicated in parentheses following each marker. In this study cohort, the sensitivity of serum AFP remained limited with 44% for detecting the early stage HCC and 41% for all HCC by using 20 ng/mL as the cutoff as suggested by the American Association of Liver Diseases [3]. This 3-DNA marker panel had an AUROC of 0.958 (95% CI, 0.916-1.000) for detecting early HCC from cirrhosis and hepatitis and an AUROC of 0.939 (95% CI, 0.895-0.983) for detecting all stages HCC. With serum AFP, the AUROC increases to 0.993 (95% CI, 0.984-1.000) for detecting the early stage HCC and 0.982 (95% CI, 0.967-0.996) for detecting all stages HCC. By logistic regression, the sensitivity of this 3-marker urine test alone or with AFP is 77% (33% better than AFP) or 90%, respectively, with specificity of 95%, respectively, for early stage HCC.

Figure 16:
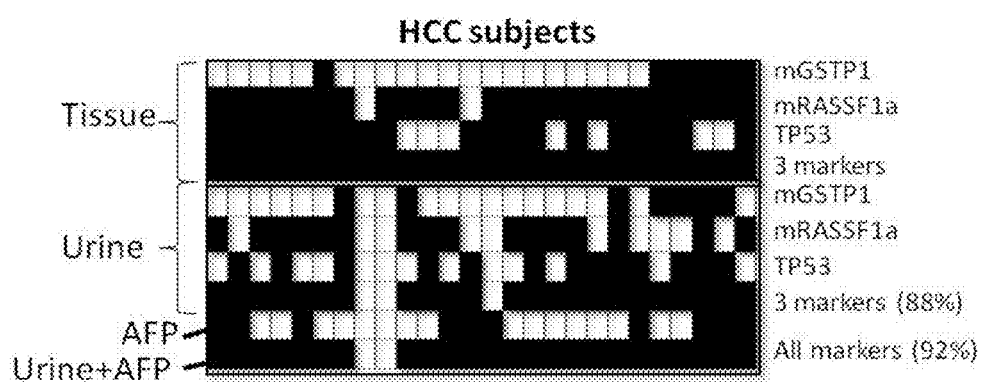

FIG. 16 demonstrates the detection of DNA markers in urine using three short-amplicon assays from patients with marker-positive HCC tissue. The marker distribution of each HCC subject that has marker-positive tissue and with available serum AFP value was plotted. Each box represent data from each individual HCC patient. Filled boxes represent a marker detected or positive for AFP. Empty boxes represent a marker not detected or negative for AFP. There are 26 HCC subjects in this comparison. By defining positive as any one marker positive in urine, The 3 DNA marker HCC urine test, alone detected 88%, almost 90%, and together with AFP, detected 92% of urine samples from marker positive tissue.

Figure 17:
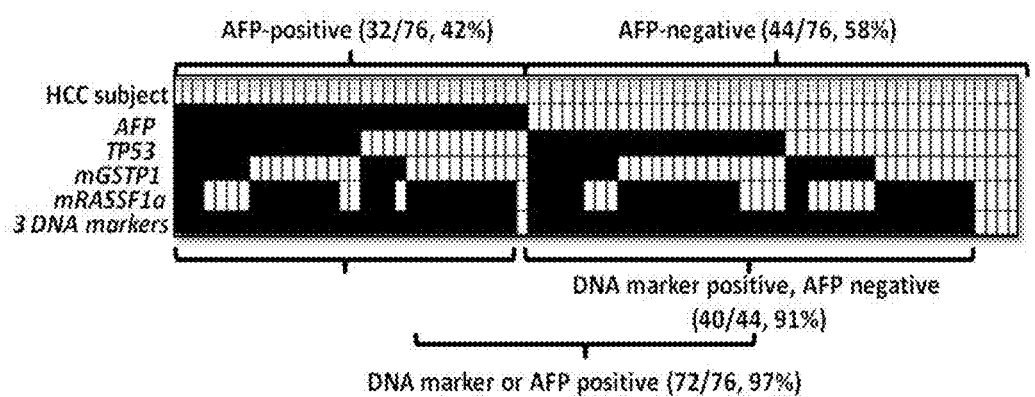

FIG. 17 demonstrates the detection of AFP-negative HCC by the 3-DNA marker (RASSF1a, TP53 and mGSTP1) urine DNA test. Filled boxes represent a marker detected or positive for AFP. Empty boxes represent a marker not detected or negative for AFP. In this study population (n=76), 44 patients (58%, 44/76) with HCC had AFP serum levels less than 20 ng/mL and their HCC samples were therefore considered to be AFP-negative. This 3-DNA marker panel was found in 91% (40/44) of the AFP-negative HCC urine, thus increasing the sensitivity of detecting HCC from 42% (32/76) with AFP alone to 97% (72/76) by combining HCC urine test with serum AFP.

DETAILED DESCRIPTION OF ILLUSTRATIVE EMBODIMENTS

Disclosed herein is a sensitive, specific, and quantitative test for early detection of cancer.

More specifically, the disclosure relates to detecting HCC in a subject by determining the level of mutation and methylation of a panel of genes comprising NA markers for HCC screening. The development of HCC, as with other solid tumors, is believed to require the dysregulation of at least 3 biochemical pathways (proliferation, cell cycle, apoptosis/cell survival) within the cell [4-6]. In addition to genetic mutations, the aberrant methylation of tumor suppressors play important roles throughout the process of HCC carcinogenesis. Thus, the urine DNA test is designed to detect both genetic including TP53_249 mutation [7-12], CTNNB1 mutations [7, 13-20], hTERT mutations, and epigenetic methylated DNA markers including mRASSF1 [21-28], mGSTP-1 [4, 26, 29, 30], and mp16 [4, 29-35], and mp15 [23, 27-30], and mSFRP1 [4, 36-39], to obtain sufficient sensitivity and specificity to screening for HCC.

Mutations in the TP53 gene have been associated with approximately 50% of human cancers. In HCC, a G:C to T:A transversion at the codon 249 (249T) is a known "hotspot". (Hsu et al. *Nature,* 350:377-8, 1991). Current methods of p53 detection such as restriction fragment length polymorphism and PCR-based assays followed by DNA sequencing are insensitive, merely qualitative, time consuming and labor intensive. There remains a need for an assay to quantitatively measure for the mutations and for a test to screen for HCC so that HCC can be detected early and administered early.

De novo somatically acquired DNA methylation occurs predominantly at CpG dinucleotides within the promoter and upstream exons of genes and, in conjunction with histone modification, alters chromatin density and the accessibility of DNA to transcriptional cellular machinery, thereby modulating the expression of the underlying DNA sequence [27, 40].

The GSTP1 gene encodes glutathione S-transferase π, which protects normal hepatocytes against a number of mutation-inducing processes, such as reactive oxygen species linked with chronic hepatic inflammation and reactive electrophilic compounds linked with the hepatic metabolism of dietary and other carcinogens. Hypermethylation of its promoter region has been shown to suppress the expression of the GSTP1 gene [41]. Thus, the hypermethylation of the promoter of the GSTP1 gene has been associated with various cancers, including HCC [42].

We have previously demonstrated that only the 5' region of the 32 CpG sites examined (numbered −28 to +4 relative to the transcription start site) in the promoter region of the GSTP1 gene that are methylated specifically in HCC compared to normal liver and hepatitis and cirrhotic liver tissues. On the other hand, CpG methylation was observed in the 3' region (CpG sites from the −7 to +4) in most of the liver tissues studied including normal liver. We demonstrated that the MSP assay, designed for the 3' region to analyze the mGSTP1 promoter for distinguishing HCC from cirrhosis and hepatitis, would have poor specificity (60%). In contrast, a high specificity (97.1%) was obtained when the MSP assay was designed for the 5' region of the promoter [43].

RASSF1A is a tumor suppressor gene; aberrant DNA methylation of the RASSF1A gene has been shown to occur in >90% of liver cancer [24, 44-46]. The RASSF1A gene is a member of the Ras association domain family of genes (RASSF) which can associate with the Ras family of GTPases to regulate the cell cycle and trigger apoptosis [47]. Though the precise control mechanisms of these genes are still unknown, abnormal signaling in Ras oncogenes can contribute to roughly 70% of all cancer [47] and particularly in >90% of liver cancer [24, 44-46]. Thus, RASSF1A methylation holds great potential as an high sensitive epigenetic marker for HCC.

However, poor measures of specificity of methylated RASSF1a (mRASSF1a) to HCC have existed in these studies. For example, Chan et al. (2008) [44] mRASSF1a detected in 59 of 63 (93%) serum samples of HCC patients, but also in 37 of 63 (58%) HBV carriers; Nishida et al. (2008) [26] found 27.3%-72.7% DNA methylation at 19 loci of the RASSF1a gene in 22 samples of normal liver tissue, though DNA isolated from HCC tissue demonstrated methylation at all CpG loci examined. Lastly, Di Giola et al. (2006) [45] demonstrated wide ranges of methylation percentages in both hepatitic and non-hepatitic liver. In addition to its association with carcinogenesis, methylation of the RASSF1A gene has been also associated with aging [26]. Thus, the specificity of mRASSF1A as a biomarker for distinguishing HCC from other non-HCC liver diseases remains unclear.

Urine has been used as a source of reporter molecules for urinary tract diseases with great clinical benefit. Urine-based tests are non-invasive and very patient-friendly. The use of urine as a biological fluid for cancer detection is now possible with advances in molecular biomarker assays and recent findings that tumor-derived DNA in circulation can be detected in urine as low-molecular-weight (LMW) urine DNA less than 300 bp in size [48]. A high-throughput technology to preferentially isolate this LMW urine DNA species has been developed [49]. It has been shown that compared to using total urine DNA, using LMW urine DNA as the substrate enhanced the sensitivity and specificity of detecting tumor-derived genetic mutations in urine [48, 50-52]. However, it was unknown whether urine DNA or LMW urine DNA could be successfully used to detect epigenetic changes that occurred in liver.

There remains a need for a method to more consistently and accurately determine the hypermethylation state of the RASSF1A promoter, GSTP1 promoter and the mutation level of the TP53 gene for HCC screening, early disease detection, and disease management and whether the methylated DNA derived from HCC can be detected in urine.

The present subject matter may be understood more readily by reference to the following detailed description taken in connection with the accompanying examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "about," it is understood that the particular value forms another embodiment. All ranges are inclusive and combinable.

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The term "nucleic acid" refers to a deoxyribonucleotide (DNA) or ribonucleotide (RNA) and complements thereof. The size of nucleotides is expressed in base pairs "bp". Polynucleotides are single- or double stranded polymers of nucleic acids and complements thereof.

A biological fluid can comprise, for example, whole tissue, such biopsy sample. Other examples of a biological fluid include, but are not limited to, saliva, nasopharyngeal, blood, plasma, serum, gastrointestinal fluid, bile, cerebrospinal fluid, pericardial, vaginal fluid, seminal fluid, prostatic fluid, peritoneal fluid, pleural fluid, urine, synovial fluid, interstitial fluid, intracellular fluid or cytoplasm and lymph. bronchial secretions, mucus, or vitreous or aqueous humor. Biological fluid can also include a culture medium. A particularly useful biological fluid in the present method is urine.

A "locked nucleic acid" LNA is a chemically modified RNA nucleotide whose ribose is modified with a methylene bridge connecting the 2'-oxygen and 4'-carbon.

The term "nucleotide amplification reaction" refers to any suitable procedure that amplifies a specific region of polynucleotides (target) using primers. See generally Kwoh et al., Am. Biotechnol. Lab. 8:14 (1990; Kwoh et al., Proc. Natl. Acad. Sci. USA 86, 1173-1177 (1989); Lizardi et al., BioTechnology 6:1197-1202 (1988); Malek et al., Methods Mol. Biol., 28:253-260 (1994); and Sambrook et al., "Molecular Cloning: A laboratory Manual" (1989)).

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "effective amount," in the context of treatment of a disease or disorder refers to the amount of such molecule that is sufficient to inhibit the occurrence or ameliorate one or more clinical or diagnostic symptoms of the disease or disorder in a subject. The term "effective regime" refers to a combination of amount of the agent being administered and dosage frequency adequate to accomplish treatment or prevention of the disease or disorder.

Due to the imprecision of standard analytical methods, molecular weights and lengths of polymers are understood to be approximate values. When such a value is expressed as "about" X or "approximately" X, the stated value of X will be understood to be accurate to ±10%.

Examples are provided to assist in a further understanding of the inventions. Particular materials used, protocols and conditions are intended to be further illustrative of the inventions and should not be construed to limit the reasonable scope thereof.

Provided herein is a suitable method for detecting the presence or absence of a cancer in an individual by determining the level of mutation and methylation of a panel of genes from the individual, comparing the level of mutation and methylation with a baseline level of mutation and methylation found in one or more control samples from individuals known not to have the cancer, and correlating a finding of elevated mutation or methylation in the individual with an enhanced likelihood that the individual has cancer. The cancer can be hepatocellular carcinoma (HCC) and the control can be non-HCC sample. The tumor associated genes can be TP53, CTNNB1, hTERT, RASSF1A, p16, p15, SFRP1 and GSTP1. The regulatory region can be the promoter of the RASSF1A, GSTP1 p16, p15, SFRP1 genes, the first exon of the RASSF1A, GSTP1 p16, p15, SFRP1 genes, or both. The individual can be a human.

The level of methylation of the P1 region of the RASSF1A DNA can be determined by methylation specific PCR (MSP) targeting a 61 bp amplicon and the MSP can use primers of the nucleotide sequence as set forth in SEQ ID NO:7 and SEQ ID NO:8 and can be probed by a probe of the nucleotide sequence as set forth in of SEQ ID NO:9. The MSP can also be a two-step PCR assay targeting for a shorter amplicon, a 49 bp amplicon, (shMSP), using primers of the nucleotide sequence as set forth in SEQ ID NO: 15, SEQ ID NO:16 for the first step PCR and SEQ ID NO: 17, SEQ ID NO:18 for the second step PCR. The level of methylation of the P1 region of the RASSF1A can also be determined by bisulfite specific PCR (BSP) and sequencing. The BSP can use primers of the nucleotide sequence as set forth in SEQ ID NO: 1 and SEQ ID NO:2.

The level of methylation of the P2 region of the RASSF1A DNA can be determined by methylation specific PCR (MSP) and the MSP can use primers of the nucleotide sequence as set forth in SEQ ID NO: 10 and SEQ ID NO:11 and can be probed by a probe of the nucleotide sequence as set forth in of SEQ ID NO:12. The level of methylation of the P2 region of the RASSF1A can also be determined by bisulfite specific PCR (BSP) and sequencing. The BSP can use primers of the nucleotide sequence as set forth in SEQ ID NO: 3 and SEQ ID NO:4.

The level of methylation of the E1 region of the RASSF1A DNA can be determined by methylation specific PCR (MSP) and the MSP can use primers of the nucleotide sequence as set forth in SEQ ID NO: 13 and SEQ ID NO:14. The level of methylation of the P1 region of the RSSF1a can also be determined by bisulfite specific PCR (BSP) and sequencing. The BSP can use primers of the nucleotide sequence as set forth in SEQ ID NO: 5 and SEQ ID NO:6.

Methylation of the promoter of the tumor suppressor, the RASSF1A gene, has been associated with various malignancies, including hepatocellular carcinoma (HCC). However, its specificity in distinguishing HCC from normal liver tissue is unclear. The extent of DNA methylation of these three region—P1, P2, and E1—on DNA isolated from tissues of all stages of the HCC pathology—normal, hepatitic, cirrhotic, adjacent non-HCC, and HCC—was analyzed by BS-PCR DNA sequencing using the individualized reference index for each primer set (FIG. 1) and by MSP assays. Comparing the data obtained from normal livers, hepatitis, cirrhosis, HCC and matched adjacent non-HCC liver tissue, the P1 region had the highest level of specificity methylation in all three regions, to distinguish HCC from other liver diseases as well as normal liver tissue. By BS-PCR DNA sequencing data, while more than 85% of CpG sites studied in each region were significantly methylated (e.g., >50%) in HCC, the methylation of the P1 region was significantly less in non-cancerous disease liver tissue (hepatitis and cirrhosis), (25.5% and 23.6% for hepatitis and cirrhosis, respectively) compared to E1 and P2 (57.9% and 38.6% for E1, and 77.5% and 67.5% for P2, for hepatitis and cirrhosis, respectively) as compared by Fishers exact test (P<0.001) (FIG. 2B) suggesting that P1 is the most specific region to HCC as compared to P2 and E1 regions.

Using the quantitative real-time MSP PCR assay system, methylation levels for every sample were calculated in duplicate and averaged. These values were then analyzed using SPSS software (IBM) and receiver operating curves (ROC) were constructed for each region. As shown in FIG. 3C, P1 is a statistically better test than both E1 and P2 as its AUROC=0.90 compared to 0.84 for E1 and 0.72 for P2 (P1 vs E1, P=0.0256; P1 vs P2, P<0.0001; E1 vs P2, P=0.0024: StAR: Statistical Comparison of ROC Curves). At 90% sensitivity, the P1 assay had a specificity of 72.9%—almost twice as specific as the E1 assay which was only 38.6% specific and far better than the P2 assay which was a mere 27.1% specific (P<0.0001 by Fisher's exact 2-tailed test). A similar trend was observed at all other fixed values of sensitivity. Thus, we conclude that P1 is the best region in the RASSF1A promoter region for methylation analysis in the context of liver cancer screening. The cutoff mRASSF1A methylation level for detecting HCC can be at 50 copies of methylated mRASSF1A per mL of urine.

The level of methylation of the promoter region of the GSTP1 DNA can be determined by a short amplicon (sh) MSP assay targeting a 42 bp amplicon and the shMSP can use primers of the nucleotide sequence as set forth SEQ ID NO:19 and SEQ ID NO:20 for the first step PCR and in SEQ ID NO:21, SEQ ID NO:22 and SEQ ID NO:23. The cutoff GSTP1 methylation level for detecting HCC can be at 1000 copies of methylated GSTP1 per mL of urine.

Also described herein is a method providing a sensitive, specific, and quantitative assay for detecting mutations in TP53 nucleic acid sequences compared to wildtype TP53 sequences isolated from a biological samples including body fluid. Any tumor-derived DNA isolated from patients can be used in the present method because of selective amplification of mutated DNA sequences but not wildtype sequence in a nucleotide amplification reaction such as PCR. The method uses a seven nucleotide Locked Nucleic Acid (LNA) clamp designed to suppress the amplification of wildtype sequences; amplifying selective TP53 templates that contained any mismatches with the LNA clamp. The PCR product was quantified by probe in the second step PCR and then characterized by melting curve analysis. The running time of the assay is less than 2 hours and can be used as a high throughput format for a blood or urine test for HCC screening. For areas with a low prevalence of the mutation, this screening assay may be combined with other complementary screening tests such as the alpha-fetoprotein blood test and ultrasound imaging. The cutoff TP53 mutation level for detecting HCC can be at 50 copies of mutated TP53 per mL of urine.

Also described herein is a process modification from a published assay by Lin et al., 2011 for not only identifying, but also quantifying the amount of mutated nucleic acid in TP53 codon 248-249 mutations. First, an LNA clamp was used to suppress the amplification of a wildtype DNA template, demonstrating that the sensitivity and specificity of the assay could be enhanced. Second, the amplified region in the DNA template was only 41 basepairs, rendering it suitable for not only DNA isolated from tissue, but also DNA from body fluids. Third, SimpleProbes™ were used to quantify the PCR products by amplification curve (FIGS. 13A & B) and the PCR products are characterized by the melting curve analysis (FIG. 13C). The assay has high sensitivity and specificity. The LNA clamp-mediated PCR assay detects up to a few copies of the mutated sequence with a high specificity ratio of 1:1,000 (0.1%) of mutant to wildtype sequences. The suppression of wildtype template amplification by the LNA clamp is based on the perfect match of the LNA clamp to the wildtype sequences. The base pairing of LNA to DNA exerts higher thermostability than that of DNA to DNA, resulting in a wide range of Tm differences (6-10° C.) between the perfect match and a single base pair mismatch. Based on the Tm difference the inventors optimized the PCR conditions to selectively amplify only the mutated sequence and not the wildtype sequence. The results was almost complete suppression of $10^7$ copies of the wildtype sequence when PCR products were detected by the SimpleProbe™. Furthermore, the assay not only was able to detect the 249T mutation but was able to detect any mutation in the region of the LNA clamp.

In addition to high sensitivity and specificity, the process also achieved surprisingly accurate quantification of the mutated nucleic acid in TP53 codon 248-249 mutations. For at least the three reasons that follow, quantification of the mutated nucleic acid is particularly difficult: (1) it is difficult to determine the cycle numbers for the first round PCR to ensure within-linear-range amplification after two steps of amplification; (2) the cycle numbers for the second round PCR needs to be precise in order to avoid non-specific amplification and to ensure the amplification is within the range of linearity; and (3) SimpleProbe (by Roche) dictates and requires particular primer concentrations. Moreover, primer concentrations for the first round and second round PCR need to be different. Furthermore, forward and reverse primers also require different concentrations.

The performance of a 3-DNA marker panel (i.e., mRASSF1a, TP53 and mGSTP1), alone or with AFP, to distinguish the early stage HCC or all stages HCC from cirrhosis and hepatitis by the short amplicon assays was tested in urine. This 3-DNA marker panel tested in urine had an AUROC of 0.958 (95% CI, 0.916-1.000) for detecting early HCC from cirrhosis and hepatitis and an AUROC of 0.939 (95% CI, 0.895-0.983) for detecting all stages HCC. With serum AFP included in the 3-DNA panel, the AUROC increases to 0.993 (95% CI, 0.984-1.000) for detecting the early stage HCC and 0.982 (95% CI, 0.967-0.996) for detecting all stages HCC. By logistic regression, the sensitivity of the 3-marker urine test alone or with AFP is 77% (33% better than AFP) or 90%, with specificity of 95%, respectively, for early stage HCC. The 3-DNA marker HCC urine test, alone detected 88% of HCC Together with AFP, the 3-DNA marker HCC urine test detected 92% of HCC. In this study population, 44 patients (58%, 44/76) with HCC had AFP serum levels less than 20 ng/mL, which is considered AFP-negative. The 3-DNA marker panel by short-amplicon assays used in urine was found in 91% (40/44) of the AFP-negative HCC urine, thereby increasing the sensitivity of detecting HCC from 42% (32/76) with AFP alone to 97% (72/76) by combining HCC urine test with serum AFP.

The invention is further illustrated by the following non-limiting examples.

EXAMPLES

Example 1

Study Subjects and Methods

Samples for this study were acquired under IRB (institutional review board) approval from the National Cheng-Kung University Medical Center in Taiwan, which provided 120 tissue samples from cancer patients who had undergone surgical resection, as well as noncancerous adjacent tissue to trace methylation throughout the pathology of HCC. Additional diseased tissue (35 hepatitic and 35 cirrhotic) was also obtained under IRB approval from the Buddhist Tzu Chi Medical center in Hualien, Taiwan. One normal liver sample was obtained from Immunotope, Inc. (Doylestown, Pa.), two from Johns Hopkins University School of Medicine (Baltimore, Md.), and one purchased from Capital Biosciences (Rockville, Md.), again, all in accordance to IRB protocols. The clinicopathological characteristics of these samples (grouped by BS-PCR DNA sequencing, Table 1/MSP use, Table 1) are provided in Tables 1 and 2. Moreover, eight other non-liver normal tissues and one fetal liver sample were also sequenced. The subject profiles for these samples can be found in Table 2. The urine samples were collected at the National Cheng-Kung University Medical Center in accordance with the guidelines of the institutional review board. The subject information is provided in Table 3.

TABLE 1

Subject information for BS-PCR DNA sequencing.

| Characteristic | Normal n = 4 | Hepatitis n = 5 | Cirrhosis n = 5 | HCC and adjacent non-HCC n = 5 |
|---|---|---|---|---|
| Mean Age ± SD◊ | 65.3 ± 9.6 | 60.6 ± 14.9 | 60 ± 10.4 | 63 ± 10.7 |
| Male/Female | 1/3 | 1/4 | 3/2 | 4/1 |
| HBV/HCV/both/non-viral or unknown | — | 1/2/1/1 | 2/2/0/1 | 1/2/0/2 |
| Stage 1/2/3/4/unknown | — | — | — | 3/2/0/0/0 |
| Grade 1/2/3/unknown | — | — | — | 0/2/3/0 |
| Mean size of tumor ± SD | — | — | — | 7.1 ± 2.2 cms |
| AFP levels ≤20/>20 ng/ml/unknown | — | — | — | 1/4/0 |

F, female;
HCC, hepatocellular carcinoma;
M, male;
NA, not applicable

TABLE 2

Study subjects for MSP assays

| Characteristic | Hepatitis n = 35 | Cirrhosis n = 35 | HCC and adjacent non-HCC n = 20 | P value |
|---|---|---|---|---|
| Mean Age ± SD<sup>◊</sup> | 55 ± 11.62 | 56 ± 13.8 | 60 ± 11.3 | 0.07§ |
| Male/Female | 17/18 | 23/12 | 81/39 | 0.175§ |
| HBV/HCV/non-viral or unknown | 3/22/9/1 | 6/16/0/13 | 59/29/4/28 | — |
| Stage 1/2/3/4/unknown | — | — | 48/48/16/4/4 | — |
| Grade 1/2/3/unknown | — | — | 18/74/23/5 | — |
| Mean size of tumor ± SD | — | — | 5.31 ± 3.69 cms | — |
| AFP levels ≤20/>20 ng/ml/unknown | — | — | 62/53/5 | — |

<sup>◊</sup> SD, Standard deviation;
§Across all subjects (n = 190), age was analyzed by Students t test and gender by Fisher's exact test

TABLE 3

Study subjects for the P1 shMSP urine test

| Characteristic | Hepatitis (n = 44) | Cirrhosis (n = 50) | HCC (n = 40) |
|---|---|---|---|
| Mean age ± SD, years | NA | 58.7 ± 0.7 | 55.2 ± 14.7 |
| Male/female/unknown | 25/18/1 | 33/17/0 | 29/10/1 |
| HBV/HCV/both/none/unknown | 2/1/21/20/0/0 | 11/24/4/10/0 | 22/10/0/4/4 |
| Stage 1/2/3/4/unknown | — | — | 9/17/10/0/4 |
| Grade 1/2/3/unknown | — | — | 3/25/9/3 |
| Mean size of tumor ± SD, cm | — | — | 4.96 ± 3.2 |
| AFP levels, ng/mL, ≤20/>20/unknown | — | — | 23/16/1 |

DNA Isolation (Tissue and Urine) and Bisulfite Treatment

Tissue DNA was isolated by using the Qiagen DNAeasy Blood and Tissue Kit™ (Qiagen, Valencia, Calif.) according to the manufacturer's instructions. The DNA concentration was measured using a Nanodrop 1000™ spectrophotometer (Thermo Fisher Scientific Inc, Wilmington, Del.) at 260 nm absorbance. The procedures for urine collection and urine DNA isolation were described previously [53]. Briefly, 0.5 M EDTA, pH 8.0, was added to a fresh urine sample to a final concentration of 10 mM EDTA to inhibit possible nuclease activity and stored at −70° C. To isolate total urine DNA, the frozen urine sample was thawed at room temperature and then placed immediately in ice prior to DNA isolation. DNA was isolated from thawed urine within an hour. Urine samples were mixed with 1 volume of 6M guanidine thiocyanate by inverting 8 times. Then, 1 ml of resin (Wizard DNA purification kit, Promega, Madison, Wis.) was added to the urine lysate and incubated for 2 hours to overnight at room temperature with gentle mixing. The resin-DNA complex was centrifuged, transferred to a mini-column (provided in the kit), and washed with a buffer provided by the manufacturer; the DNA was then eluted with Tris-EDTA buffer. DNA from paraffin-embedded tissue sections was isolated using the MasterPure DNA kit (Epicentre, Madison, Wis.) per the manufacturer's instructions. The LMW urine DNA fractions were obtained using carboxylated magnetic beads (CMBs) (Agencourt Bioscience Corporation, Beverly, Mass.) and a binding method developed previously by our laboratory [49]. Total urine DNA (resuspended in Tris-EDTA buffer) was mixed with 5 M NaCl and 20% polyethylene glycol 8000 (AMRESCO Inc., Solon, Ohio) to final concentrations of 0.3 M and 8%, respectively. The CMB suspension (Agencourt Bioscience Corporation) was washed and resuspended with Tris-EDTA buffer prior to use. Ten microliters of prewashed CMB suspension was added to the DNA mix and incubated for 1 to 2 hours at room temperature to allow binding of HMW DNA to the beads. The beads bound with HMW DNA were then removed from the suspension using a magnetic plate (Agencourt Bioscience Corporation). The LMW DNA remaining in the suspension was collected by adding 10 μL of prewashed CMB in a solution of 1.2 M NaCl and 10% polyethylene glycol 8000. The beads bound with LMW or HMW DNA were then washed with 75% ethanol and the DNA was eluted in Tris-EDTA buffer. Bisulfite treatment was performed using Qiagen Epitect Bisulfite conversion Kits™ (Qiagen) and Zymo EZ DNA Methylation-Lightning Kit (Zymo Research, Irvine, Calif.) following the guidelines of the manufacturer.

BS-PCR DNA Sequencing

Bisulfite specific primers were designed using Methyl Express Software™ (ABI, Foster City, Calif.) to amplify the promoter region of the P1, P2, and E1 regions of the RASSF1A genes; the primer sequences are described in Table 4.

TABLE 4

Primer and probe sequences used for bisulfite DNA sequencing and methylation specific PCR for detecting the P1, P2 and E1 regions of the RASSF1A gene (Genbank accession number: DQ444319.1)

| Primer | Sequence | Annealing (° C.) | CpG (#) within the nt. 357-981 | Product Size (bp) |
|---|---|---|---|---|
| P1 BSP | F: 5'-gtaggttaagtgtgttgttttt-3' (SEQ ID NO: 1)<br>R: 5'-ttacccttccttccctcctt-3' (SEQ ID NO: 2) | 54 | 1-12 | 192 |
| P2 BSP | F: 5'-aggagggaaggaagggtaag-3' (SEQ ID NO: 3)<br>R: 5'-taactttaaacgctaacaaa-3' (SEQ ID NO: 4) | 53 | 13-30 | 207 |
| E1 BSP | F: 5'-aagtcggggttcgttttgtggttt-3' (SEQ ID NO: 5)<br>R: 5'-ccccaaataaaatcgccacaaaaa-3' (SEQ ID NO: 6) | 53 | 24-59 | 302 |
| P1 MSP | F: 5'-agaaatacgggtattttcgc-3' (SEQ ID NO: 7)<br>R: 5'-caccccgaacgaccacaa-3' (SEQ ID NO: 8)<br>Probe: 6FAM-accacaacgacgacgaccgc-BHQ1 (SEQ ID NO: 9) | 56 | 3-11 | 61 |
| P2 MSP | F: 5'-gggttttgcgagagcgcg-3' (SEQ ID NO: 10)<br>R: 5'-aaaccgcgcaataaaaacc-3' (SEQ ID NO: 11)<br>Probe: 6FAM-cgcgaaccgaacgaa-BHQ1 (SEQ ID NO: 12) | 56 | 14-20 | 75 |

TABLE 4 -continued

Primer and probe sequences used for bisulfite DNA sequencing and
methylation specific PCR for detecting the P1, P2 and E1 regions of the RASSF1A gene
(Genbank accession number: DQ444319.1)

| Primer | Sequence | Annealing (° C.) | CpG (#) within the nt. 357-981 | Product Size (bp) |
|---|---|---|---|---|
| E1 MSP | F: 5'-gtgttaacgcgttgcgtatc-3' (SEQ ID NO: 13)<br>R: 5'-aaccccgcgaactaaaaacga-3' (SEQ ID NO: 14) | 60 | 42-54 | 93 |
| P1 shMSP | P1_SMF2: 5'-aaatacgggtattttcgc-3' (SEQ ID NO: 15)<br>P1_TMR1: 5'-gctcttcgtggtgtggtggaccacaacgacgacgac-3' (SEQ ID NO: 16)<br>R_P1_S2F1: 5'-acgggtattttcgcgtg-3' (SEQ ID NO: 17)<br>R_P1_S2R: 5'-ttcgtggtgtggtggac-3' (SEQ ID NO: 18) | 57<br><br><br>58 | 3-9 | 49 |

Bisulfite treated DNA from 4 normal, 5 hepatitic, 5 cirrhotic, 5 adjacent non-HCC, and 5 HCC tissue samples was amplified by PCR using primers from Yan et al. (P1, P2, and E1; represented in Table 4 and FIG. 1A). All PCR reactions were performed in an Eppendorf Thermocycler, with conditions of 95° C. for 5 min, 40 cycles of 95° C. for 30 s, the annealing temperature for 30 s, 72° C. for 30 s, and 72° C. for 5 minutes, followed by a 4° C. cooling. Annealing temperatures were 54° C. for P1, and 53° C. for E1 and P2. Each reaction was assembled in a final volume of 20 µl, comprising 0.5 U HotStart Taq, 1×PCR buffer, 200 µM of dNTPs, 0.5 µM of each primer, and bisulfite-treated DNA templates. PCR products were then visualized on 1.5% agarose gels, excised and extracted using Qiaquick Gel Extraction Kit (Qiagen) according to manufacturer's specifications, and sequenced. Sequencing was performed by the NAPCore facility at the Children's Hospital of Philadelphia, Philadelphia, Pa., where the vacuum dried gel extracted sample and an appropriate primer were sent. Sequences were compared to known sequences of each region's PCR product, and CpG methylation analyzed by comparing the presence of cytosine versus thymine using visual sequence representations in chromatograms. Sequencing results were analyzed using ClustalW software (available at http://www.ch.embnet.org/), Chromas 2.3 software (Technelysium, Tewantin, Queensland, Australia), and Finch TV version 1.4.0 (Geospiza Inc, Seattle, Wash.).

Methylation Specific PCR

Three quantitative real time PCR assays were developed with primer pairs and Taqman probes as shown in Table 3. For the P1-MSP, A 10-µl reaction was assembled using the FastStart TaqMan Probe Master™ (Roche Applied Science, Mannheim, Germany). The reaction contained 1× FastStart TaqMan Probe Master™, 1.0 µM primers, and the DNA template. Using the Roche Light Cycler 480 Real-Time PCR System™, the PCR reaction was performed under the following conditions: 95° C. 10 min, (95° C. 10 s, 56° C. 30 s, 72° C. 10 s)×50 cycles, 40° C. 30 s. For the P2-MSP, A 10-µl reaction was assembled using the Light Cycler Taqman Master™ (Roche Applied Science, Mannheim, Germany). The reaction contained 1× Taqman Master Mix™, 1.0 µM primers, and the DNA template. Using the Roche Light Cycler LC480 Real-Time PCR System™, the PCR reaction was performed under the following conditions: 95° C. 10 min, (95° C. 10 s, 56° C. 15 s, 72° C. 10 s)×50 cycles, 40° C. 30 s. For the E1-MSP, A 10-µl reaction was assembled using the Light Cycler LC480 SYBR Green Mix™ (Roche Applied Science, Mannheim, Germany). The reaction contained 1×LC480 SYBR Green Mix™, 1.0 µM primers, 2.5 mM MgCl₂, and the DNA template. Using the Roche Light Cycler 480 Real-Time PCR System™, the PCR reaction was performed under the following conditions: 95° C. 10 min, (95° C. 10 s, 60° C. 15 s, 72° C. 10 s)×50 cycles, 40° C. 30 s. For the P1-shMSP, a first step PCR of 10-µl reaction was assembled. The reaction contained 1 unit HotStart Taq polymerase (Qiagen), 1× HotStart PCR buffer, 0.1 µM primers, 2.5 mM MgCl₂, and the DNA template. Using the Eppendorf Thermal Cycler (Eppendorf North America, Hauppauge, N.Y.), the PCR reaction was performed under the following conditions: 95° C. 10 min, (95° C. 30 s, 57° C. 30 s, 72° C. 30 s)×25 cycles, 72° C. 4 min. The second-step PCR was assembled as the Table below.

| Component | Stock Concentración | Final Concentración | uL/reaction |
|---|---|---|---|
| LC480 SYBR Green Mix | 2X | 1X | 5 |
| R_P1_S2F1/S2R | 10 uM | 1 uM | 1 |
| 1st PCR Product (1:10) | — | — | 1 |
| H₂O | — | — | 3 |
| Total | | | 10 |

Using the Roche Light Cycler 480 Real-Time PCR System™, the PCR reaction was performed under the following conditions: 95° C. 5 min, (95° C. 10 s, 58° C. 30 s, 72° C. 10 s)×35 cycles, 40° C. 30 s.

GSTP1 shMSP

The clinicopathological characteristics of urine samples were collected at the National Cheng-Kung University Medical Center in accordance with the guidelines of the institutional review board and the subject information are provided in Table 5.

TABLE 5

Study subjects for the GSTP1 shMSP urine test

| Characteristic | Hepatitis (n = 58) | Cirrhosis (n = 35) | HCC (n = 44) |
|---|---|---|---|
| Mean age ± SD, years | NA | 58.7 ± 10.7 | 55.2 ± 14.7 |
| Male/female/unknown | 35/23/1 | 23/12/0 | 29/14/1 |
| HBV/HCV/both/none/unknown | 35/22/20/0/0 | 11/19/4/5/0 | 22/14/0/4/4 |
| Stage 1/2/3/4/unknown | — | — | 9/21/10/0/4 |
| Grade 1/2/3/unknown | — | — | 7/25/9/3 |
| Mean size of tumor ± SD, cm | — | — | 4.96 ± 3.2 |
| AFP levels, ng/mL, ≤20/>20/unknown | — | — | 25/18/1 |

Methylation specific primers were designed using Methyl Express Software™ (ABI, Foster City, Calif.) to amplify the promoter region of the GSTP1 gene; the primer sequences are described in Table 6.

TABLE 6

Primer and probe sequences used for shMSP assay for detecting the promoter region of the GSTP1 gene (Genbank accession number: M24485) as well as the full sequence of Genbank accession number: M24485.

| shMSP assay | Sequence | Annealing (° C.) | Location (nt.) |
|---|---|---|---|
| 1$^{st}$ PCR | GSTP1_1F: 5'-ctgtgtgctcttcgtgtgtggtgtaaggttttttcggttagttgc-3' (SEQ ID NO: 19) | 59 | 1018-1059 |
| | GSTP1_1R_LNA: 5'-taaaatccccGaaatcg-3' (SEQ ID NO: 20) | | |
| 2$^{nd}$ PCR | GSTP1_S2F: 5'-tcttcgtgtgtggtgtaaggtt-3' (SEQ ID NO: 21) | 56 | |
| | GSTP1_S2R: 5'-gccctaaaatccccgaaat-3' (SEQ ID NO: 22) | | |
| | probe: FAM-tcggttagttgcgcggcgatt-BHQ1(SEQ ID NO: 23) | | |

Capital letter in the sequence denote the LNA nucleotide
SEQ ID NO: 29 Positions 1018 to 1059 of Genbank accession number M24485 aaggcttccccggccagctgcgcggcgactc-cggggactcca For the shMSP, the protocol is shown in the table below: The first step PCR of 10-μl reaction was assembled. The reaction contained 1 unit HotStart Taq polymerase (Qiagen), 1× HotStart PCR buffer, 0.1 μM primers, 2.5 mM MgCl$_2$, and the DNA template. Using the Eppendorf Thermal Cycler (Eppendorf North America, Hauppauge, N.Y.), the PCR reaction was performed under the following conditions: 95° C. 5 min, (95° C. 30 s, 59° C. 30 s, 72° C. 30 s)×20 cycles, 72° C. 4 min. The second-step PCR was assembled as the Table below.

| Component | Stock Concentration | Final Concentration | uL/reaction |
|---|---|---|---|
| 1st PCR: | | | |
| 10X PCR Buffer | 10X | 1X | 1 |
| dNTP | 2.5 mM each | 250 uM each | 0.8 |
| GSTP1_F1/45R_LNA | 10 uM | 1 uM | 1 |
| HotStart Taq Plus | 5 U/uL | 1 U/reaction | 0.2 |
| DNA Template | — | — | 1 |
| H$_2$O | — | — | 6 |
| Total | | | 10 |
| 2nd PCR: | | | |
| LC480 Probes Master | 2X | 1X | 5 |
| GSTP1 S2F1/R | 10 uM | 1 uM | 1 |
| GSTP1 Sh.Amp. TQ3 | 3 uM | 0.15 uM | 0.5 |
| 1st PCR Product | — | — | 1 |
| H$_2$O | — | — | 2.5 |
| Total | | | 10 |

Eppendorf Thermal Cycler: 95° C. 5 min, (95° C. 30 s, 59° C. 30 s, 72° C. 30 s) × 20 cycles, 72° C. 4 min, 4° C. Hold Using the Roche Light Cycler 480 Real-Time PCR System™, the PCR reaction was performed under the following conditions: 95° C. 10 min, (95° C. 10 s, 56° C. 30 s, 72° C. 10 s)×40 cycles, 40° C. 30 s.

Statistical Analysis

To test whether age and gender were evenly distributed across both HCC and non-HCC groups, the Student t test was performed for age and Fisher's exact test was performed for gender. ROC curves, areas under the ROC curves was constructed using the PASW software (IBM, New York).

A Short Amplicon Quantitative PCR Assay for Detecting TP53 249 Mutations

To discriminate between wildtype and mutated p53 sequences a locked nucleic acid (LNA) clamp was designed to inhibit amplification of wildtype DNA in the PCR assay. LNA is a chemically modified RNA nucleotide whose ribose is modified with a methylene bridge connecting the 2'-oxygen and 4'-carbon. This essentially "locks" the ribose in its structural conformation, which provides high thermostability and high affinity recognition to complementary DNA. FIG. 1 is chemical structure representation of the difference between LNA and RNA.

A short amplicon was designed for targeting short templates as shown in FIG. 12. A Locked Nucleic Acid (LNA) Clamp was designed for inhibition of WT amplification as described above. SimpleProbe® (Roche, Indianapolis, Ind.) was designed for melting curve analysis to identify mutations.

The following LC 480 Real-Time PCR Protocol was used: The quantitative p53 codon 249T mutation assay was modified from the previously reported p53 codon 249T mutation LNA clamp-mediated PCR assay (Lin et al., 2011). We targeted a 41-bp DNA fragment from nt position 14048 to 14092 of the TP53 gene (GenBank no. X54156); the sequences and locations of primers are listed in Table 7. The first step PCR was assembled in a final volume of 10 μL containing 1.0 U Hot Start Taq (Qiagen, Valencia, Calif.), 1×PCR buffer, 2.5 μmol/L deoxynucleotide triphosphates, 1 μmol/L of each primer (P53_qF & P53_qR), 2 μmol/L of p53_LNA clamp, and DNA templates. The cycle profile was 95° C. for 15 minutes to activate Taq polymerase, followed by 25 cycles of 95° C. for 30 seconds, 54° C. for 30 seconds, and 72° C. for 20 seconds. The PCR product was subsequently diluted 1:100. The second step PCR was assembled in a final volume of 20 μl using the LightCycler® 480 Genotyping Master (Roche Applied Science, Mannheim, Germany). The reaction contained 4 μl Genotyping Master Mix, 0.10 μmol/L p53_qF primer, 0.5 μmol/L p53_249R primer, 0.15 μmol/L of the codon 249T-specific SimpleProbe (p53_249_T_probe), and the diluted PCR product. By using the Roche LightCycler® 480 Real-Time PCR system (Roche Applied Science, Indianapolis, Ind.), the PCR was performed under the following conditions: 95° C. for 10 minutes; then, 95° C. for 10 seconds, 54° C. for 15 seconds, and 72° C. for 10 seconds for 32 cycles; and, finally, the melting curve at 95° C. for 1 minute and cooled to 30° C. for 2 minutes. The temperature was then increased at a transition rate of 0.06° C./second to 70° C. for continuous hold.

TABLE 7

Sequence and Location of Oligonucleotides Used in TP53 249T quantitative assay

| Primer and probe name | Nucleotide location | Sequence |
|---|---|---|
| P53_qF | 14050-14065 | 5-CTGCATGGGCGGCATG-3 Seq ID No: 24) |
| P53_qR | 14066-14084 | 5-TGAGGATGGGCCTCCGGTT-3 (Seq ID No: 25) |
| P53_249R | 14076-14090 | 5-TGATGGTGAGGATGG-3 (Seq ID No: 26) |
| P53_LNA | 14070-14076 | 5-*GGAGGCC*-3 (Seq ID No: 27) |
| P53_249_T probe | 14067-14078 | 5-ACCG*GA*G*T*CCCA-3 (Seq ID No: 28) |

[1]*The nucleotide position is based on the genomic sequences GenBank accession no. X54156.
The boldfaced and italicized bases denote locked-nucleic acid bases (LNA)

A first PCR reaction is performed as follows: Assemble a PCR reaction containing 10 µl total volume in 96-well plate. The first step PCR was assembled in a final volume of 10 µL containing 1.0 U Hot Start Taq (Qiagen, Valencia, Calif.), 1×PCR buffer, 2.5 µmol/L deoxynucleotide triphosphates, 1 µmol/L o each primer (P53_qF & P53_qR), 2 µmol/L of p53_LNA clamp, and DNA templates. The cycle profile was 95° C. for 15 minutes to activate Taq polymerase, followed by 25 cycles of 95° C. for 30 seconds, 54° C. for 30 seconds, and 72° C. for 20 seconds. The PCR product was subsequently diluted 1:100. Place the plastic sealing foil over the 96-well plate and seal well. Centrifuge the 96-well plate briefly before placing in LC480™ Real-time PCR machine. Run reaction at the following PCR amplification conditions: 95° C. for 5 mins, then 95° C. for 30 s, 54° C. for 30 s, 72° C. for 30 s for 40 cycles followed by elongation at 40° C. for 30 s. Keep PCR products at 4° C. until ready to use.

For the second step quantitative PCR: The PCR product was subsequently diluted 1:100. The second step PCR was assembled in a final volume of 20 µl using the LightCycler® 480 Genotyping Master (Roche Applied Science, Mannheim, Germany). The reaction contained 4 µl Genotyping Master Mix, 0.10 µmol/L p53_qF primer, 0.5 µmol/L p53_249R primer, 0.15 µmol/L of the codon 249T—specific SimpleProbe (p53_249_T_probe), and the diluted PCR product. By using the Roche LightCycler® 480 Real-Time PCR system (Roche Applied Science, Indianapolis, Ind.), the PCR was performed under the following conditions: 95° C. for 10 minutes; then, 95° C. for 10 seconds, 54° C. for 15 seconds, and 72° C. for 10 seconds for 32 cycles; and, finally, the melting curve at 95° C. for 1 minute and cooled to 30° C. for 2 minutes. The temperature was then increased at a transition rate of 0.06° C./second to 70° C. for continuous hold for melting curve analysis to characterization of the products.

Statistical Analysis

The methylation density analysis for BSP direct sequencing and BSP cloning and sequencing was statistically evaluated using a two-sided Pearson $\chi^2$ test to compare HCC with adjacent normal liver and HCC with normal liver. For BSP direct sequencing, analysis was done in two ways: (i) including the data for all available CpG sites and (ii) ignoring CpG sites that had data unavailable for any of the samples. For sequencing methylation density analysis, the total number of methylated CpG sites that is equal or more than 50% methylation for each tissue group (HCC vs. normal liver and HCC vs. adjacent non-HCC) were compared using the Pearson $\chi^2$ test. Receiver operating curves (ROC) for all assays were generated using methylation concentration values by the SPSS software (IBM). Specificity and sensitivity of all assays were assessed using ROC coordinates. The specificities of each assay were compared using a fixed sensitivity.

To test whether age and gender were evenly distributed across both HCC and non-HCC groups, the Student t test was performed for age and Fisher's exact test was performed for gender. ROC curves, areas under the ROC curves was constructed using the PASW software (IBM, New York).

Example 2

Comparison of the Extent of DNA Methylation on the P1, P2, and E1 Regions of the RASSF1A Gene in Hepatocarcinogensis by Bisulfite-Specific Polymerase Chain Reaction (BS-PCR) and Sequencing To determine whether the location of the promoter analyzed in the RASSF1A gene may impact the specificity of the methylated RASSF1A (mRASSF1A) gene as a biomarker for distinguishing HCC from other liver diseases such as cirrhosis and hepatitis, every CpG site in the region of interest is examined by bisulfite PCR sequencing in a small sample size of tissue DNA (5 for each disease group). Although every CpG site within the amplified region can be analyzed via BS-PCR sequencing, only a small-sized sample is sequenced this way, due to the fact that BS-PCR sequencing is tedious, time-consuming and costly, the finding from the small-sized sample is then confirmed by examining a larger-sized sample of tissue DNA using methylation-specific PCR (MSP) assay. These MSP assays are simple and inexpensive, although only a subset of CpG sites included in primers and probes are analyzed. FIG. 1A shows CpG sites (vertical bars) in the promoter and first exon regions of the RASSF1A gene which were previously named [54] along with locations of bisulfite sequencing primers (BSP) used. The primer sequences are listed in Table 1. Fifty nine CpG sites within the 575-bp region studied were numbered from 1 to 59 in the 5' to 3' direction.

To analyze the extent of methylation at each CpG site by BS-PCR sequencing and to normalize the primer or sequencing software bias, we established a reference index for each primer set (FIG. 1C) based on the BS-PCR sequencing data of the reconstituted standards (FIG. 1B). Sequencing results were analyzed using chromatograms and comparisons of thymine versus cytosine peaks at the CpG sites which would appear in PCR products of unmethylated and methylated bisulfite-treated DNA, respectively. The $^m$CpG is categorized into four groups: (1) T only (0% methylation detected, open boxes); (2) C less than or equal to T ($^m$C detected on less than 10% of total DNA, dotted boxes); (3) C greater than T ($^m$C detected on ~10%-25%, hatched boxes); and (4) C only ($^m$C detected on ~25% or more of the DNA, solid boxes), as shown in FIG. 1C. As shown in FIG. 1B, the P1 and E1 primer pairs were not able to detect 10% methylation but detected 25% methylation; the cytosine peak height was less than or equal to thymine. The sensitivity for the P1 and E1 primer sets was in the range of 10-25% methylation. The P2 primer set, however, was the least sensitive of the three. It did not pick up 25% methylated DNA and had a sensitivity in the range of 25% and 50%. For all three primer sets, the height of cytosine peak exceeding that of thymine was an indication of greater than 50% methylation.

BSP was carried out on bisulfite-treated DNA samples from HCC, matched adjacent non-HCC, normal liver, hepatitis-infected, and cirrhotic tissues followed by direct DNA sequencing of the PCR product. Using these individualized reference indices for each primer set, the extent of DNA methylation is estimated for these three regions (P1, P2 and E1) on DNA isolated from tissues of all stages of the HCC pathology—normal, hepatitic, cirrhotic, adjacent non-HCC, and HCC. As described herein, DNA was bisulfite treated, subjected to PCR amplification using BSP primers for the P1, P2, and E1 regions. PCR products were purified and sequenced. The extent of DNA methylation for each CpG site was scored based on the reference index described in FIG. 1. The data is summarized in FIG. 2A. Comparing the data obtained from normal livers, hepatitis, cirrhosis, HCC and matched adjacent non-HCC liver tissue, HCC tissue samples had the highest level of methylation in all three P1, P2, and E1 regions, similar to previous reports in literature [54].

To analyze the methylation status of these three regions quantitatively across the various tissue types, total CpG sites from all samples are pooled and assigned into two categories: (i) "low methylation": less than 50% methylation and (ii) "high methylation": greater than or equal to 50% methylation. The percentage of CpG sites is then calculated. CpG sites with "high" methylation are summarized in the inserted table in FIG. 2. While more than 85% of CpG sites studied in each region were significantly methylated (i.e., >50%) in HCC, the methylation level of the P1 region was significantly less in non-cancerous disease liver tissue (hepatitis and cirrhosis). More specifically, P1 region methylation levels are 25.5% and 23.6% for hepatitis and cirrhosis, respectively, while E1 region methylation levels are 57.9% and 38.6% for hepatitis and cirrhosis, respectively, and P2 region methylation levels are 77.5% and 67.5 for hepatitis and cirrhosis, respectively. Fishers exact test (P<0.001) (FIG. 2B) suggests that P1 is the most specific region to HCC as compared to P2 and E1 regions.

Example 3

Methylation of the RASSF1A Gene Contributes to the Microenvironment in Liver Carcinogenesis By comparing the extent of DNA methylation detected in the adjacent non-HCC tissue to other non-HCC tissues, such as hepatitis and cirrhosis, the implication of cancer field effect by DNA methylation of the RASSF1A gene was identified. The 2×2 contingency tables comparing DNA methylation between adjacent non-HCC and hepatitis/cirrhosis for each region were constructed as shown in Table 7. The p-value was calculated for each region by Fisher's exact two-tailed test comparing the association between adjacent non-HCC tissue and other non-HCC disease liver tissues, such as hepatitis and cirrhosis. The adjacent non-HCC tissue had significantly higher methylation than the hepatitis/cirrhosis tissue for P1, P2 and E1 regions. The p-values are: p<0.0001 for P1, p=0.0087 for P2, and p<0.0001 for E1. These data indicate that methylation of the RASSF1A gene might contribute to a cancer field effect in liver carcinogenesis. The normal liver tissues in this analysis included tissue samples of liver that was adjacent to cholangiocarcinoma, which again suggests the presence of possible cancer field effect. Consequently, the normal liver tissues adjacent to carcinogenesis show high methylation level in 29 of 44 (65.9%) of CpG sites in the P1 region, in 78 of 116 (67.2%) of CpG sites in the E1 region, in 44 of 64 (68.8%) of CpG sites in the P2 region.

TABLE 7

Analysis of the extent of DNA methylation of the RASSF1a gene by 2 × 2 contingency tables.

| Methylation[1] | P1 | | | P2 | | | E1 | | |
|---|---|---|---|---|---|---|---|---|---|
| | Low | High | Total | Low | High | Total | Low | High | Total |
| Adj HCC | 21 | 34 | 55 | 10 | 70 | 80 | 40 | 105 | 145 |
| Hepatitis + cirrhosis | 83 | 27 | 110 | 44 | 116 | 160 | 150 | 140 | 290 |
| Total | 104 | 61 | 165 | 54 | 186 | 240 | 190 | 245 | 435 |
| p-value[2] | | 0.0001 | | | 0.0087 | | | 0.0001 | |

[1]The extent of DNA methylation is categorized as "Low: <50% methylation detected" and "High: ≥50% methylation detected" by BSP sequencing based on the reference index generated in FIG. 1C.
[2]p values were generated by Fisher's exact two-tailed test.

Example 4

Methylation Specific PCR Demonstrates that DNA Methylation of the P1 Region is the Most Specific Region Among Three Regions Examined as a Biomarker for Distinguishing HCC from Other Liver Disease Tissue In order to confirm the finding derived from BS-PCR sequencing in a larger sample size, MSP assays were adapted (E1, Yeo et al. 2005) or developed (P1 and P2) for the RASSF1A promoter and the first exon region. The areas targeted by these primers are shown in FIG. 3A. All assays were optimized and the linearity of the assay was determined by using various diluted reconstituted standards, as described in FIG. 3B. Each assay was validated by testing samples for which the methylation status was known based on sequencing data. All three assays have a sensitivity of 10 copies. For the E1 assay, melting curve analysis was also used to characterize the PCR product for evaluation of each amplification.

As aforementioned, because MSP assay is inexpensive and capable of much higher throughput as compared to BS-PCR DNA sequencing. Consequently, a larger sample size of diseased liver DNA could be easily tested by the MSP assays to validate the finding obtained from the smaller size study using BS-PCR sequencing, shown in FIG. 2. Thus, the performance of these three regions as DNA markers to distinguish HCC from other liver diseases in a large sample (e.g., 120 HCC, 35 cirrhosis, and 35 hepatitis tissues) was evaluated. The clinical-pathological information for this population is described in Table 2.

Using the quantitative real-time PCR assay system, methylation concentrations for every sample were calculated in duplicates and averaged. These values were then analyzed using SPSS software (IBM) and receiver operating curves (ROC) were constructed for each region. These curves measure the general goodness of the test as a binary classifier as a function of the area under the curve (AUROC), with a perfect test having an AUROC=1. As shown in FIG. 3C, P1 is a statistically better test than both E1 and P2 because P1's AUROC is 0.90, compared to 0.84 for E1 and 0.72 for P2 (P1 vs E1, P=0.0256; P1 vs P2, P<0.0001; E1 vs P2, P=0.0024: StAR: Statistical Comparison of ROC Curves). The sensitivity and specificity of a quantitative test depend on the cut-off value above or below which the test is positive. In general, the higher the sensitivity, the lower the specificity, and vice versa. Thus, to compare the specificity, the sensitivity was fixed at 90%, 75%, 50%, and 25%, as listed in Table 2; At 90% sensitivity, the P1 assay had a specificity of 72.9%—almost twice as specific as the E1 assay, which was only 38.6% specific. The P1 assay was also far better than the P2 assay, which was merely 27.1% specific (P<0.0001 by Fisher's exact 2-tailed test). A similar trend was observed at all other fixed values of sensitivity. Taking into account the AUROC and the specificity analysis, we conclude that P1 is the best region in the RASSF1A promoter region for methylation analysis in the context of liver cancer screening. Since 10-copies is the linear limit of detection for the assay, 10-copies cutoff (10 copies per 3000 copies of actin-quantified tissue DNA input) was chosen for further analysis. At this cutoff, the P1 MSP gave a sensitivity of 80.8% and specificity of 85.7%.

Example 5

DNA Methylation of the RASSF1A Gene Varies Among Different Tissue Types

Previous studies had revealed a liver specific methylation pattern in the APC and GSTP1 genes. Hence, it was of interest to compare the DNA methylation pattern of normal liver to other non-liver normal tissues. The methylation profile of the RASSF1A does not seem to exert a liver-specific pattern, because similar DNA methylation levels to liver was found in kidney and pancreatic tissue. However, most of other non-liver normal tissues examined, such as spleen, lung, breast, stomach, colon, trigeminal ganglion and fetal liver, did not contain detectable level of DNA methylation in the RASSF1A gene when analyzed by BS-PCR sequencing. Interestingly, CpG site #16 in the P2 region was consistently methylated across all tissue types (FIG. 2B).

Example 6

Detection of AFP-negative HCC

Figure 4:
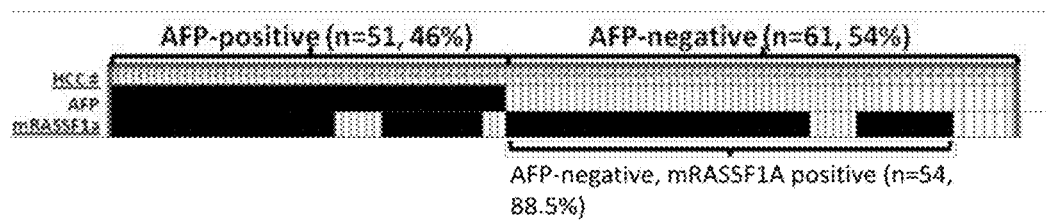
FIG. 4 shows the distribution of serum AFP and methylated RASSF1A by the P1 MSP assay in 112 HCC subjects. A 20 ng per mL cutoff was used for serum AFP and 10 copy cutoff per 300 copies (determined by BS-actin assay [2]) input tissue DNA was used for mRASSF1A. A black shaded rectangle indicates a positive result in the corresponding test and white rectangle indicates negative result.
Figure 6:
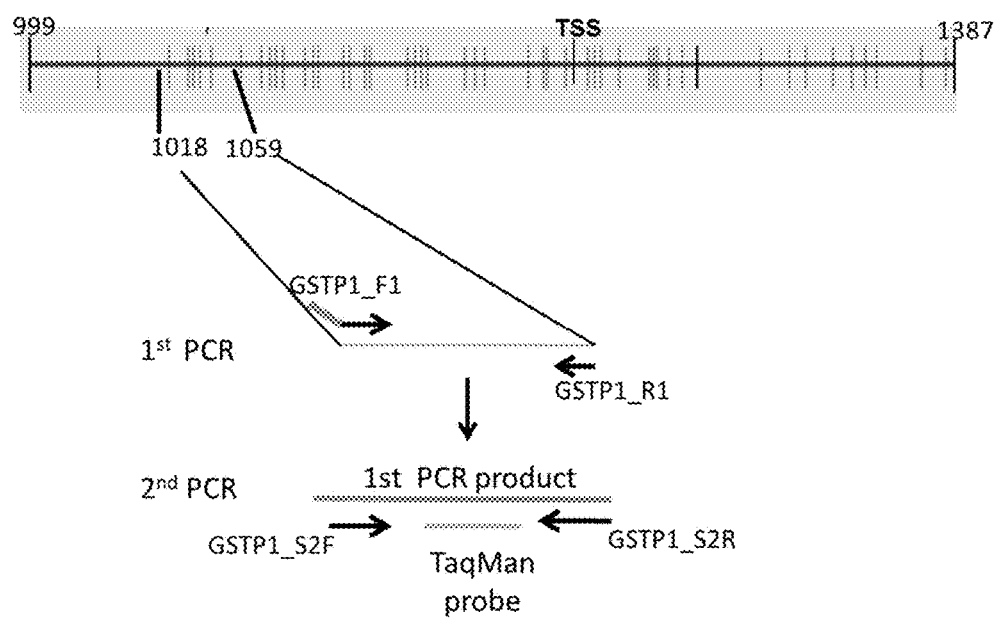
FIG. 6 shows the diagram of the locations of short-amplicon MethyLight assay and the CpG sites, indicated by vertical bars, in the promoter and the first exon regions of the GSTP1 gene (Genbank accession #M24485, nt. 999-1387). The transcription start site (TSS) is also indicated. The CpG sites are bracketed by the methylation specific primers from nt. 1018-1059 for the forward (GSTP1_F1) which also contains an artificial tag sequences (red) and reverse (GSTP1_R1) for the first step PCR reaction and GSTP1_S2F and GSTP1_S2R for the second step PCR reaction and a TaqMan probe (orange).

As aforementioned, the current clinical standard biomarker for HCC screening is serum AFP, which is unfortunately only 40-60% sensitive, given a 20 ng/mL detection threshold per AASLD guidelines. It was of interest to see whether detection of mRASSF1A marker could potentially improve the sensitivity to detect HCC by detecting AFP-negative HCC, incidence of mRASSF1A was analyzed in 115 HCC samples for which the AFP level was known, as shown in FIG. 4. The cutoff level for each test was 10 copies per 3000 copies of actin-quantified tissue DNA input for mRASSF1A and 20 ng/mL for serum AFP. Of the 115 samples, 62 samples (53.9%) were deemed AFP-negative, because their AFP levels were below the 20 ng/mL AFP-positive threshold; however, of these 62 AFP-negative samples, 54 (87.1%) were detected via the mRASSF1A marker. By combining the AFP and mRASSF1A tests, 107 of 115 (93.0%) HCC samples were correctly identified.

Example 7

Detection of Methylated RASSF1A Gene in Urine of Patients with HCC—a Biomarker for HCC Screening Most of the biomarkers discovered have been found in diseased cancer tissue, but biomarker detection will be more useful for cancer screening only if the markers can be detected in the periphery, preferably in a noninvasive fashion. For two decades an elevated cell-free circulating DNA (cfDNA) level has been suggested to be a marker for cancer. However, the increase in the amount of cfDNA in general lacks sufficient specificity and sensitivity as a marker for any specific cancer. Nevertheless, this discovery motivated the search for more specific tumor-associated modifications in cfDNA. The major challenges in the field have been assay specificity and sensitivity, because the majority of cfDNA could constitute normal DNA in addition to the tumor DNA of interest. Thus, despite the suggestion of various cancer-associated DNA modifications in the circulation, developing a test of sufficient sensitivity has been challenging [55-58].

Urine is shown to contain DNA from the circulation that can be used to detect cancer-derived genetic modifications. [48-52] and [59-63]. Malignant, benign, and even preneoplastic cells often proliferate at abnormal rates that are accompanied by an increase in apoptotic cell death. [64, 65] Such apoptotic DNA released in the circulation may be filtered through the kidney and accumulate in urine. If the transformed cells possess somatic mutations or epigenetic modifications that distinguish them from the germ line, urine could be a good source for detection and monitoring of cancer, even from extraurinary tract sites, such as liver. Previous studies demonstrated that circulation-derived DNA in urine is fragmented into segments of 300 bp (low-molecular-weight [LMW] urine DNA). Preferentially isolating LMW urine DNA from total urine DNA to use as the substrate enhanced the sensitivity and specificity of the test for detecting tumor-derived circulating DNA markers [51, 52]. Interestingly, the concentration of circulation-derived DNA in urine is comparable to that in blood [66]. Yet, unlike blood collection, urine collection is completely noninvasive. Further, urine can be collected in remote geographic areas without assistance from medical professionals. Moreover, urine contains fewer contaminants as compared with blood. Consequently DNA isolation from urine is easier. Moreover, comparing with blood larger amount of urine can be collected, resulting in more DNA available for the test, thereby increasing the sensitivity of the test.

Using LMW urine DNA as a source for cfDNA (cell-free circulating DNA) faces similar challenges as use of plasma DNA for detecting circulating tumor markers, because the available DNA is of a smaller size. Shekhtman et al. [60] and Sikora et al. [67] suggested that PCR assays targeting template sequences of 50 nt or fewer are necessary to obtain a sensitivity greater than 50% for detecting cfDNA markers.

Figure 2:
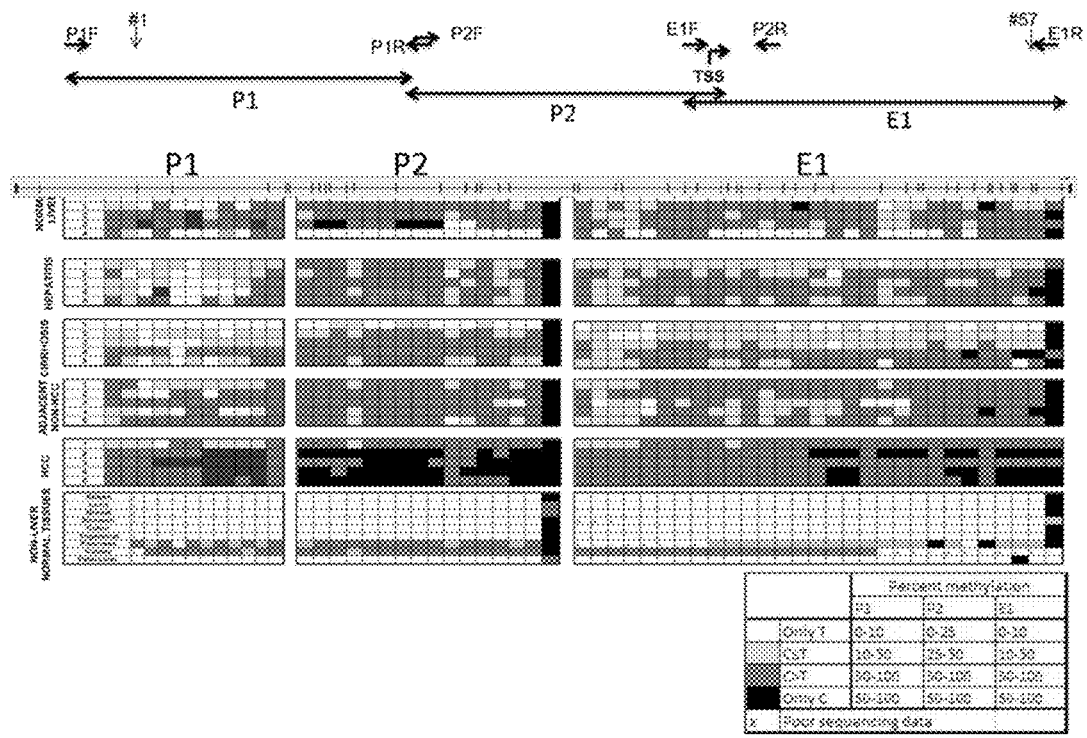
FIG. 2 shows Bisulfite sequencing analysis of the RASSF1A promoter region in normal liver, diseased liver and non-liver normal tissues. (A). Qualitative shading is based on the relative heights of cytosine and thymine peaks within the chromatogram, and four shades exist as indicated in FIG. 1(C). (B) The percentages of CpG sites with high (> or = to 50%) methylation in each liver tissue type in each region are represented above.

Detection of circulating methylated DNA markers faces even more challenges, because the substrate DNA is fragmented and in low quantity. The process of bisulfite conversion would not only lose DNA but also would further fragment the already-fragmented DNA. Therefore, to detect circulation-derived methylated RASSF1A gene in the urine of HCC patients, a short-amplicon MSP assay, P1 shMSP, is developed, targeting a 49-nt segment of the hypermethylated P1 region in the RASSF1A gene that was shown to be most specific to HCC (FIG. 2). This assay was optimized and proven sensitive for detecting up to 5 copies of methylated DNA in a background of 100c negative (FIG. 5B).

Using LMW urine DNA as the substrate and the above mentioned short-amplicon P1 shMSP assay, it is demonstrated that the circulation-derived, HCC-associated methylated DNA marker, mRASSF1A, could be detected in 90% of urine samples of patients with HCC. Using P1 shMSP assay, the LMW urine DNA isolated from 40 HCC, 50 cirrhosis, and 44 hepatitis samples were quantified for the amount of mRASSF1A DNA in the DNA isolated from 0.2 mL urine. The data was analyzed and the ROC curve was constructed as shown in FIG. 4C. The mRASSF1A P1 region demonstrates a specificity of 90.43% and sensitivity of 90% with an AUROC of 0.945 in differentiating HCC from other liver diseases including hepatitis and cirrhosis in urine.

Example 8

Detection of Methylated GSTP1 Gene in Urine of Patients with HCC—a Biomarker for HCC Screening Most of the biomarkers discovered have been found in diseased tissue, but biomarker detection will be useful for cancer screening only if the markers can be detected in the periphery, preferable in a noninvasive fashion. An elevated cell-free circulating DNA (cfDNA) level has been suggested to be a marker for cancer for two decades. However, elevated cell-free circulating DNA (cfDNA) level lacks sufficient specificity and sensitivity as a marker for any specific cancer. Nevertheless, this discovery generated the search for more specific tumor-associated modifications in cfDNA. The major challenges in the field have been specificity and sensitivity, because the majority of cfDNA contains normal DNA in addition to the tumor DNA of interest. Thus, developing a test of sufficient sensitivity has been a challenge [55-58].

Figure 7:
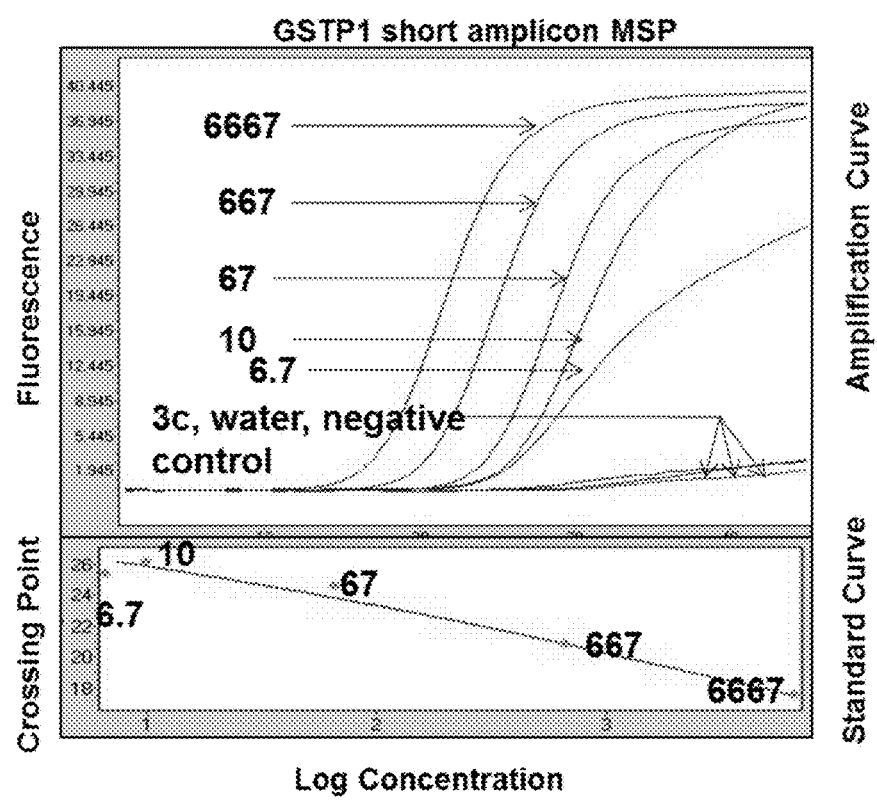
FIG. 7 shows the amplification and linearity of the shMSP assay. The various concentrations of bisulfite converted Huh7 (positive control)—with copy numbers indicated— and HeLa (negative control) were subjected to the GSTP1 shMSP assay to determine the linearity of the assay.

Urine is shown to contain DNA from the circulation that can be used to detect cancer-derived genetic modifications. Malignant, benign, and even preneoplastic cells often proliferate at abnormal rates that are accompanied by an increase in apoptotic cell death. [64, 65] Such apoptotic DNA released in the circulation may be filtered through the kidney and accumulate in urine. If the transformed cells possess somatic mutations, or epigenetic modifications that distinguish them from the germ line, urine could be a good source for detection and monitoring of cancer, even from extraurinary tract sites, such as liver. Previous studies demonstrated that circulation-derived DNA in urine is fragmented into segments of 300 bp (low-molecular-weight [LMW] urine DNA). Preferentially isolating LMW urine DNA from total urine DNA to use as the substrate enhanced the sensitivity and specificity of the test for detecting tumor-derived circulating DNA markers [51, 52]. Interestingly, the concentration of circulation-derived DNA in urine is comparable to that in blood [66]. Yet, unlike blood collection, urine collection is completely noninvasive. Further, urine can be collected in remote geographic areas without assistance from medical professionals. Moreover, urine contains fewer contaminants as compared with blood, consequently DNA isolation from urine is easier, resulting in more DNA available for the test, thereby increasing the sensitivity of the test. Using LMW urine DNA as a source for cfDNA faces similar challenges as the use of plasma DNA for detecting circulating tumor markers, because the available DNA is of a smaller size. Shekhtman et al. [60] and Sikora et al. [67] suggested that PCR assays targeting template sequences of 50 nt or fewer are necessary to obtain a sensitivity greater than 50% for detecting cfDNA markers. Detection of circulating methylated DNA markers faces even more challenges, because the substrate DNA is fragmented and in low quantity. The process of bisulfite conversion not only would lose DNA but also would further fragment the already fragmented DNA. Therefore, to detect circulation-derived methylated GSTP1 gene in the urine of HCC patients, a short-amplicon MSP assay, shMSP, is developed, targeting a 42-nt segment of the hypermethylated region in the GSTP1 gene that was shown to be most specific to HCC as illustrated in FIG. 1. This assay was optimized and proven sensitive for detecting up to 5 copies of methylated DNA in a background of 100c negative (FIG. 7).

Using LMW urine DNA as the substrate and the aforementioned short-amplicon shMSP assay, it is demonstrated that the circulation-derived, HCC-associated methylated DNA marker, mGSTP1, could be detected in 90% of urine samples of patients with HCC. Using shMSP assay, the LMW urine DNA isolated from 44 HCC, 35 cirrhosis, and 58 hepatitis samples were quantified for the amount of mGSTP1 DNA in the DNA isolated from 0.2 mL urine. The data was analyzed as shown in FIG. 8 to compare the difference between HCC and other liver diseases including hepatitis and cirrhosis.

The average amount of mGSTP1 DNA in urine was determined for each disease group and is shown in FIG. 8. The p-values between each group or in combination of groups are shown in FIG. 8 and summarized in the table below. The difference between HCC from other diseases is highly statistically significance with p-value less than 0.0001.

| Comparison | p-value |
| --- | --- |
| HCC vs. Hepatitis + Cirrhosis | <0.0001 |
| HCC vs. Cirrhosis | 0.045 |
| HCC vs. Hepatitis | <0.0001 |
| Cirrhosis vs. Hepatitis | <0.001 |

The ROC curve was constructed and the area under the curve (AUROC) was calculated as shown in FIG. 9. The AUROC of the mGSTP1 DNA marker was 0.697 (95% CI, 0.589-0.804) with a specificity of 92.5% and sensitivity of 39% differentiating HCC from other liver diseases including hepatitis and cirrhosis in urine. Encouragingly, the performance of shMSP assay detecting mGSTP1 DNA in urine is similar to that of in tissue, suggesting the high sensitivity of the assay to detect the marker in the periphery, such as in urine.

Example 9

Development of TP53 249T Quantitative Mutation Assay Using p53 249T/C and WT Clone FIG. 13 shows the results from a p53 gene real-time PCR assay. A 10-fold serial dilution of plasmid p53 DNA ranging from 1 to $10^4$ copies was used to determine the sensitivity and linearity of the assay. The data are presented as: A) Amplification curves B) Standard curve, C) Melting curves. The real-time PCR assay quantified the TP53 gene including codon 249. The assay generated a linear range from 10 to $10^4$ copies.

249T and 249WT SimpleProbe® Melt Curve Analysis of p53 standards is provided. Plasmid DNA standards 249T 1,000 copies (CP), 249C 1,000 CP, and WT 10,000 CP were subjected to a PCR reaction and the PCR product was subsequently analyzed by melt curve analysis using SimpleProbes® (B) WT probe, (C) 249T probe and (D) 249C probe. The 249T SimpleProbe distinguished the PCR products generated by mutated templates from WT templates. See FIG. 12.

Example 9

TP53 249T Mutation Assay Sensitivity is a Single Copy with a Specificity of 1:100

Sensitivity of the TP53 249T mutation assay was determined. A melt curve analysis of PCR products of 249T Standards 1000 CP to 1 CP using SimpleProbe® 249T was performed. PCR reaction was performed in the presence (+) of WT LNA clamp. The result demonstrated the assay was sensitive enough to detect a single copy. See FIG. 13.

Specificity of the TP53 249T mutation assay by using SimpleProbe® is determined. Melt Curve analysis with 249T probe was performed. The specificity of TP53 249T mutation assay was determined by (1) reconstitution of 10 CP of plasmid 249T with $10^3$ CP of WT plasmid in the absence of the WT LNA clamp. The specificity of 1:100 of 249T mutant to WT ratio was obtained. See FIG. 14.

TP53 249T mutation assay not only identified the mutation in the 249 codon, but also detected the mutation occurring in the 248 codon due to the target region of the WT LNA clamp. Consequently the assay was capable of detecting any mutation occurring in the region of the WT LNA clamp.

Example 10

Detection of HCC by a 3-DNA Marker Panel Urine Test

The performance of a 3-DNA marker panel alone or with AFP to distinguish the early stage (stage I-II, n=52, left panel) HCC or all stages (n=74, right panel) HCC from cirrhosis (n=45) and hepatitis (n=42) was assessed in urine. In this study cohort, the sensitivity of serum AFP remained limited at 44% for detecting the early stage HCC and at 41% for all HCC when using the 20 ng/mL standard cutoff as suggested by the American Association of Liver Diseases [3]. The 3-DNA marker panel had an AUROC of 0.958 (95% CI, 0.916-1.000) for detecting early HCC from cirrhosis and hepatitis and an AUROC of 0.939 (95% CI, 0.895-0.983) for detecting all stages HCC. When serum AFP is included in the 3-DNA panel, the AUROC increases to 0.993 (95% CI, 0.984-1.000) for detecting the early stage HCC and 0.982 (95% CI, 0.967-0.996) for detecting all stage HCC. By logistic regression, the sensitivity of this 3-DNA marker urine test alone or with AFP is 77% (33% better than AFP alone) or 90%, with specificity of 95%, respectively, for early stage HCC. By defining positive as any one marker positive in urine, the 3-DNA marker HCC urine test alone detected 88% of HCC urine samples. Together with AFP, 3-DNA marker HCC urine test detected 92% of HCC in urine samples. More importantly, the 3-DNA marker panel was found in 91% (40/44) of the AFP-negative HCC urine, thereby increasing the sensitivity of detecting HCC from 42% (32/76) with AFP alone to 97% (72/76) by combining HCC urine test with serum AFP.

Logistic Regression was performed on a data set using SPSS software (IBM) as shown below, with whether or not a subject has HCC as the categorical dependent variables, and the predictor variables including the number of copies of mutated TP53 per milliliter of urine, the number of copies of methylated RASSF1A per milliliter of urine, the number of copies of methylated mGSTP1 per milliliter of urine, and the concentration of alpha-fetoprotein (AFP) in urine (in ng/ml). The resulting logistic regression models (i.e., the equation variables) are shown in tables 8 and 9. The resulting raw data are shown in Table 10, 11 and 12. The cutoff for combination of markers is a probability of 0.5.

Logistic Regression of Early-Stage HCC:

| Notes | | |
|---|---|---|
| Ouput Created | | 28-NOV-2012 13:15:24 |
| Comments | | |
| Input | Data | C:\Documents and Settings\surbhi\Desktop\MISC lab\grant\EarlystageHCC.UrineJ BS3AFPHCC.Cirr.fixed.hepatitis. fixed 11.28.12.sav |
| | Active Dataset | DataSet6 |
| | Filter | <none> |
| | Weight | <none> |
| | Split File | <none> |
| | N of Rows in Working Data File | 147 |
| Missing Value Handling | Definituion of Missing | User-defined missing values are treated as missing |
| Syntax | | LOGISTIC REGRESSION VARIABLES Urinetypenumeric /METHOD=ENTER mGSTP1 mRASSF1A TP53249T AFP /SAVE=PRED PGROUP /CRITERIA=PIN(.05) POUT(.10) ITERATE(20) CUT(.5). |

-continued

| Resources | Processor Time | | 00:00:00.03 |
| | Elapsed Time | | 00:00:00.03 |
| Variables Created or Modified | PRE_2 | Predicted probability | |
| | PGR_2 | Predicted group | |

[DataSet6] C:\Documents and Settings\surbhi\Desktop\MISC lab\grant\EarlystageHCC.UrineJBS3AFPHCC.Cirr.fixed.hepatitis.fixed11.28.12.sav Case Processing Summary

| Unweighted Cases[a] | | N | Percent |
|---|---|---|---|
| Selected Cases | Included in Analysis | 139 | 94.6 |
| | Missing Cases | 8 | 5.4 |
| | Total | 147 | 100.0 |
| Unselected Cases | | 0 | .0 |
| Total | | 147 | 100.0 |

[a]If weight is in effect, see classification table for the total number of cases.

Dependent Variable Encoding

| Original Value | Internal Value |
|---|---|
| .00 | 0 |
| 1.00 | 1 |

Block 0: Beginning Block

Classification Table[a,b]

| | | Predicted | | |
|---|---|---|---|---|
| | | Urinetypenumeric | | Percentage |
| Observed | | .00 | 1.00 | Correct |
| Step 0 | Urinetypenumeric .00 | 87 | 0 | 100.0 |
| | 1.00 | 52 | 0 | .0 |
| | Overall Percentage | | | 62.6 |

[a]Constant is included in the model.
[b]The cut value is .500

Variables in the Equation

| | | B | S.E. | Wald | df | Sig. | Exp(B) |
|---|---|---|---|---|---|---|---|
| Step 0 | Constant | −.515 | .175 | 8.621 | 1 | .003 | .598 |

Variables not in the Equation

| | | | Score | df | Sig. |
|---|---|---|---|---|---|
| Step 0 | Variables | mGSTP1 | 1.839 | 1 | .175 |
| | | mRASSF1A | 20.698 | 1 | .000 |
| | | TP53249T | 9.339 | 1 | .002 |
| | | AFP | 5.030 | 1 | .025 |
| | Overall Statistics | | 32.653 | 4 | .000 |

Block 1: Method = Enter

Omnibus Tests of Model Coefficients

| | | Ch-square | df | Sig. |
|---|---|---|---|---|
| Step 1 | Step | 152.063 | 4 | .000 |
| | Block | 152.063 | 4 | .000 |
| | Model | 152.063 | 4 | .000 |

Model Summary

| Step | −2 Log likelihood | Cox & Snell R Square | Nagelkerke R Square |
|---|---|---|---|
| 1 | 31.724[a] | .665 | .907 |

[a]Estimation terminated at iteration number 20 beacuse maximum iterations has been reached. Final solution cannot be found.

-continued

Classification Table[a]

| | | Predicted | | |
|---|---|---|---|---|
| | | Urinetypenumeric | | Percentage |
| Observed | | .00 | 1.00 | Correct |
| Step 1 | Urinetypenumeric .00 | 85 | 2 | 97.7 |
| | 1.00 | 4 | 48 | 92.3 |
| | Overall Percentage | | | 95.7 |

[a]The cut value is .500

Logistic Regression of All-Stage HCC:

Notes

| | | |
|---|---|---|
| Output Created | | 28-NOV-2012 13:04:09 |
| Comments | | |
| Input | Data | C:\Documents and Settings\surbhi\Desktop\MISC lab\grany\AllstageHCCcirrhep.version5.sav |
| | Active Dataset | DataSet5 |
| | Filter | <none> |
| | Weight | <none> |
| | Split File | <none> |
| | N of Rows in Working Data File | 170 |
| Missing Value Handling | Definition of Missing | User-defined missing values are treated as missing |
| Syntax | | LOGISTIC REGRESSION VARIABLES Urinetypenumeric /METHOD=ENTER mGSTP1 mRASSF1A TP53249TP AFP /SAVE=PRED PGROUP /CRITERIA=PIN(.05) POUT(.10) ITERATE(20) CUT(.5). |
| Resources | Processor Time | 00:00:00.05 |
| | Elapsed Time | 00:00:00.03 |
| Variables Created or Modified | PRE_2 | Predicted probability |
| | PGR_2 | Predicted group |

[DataSet5] C:\Documents and Settings\surbhi\Desktop\MISC lab\grant\AllstageHCCcirrhep.version5.sav

Case Processing Summary

| Unweighted Cases[a] | | N | Percent |
|---|---|---|---|
| Selected Cases | Included in Analysis | 161 | 94.7 |
| | Missing Cases | 9 | 5.3 |
| | Total | 170 | 100.0 |
| Unselected Cases | | 0 | .0 |
| Total | | 170 | 100.0 |

[a]If weight is in effect, see classification table for the total number of cases.

Dependent Variable Encoding

| Original Value | Internal Value |
|---|---|
| .00 | 0 |
| 1.00 | 1 |

Block 0: Beginning Block

-continued

Classification Table[a,b]

|  |  | Predicted | | |
|---|---|---|---|---|
|  |  | Urinetypenumeric | | Percentage |
| Observed |  | .00 | 1.00 | Correct |
| Step 0 | Urinetypenumeric .00 | 87 | 0 | 100.0 |
|  | Urinetypenumeric 1.00 | 74 | 0 | .0 |
|  | Overall Percentage |  |  | 54.0 |

[a]Constant is included in the model.
[b]The cut value is .500

Variables in the Equation

|  |  | B | S.E. | Wald | df | Sig. | Exp(B) |
|---|---|---|---|---|---|---|---|
| Step 0 | Constant | −.162 | .158 | 1.047 | 1 | .306 | .851 |

Variables not in the Equation

|  |  |  | Score | df | Sig. |
|---|---|---|---|---|---|
| Step 0 | Variables | mGSTP1 | 1.312 | 1 | .252 |
|  |  | mRASSF1A | 17.515 | 1 | .000 |
|  |  | TP53249T | 8.438 | 1 | .004 |
|  |  | AFP | 4.881 | 1 | .027 |
|  | Overall Statistics |  | 28.589 | 4 | .000 |

Block 1: Method = Enter

Omnibus Tests of Model Coefficients

|  |  | Chi-square | df | Sig. |
|---|---|---|---|---|
| Step 1 | Step | 159.423 | 4 | .000 |
|  | Block | 159.423 | 4 | .000 |
|  | Model | 159.423 | 4 | .000 |

Model Summary

| Step | −2 Log likelihood | Cox & Snell R Square | Nagelkerke R Square |
|---|---|---|---|
| 1 | 62.720[a] | .628 | .840 |

[a]Estimation terminated at iteration number 20 because maximum iterations has been reached. Final solution cannot be found.

Classification Table[a]

|  |  | Predicted | | |
|---|---|---|---|---|
|  |  | Urinetypenumeric | | Percentage |
| Observed |  | .00 | 1.00 | Correct |
| Step 1 | Urinetypenumeric .00 | 83 | 4 | 95.4 |
|  | Urinetypenumeric 1.00 | 11 | 63 | 85.1 |
|  | Overall Percentage |  |  | 90.7 |

[a]The cut value is .500

TABLE 8

Logistic Regression Model (Variables in the Equation) for early-stage HCC
Variables in the Equation

|  |  | B | S.E. | Wald | df | Sig. | Exp(B) |
|---|---|---|---|---|---|---|---|
| Step 1[a] | mGSTP1 | .003 | .001 | 5.096 | 1 | .024 | 1.003 |
|  | mRASSF1A | .017 | .006 | 6.540 | 1 | .011 | 1.017 |
|  | TP53249T | 1.106 | 29.083 | .001 | 1 | .977 | 3.023 |
|  | AFP | .039 | .013 | 8.336 | 1 | .004 | 1.040 |
|  | Constant | −4.152 | .787 | 27.846 | 1 | .000 | .016 |

[a]Variable(s) entered on step 1: mGSTP1, mRASSF1A, TP53249T, AFP.

TABLE 9

Logistic Regression Model (Variables in the Equation) for all-stage HCC
Variables in the Equation

|  |  | B | S.E. | Wald | df | Sig. | Exp(B) |
|---|---|---|---|---|---|---|---|
| Step 1[a] | mGSTP1 | .002 | .001 | 4.970 | 1 | .026 | 1.002 |
|  | mRASSF1A | .017 | .006 | 7.310 | 1 | .007 | 1.017 |
|  | TP53249T | 1.001 | 34.294 | .001 | 1 | .977 | 2.722 |
|  | AFP | .034 | .014 | 6.071 | 1 | .014 | 1.034 |
|  | Constant | −2.935 | .471 | 38.746 | 1 | .000 | .053 |

[a]Variable(s) entered on step 1: mGSTP1, mRASSF1A, TP53249T, AFP.

TABLE 10

Logistic regression of the 3-DNA marker panel for all-stage HCC:

| Code | Diagnosis | Urine-type numeric (1= HCC, 0 = non-HCC) | AFP ng/ml | AFP category (1 = >20, 0 = <20) | mGSTP1 (copies/ml) | mRASSF1A (copies/ml) | TP53249T (copies/ml) | JBS3 Predicted probability (based on logistic regression) | JBS3 Predicted group (cutoff = 0.5) | JBS3 + AFP Predicted probability (based on logistic regression) | JBS3 + AFP Predicted group (cutoff = 0.5) |
|---|---|---|---|---|---|---|---|---|---|---|---|
| UB45b | HCC | 1 | 160.33 | 1 | 0 | 91.2 | 0 | 0.425 | 0 | 0.982 | 1 |
| UB46b | HCC | 1 | 113.81 | 1 | 0 | 130 | 44.8 | 1.000 | 1 | 1.000 | 1 |
| UB47b | HCC | 1 | 1.25 | 0 | 0 | 122 | 0 | 0.586 | 1 | 0.299 | 0 |
| UB48b | HCC | 1 | 27.82 | 1 | 0 | 77.2 | 0 | 0.356 | 0 | 0.331 | 0 |
| UB49b | HCC | 1 | 13.33 | 0 | 0 | 632.73 | 121.3 | 1.000 | 1 | 1.000 | 1 |
| UB50b | HCC | 1 | 1.75 | 0 | 0 | 54.75 | 126.8 | 1.000 | 1 | 1.000 | 1 |
| UB51b | HCC | 1 | 2.58 | 0 | 10700 | 83.06 | 31.6 | 1.000 | 1 | 1.000 | 1 |
| UB52b | HCC | 1 | 18.19 | 0 | 0 | 386.19 | 72.8 | 1.000 | 1 | 1.000 | 1 |
| UB53b | HCC | 1 | 6.45 | 0 | 0 | 68.24 | 0 | 0.314 | 0 | 0.171 | 0 |
| UB54b | HCC | 1 | 22.37 | 1 | 0 | 57.87 | 0 | 0.269 | 0 | 0.229 | 0 |
| UB55b | HCC | 1 | 288.46 | 1 | 0 | 74.15 | 0 | 0.341 | 0 | 1.000 | 1 |
| UB56b | HCC | 1 | 231.29 | 1 | 0 | 57.5 | 0 | 0.267 | 0 | 0.997 | 1 |
| UB57b | HCC | 1 | 4.76 | 0 | 4850 | 32.39 | 0 | 0.997 | 1 | 1.000 | 1 |
| UB58b | HCC | 1 | 15160 | 1 | 0 | 53.05 | 0 | 0.249 | 0 | 1.000 | 1 |
| UB60b | HCC | 1 | 2.92 | 0 | 0 | 75.91 | 73.6 | 1.000 | 1 | 1.000 | 1 |
| UB61b | HCC | 1 | 373.89 | 1 | 0 | 50.71 | 0 | 0.240 | 0 | 1.000 | 1 |
| UB62b | HCC | 1 | 22.04 | 1 | 0 | 60.3 | 180 | 1.000 | 1 | 1.000 | 1 |
| UB63b | HCC | 1 | 32.69 | 1 | 0 | 74.51 | 35.5 | 1.000 | 1 | 1.000 | 1 |
| UB64b | HCC | 1 | 15.09 | 0 | 0 | 1008.97 | 0 | 1.000 | 1 | 1.000 | 1 |
| UB65b | HCC | 1 | 3.44 | 0 | 0 | 809.43 | 0 | 0.371 | 0 | 0.186 | 0 |
| UB66b | HCC | 1 | 3.8 | 0 | 0 | 74.27 | 14 | 1.000 | 1 | 1.000 | 1 |
| UB67b | HCC | 1 | 6.89 | 0 | 4920 | 68.15 | 0 | 0.999 | 1 | 1.000 | 1 |
| UB68b | HCC | 1 | 3416 | 1 | 4850 | 43.31 | 0 | 0.998 | 1 | 1.000 | 1 |
| UB69b | HCC | 1 | 6.65 | 0 | 0 | 79.18 | 22 | 1.000 | 1 | 1.000 | 1 |
| UB70b | HCC | 1 | 192.06 | 1 | 0 | 545.45 | 0 | 1.000 | 1 | 1.000 | 1 |
| UB71b | HCC | 1 | 703.3 | 1 | 4850 | 41.08 | 0 | 0.998 | 1 | 1.000 | 1 |
| UB72b | HCC | 1 | 5.16 | 0 | 0 | 40.15 | 0 | 0.202 | 0 | 0.110 | 0 |
| UB73b | HCC | 1 | 14.84 | 0 | 8620 | 69.08 | 0 | 1.000 | 1 | 1.000 | 1 |
| UB74b | HCC | 1 | 3.41 | 0 | 4850 | 35.31 | 0 | 0.997 | 1 | 1.000 | 1 |
| UB75b | HCC | 1 | 5.75 | 0 | 0 | 41.22 | 28.9 | 1.000 | 1 | 1.000 | 1 |
| UB76b | HCC | 1 | 0 | 0 | 6320 | 34.47 | 0 | 1.000 | 1 | 1.000 | 1 |
| UB77b | HCC | 1 | 43.71 | 1 | 4850 | 20.81 | 206.6 | 1.000 | 1 | 1.000 | 1 |
| UB78b | HCC | 1 | 2477 | 1 | 0 | 36.37 | 18 | 1.000 | 1 | 1.000 | 1 |
| UB79b | HCC | 1 | 147215 | 1 | 4850 | 38.58 | 13.3 | 1.000 | 1 | 1.000 | 1 |
| UB80b | HCC | 1 | 1.6 | 0 | 0 | 72.09 | 35.9 | 1.000 | 1 | 1.000 | 1 |
| UB81b | HCC | 1 | 19.09 | 0 | 0 | 101.17 | 30.8 | 1.000 | 1 | 1.000 | 1 |
| UB82b | HCC | 1 | 192.06 | 1 | 0 | 57.18 | 43.7 | 1.000 | 1 | 1.000 | 1 |
| UB83b | HCC | 1 | 1.81 | 0 | 0 | 57.74 | 89.6 | 1.000 | 1 | 1.000 | 1 |
| UB84b | HCC | 1 | 11.73 | 0 | 4850 | 42.18 | 0 | 0.998 | 1 | 1.000 | 1 |
| UA03 | HCC | 1 | 12.68 | 0 | 15.8 | 0 | 90.9 | 1.000 | 1 | 1.000 | 1 |
| UA05 | HCC | 1 | 24302 | 1 | 275 | 246.9 | | | | | |
| UA06 | HCC | 1 | 667.1 | 1 | 16300 | 0 | 12.8 | 1.000 | 1 | 1.000 | 1 |
| UA07 | HCC | 1 | 2.91 | 0 | 3620 | 1185 | 53 | 1.000 | 1 | 1.000 | 1 |
| UA08 | HCC | 1 | 18032 | 1 | 1110 | 115.8 | 0 | 0.871 | 1 | 1.000 | 1 |
| UA10 | HCC | 1 | 4.68 | 0 | 2990 | 0 | 84.6 | 1.000 | 1 | 1.000 | 1 |
| UA11 | HCC | 1 | 15.09 | 0 | 4190 | 0 | 0 | 0.985 | 1 | 0.998 | 1 |
| UA17 | HCC | 1 | 820.6 | 1 | 775 | 0 | 188.8 | 1.000 | 1 | 1.000 | 1 |
| UA18 | HCC | 1 | 3.53 | 0 | 11700 | 121.2 | 553.8 | 1.000 | 1 | 1.000 | 1 |
| UA19 | HCC | 1 | 6.98 | 0 | 14.2 | 3.9 | 76 | 1.000 | 1 | 1.000 | 1 |
| UA20 | HCC | 1 | 4.03 | 0 | 9.51 | 14.55 | 100.5 | 1.000 | 1 | 1.000 | 1 |
| UA21 | HCC | 1 | 6.71 | 0 | 117 | 64.5 | 0 | 0.336 | 0 | 0.200 | 0 |
| UA22 | HCC | 1 | 8.57 | 0 | 25.2 | 66.9 | 505.8 | 1.000 | 1 | 1.000 | 1 |
| UA25 | HCC | 1 | 1.78 | 0 | 3.77 | 134.1 | 41.7 | 1.000 | 1 | 1.000 | 1 |
| UA26 | HCC | 1 | 6101 | 1 | 7.92 | 50.1 | 75.2 | 1.000 | 1 | 1.000 | 1 |
| UA29 | HCC | 1 | 219.8 | 1 | 3.45 | 0 | 0 | 0.099 | 0 | 0.989 | 1 |
| UA32 | HCC | 1 | 1607 | 1 | 2.95 | 399 | 2061.1 | 1.000 | 1 | 1.000 | 1 |
| UA34 | HCC | 1 | 270.24 | 1 | 8.9 | 0 | 144.8 | 1.000 | 1 | 1.000 | 1 |
| UA40 | HCC | 1 | 114.77 | 1 | 2.69 | 0 | 0 | 0.099 | 0 | 0.720 | 1 |
| UA45 | HCC | 1 | 8.17 | 0 | 2.92 | 0 | | | | | |
| UA47 | HCC | 1 | 1.23 | 0 | 2950 | 0 | 0 | 0.907 | 1 | 0.963 | 1 |
| UA48 | HCC | 1 | 12.58 | 0 | 490 | 0 | 0 | 0.187 | 0 | 0.184 | 0 |
| UA51 | HCC | 1 | 3.1 | 0 | 1430 | 690 | 88.4 | 1.000 | 1 | 1.000 | 1 |
| UA52 | HCC | 1 | 6.01 | 0 | 13200 | 306 | 180 | 1.000 | 1 | 1.000 | 1 |
| UA55 | HCC | 1 | 6.88 | 0 | 0 | 36.9 | NA | NA | NA | NA | NA |
| UA57 | HCC | 1 | 1324 | 0 | 0 | 0 | 0 | 0.098 | 0 | 0.077 | 0 |
| UA58 | HCC | 1 | 24401 | 1 | 0.516 | 402 | NA | NA | NA | NA | NA |
| UA59 | HCC | 1 | 1.7 | 0 | 1650 | 0 | 0 | 0.574 | 1 | 0.639 | 1 |
| UA61 | HCC | 1 | 4.28 | 0 | 2500 | 0 | 214.5 | 1.000 | 1 | 1.000 | 1 |
| UA62 | HCC | 1 | 5.61 | 0 | 7.86 | 0 | 172.5 | 1.000 | 1 | 1.000 | 1 |
| UA63 | HCC | 1 | 29.11 | 1 | 2530000 | 0 | 0 | 1.000 | 1 | 1.000 | 1 |
| UA64 | HCC | 1 | 40000 | 1 | 9630 | 21.72 | 52.9 | 1.000 | 1 | 1.000 | 1 |

TABLE 10-continued

Logistic regression of the 3-DNA marker panel for all-stage HCC:

| Code | Diagnosis | Urine-typenumeric (1= HCC, 0 = non-HCC) | AFP ng/ml) | AFP category (1 = >20, 0 = <20) | mGSTP1 (copies/ml) | mRASSF1A (copies/ml) | TP53249T (copies/ml) | JBS3 Predicted probability (based on logistic regression) | JBS3 Predicted group (cutoff = 0.5) | JBS3 + AFP Predicted probability (based on logistic regression) | JBS3 + AFP Predicted group (cutoff = 0.5) |
|---|---|---|---|---|---|---|---|---|---|---|---|
| UA65 | HCC | 1 | 4.97 | 0 | 11.7 | 36 | 0 | 0.191 | 0 | 09.105 | 0 |
| UA67 | HCC | 1 | 24.74 | 1 | 9.77 | 360 | 0 | 0.995 | 1 | 0.981 | 1 |
| UA68 | HCC | 1 | 4.99 | 0 | 0 | 192 | 14.2 | 1.000 | 1 | 1.000 | 1 |
| UA71 | HCC | 1 | 8.39 | 0 | 77.8 | 135.9 | 0 | 0.681 | 1 | 0.446 | 0 |
| UA72 | HCC | 1 | 60500 | 1 | 6.45 | 0 | 0 | 0.099 | 0 | 1.000 | 1 |
| UA73 | HCC | 1 | 147215 | 1 | 0 | 132.3 | 0 | 0.637 | 1 | 1.000 | 1 |
| UA74 | HCC | 1 | 18.27 | 0 | 1590 | 0 | 57.2 | 1.000 | 1 | 1.000 | 1 |
| Cua01 | Cirrhosis | 0 | 3.5 | 0 | 21.2 | 12.2 | 0 | 0.127 | 0 | 0.071 | 0 |
| Cua02 | Cirrhosis | 0 | 2.3 | 0 | 1.37 | 25.6 | 0 | 0.158 | 0 | 0.081 | 0 |
| Cua03 | Cirrhosis | 0 | 112.4 | 1 | 41.3 | 33.3 | 0 | 0.189 | 0 | 0.818 | 1 |
| Cua04 | Cirrhosis | 0 | 8.5 | 0 | 368 | 127 | 0 | 0.733 | 1 | 0.561 | 1 |
| Cua05 | Cirrhosis | 0 | 2.5 | 0 | 14.7 | 17.5 | 0 | 0.139 | 0 | 0.074 | 0 |
| Cua06 | Cirrhosis | 0 | 2.5 | 0 | 4.32 | 38.3 | 0 | 0.197 | 0 | 0.100 | 0 |
| Cua07 | Cirrhosis | 0 | 10.8 | 0 | 154 | 18.8 | 0 | 0.170 | 0 | 0.126 | 0 |
| Cua08 | Cirrhosis | 0 | 3.8 | 0 | 134 | 0.28 | 0 | 0.119 | 0 | 0.074 | 0 |
| Cua09 | Cirrhosis | 0 | 16.3 | 0 | 30 | 7.62 | 0 | 0.118 | 0 | 0.100 | 0 |
| Cua10 | Cirrhosis | 0 | 2 | 0 | 1.64 | 0 | 0 | 0.099 | 0 | 0.054 | 0 |
| Cua11 | Cirrhosis | 0 | 2.3 | 0 | 1.49 | 0.35 | 0 | 0.099 | 0 | 0.055 | 0 |
| Cua12 | Cirrhosis | 0 | 2.1 | 0 | 163 | 15.1 | 0 | 0.161 | 0 | 0.094 | 0 |
| Cua13 | Cirrhosis | 0 | 2.48 | 0 | 0.672 | 45.1 | 0 | 0.220 | 0 | 0.110 | 0 |
| Cua14 | Cirrhosis | 0 | 1.3 | 0 | 164 | 17.1 | 0 | 0.167 | 0 | 0.094 | 0 |
| Cua15 | Cirrhosis | 0 | 4.9 | 0 | 60.5 | 20.3 | 0 | 0.155 | 0 | 0.091 | 0 |
| Cua16 | Cirrhosis | 0 | 3.8 | 0 | 74.4 | 46.9 | 0 | 0.246 | 0 | 0.134 | 0 |
| Cua17 | Cirrhosis | 0 | 4 | 0 | 20.5 | 11.5 | 0 | 0.125 | 0 | 0.071 | 0 |
| Cua18 | Cirrhosis | 0 | 2.6 | 0 | 94.3 | 1.53 | 0 | 0.115 | 0 | 0.068 | 0 |
| Cua19 | Cirrhosis | 0 | 1.4 | 0 | 0.523 | 18.4 | 0 | 0.138 | 0 | 0.071 | 0 |
| Cua20 | Cirrhosis | 0 | 5.4 | 0 | 181 | 62.3 | 0 | 0.347 | 0 | 0.209 | 0 |
| Cua21 | Cirrhosis | 0 | 14.1 | 0 | 638 | 4.87 | 0 | 0.242 | 0 | 0.260 | 0 |
| Cua22 | Cirrhosis | 0 | 8.2 | 0 | 3.76 | 249 | 0 | 0.954 | 1 | 0.820 | 1 |
| Cua23 | Cirrhosis | 0 | 9.7 | 0 | 27.9 | 25.6 | 0 | 0.163 | 0 | 0.107 | 0 |
| Cua24 | Cirrhosis | 0 | 8.2 | 0 | 527 | 5.49 | 0 | 0.214 | 0 | 0.188 | 0 |
| Cua25 | Cirrhosis | 0 | 0 | 0 | 465 | 0.28 | 0 | 0.182 | 0 | 0.124 | 0 |
| Cua26 | Cirrhosis | 0 | 2.3 | 0 | 81.2 | 14.1 | 0 | 0.142 | 0 | 0.079 | 0 |
| Cua27 | Cirrhosis | 0 | 3.3 | 0 | 750 | 19.3 | 0 | 0.339 | 0 | 0.282 | 0 |
| Cua28 | Cirrhosis | 0 | 10.6 | 0 | 6.61 | 19.1 | 0 | 0.141 | 0 | 0.096 | 0 |
| Cua29 | Cirrhosis | 0 | 8.2 | 0 | 26.1 | 17.7 | 0 | 0.141 | 0 | 0.091 | 0 |
| Cua30 | Cirrhosis | 0 | 5.2 | 0 |  | 19.2 | NA | NA | NA | NA | NA |
| Cua31 | Cirrhosis | 0 | 2.5 | 0 | 0.412 | 17 | 0 | 0.135 | 0 | 0.071 | 0 |
| Cua32 | Cirrhosis | 0 | 2.87 | 0 | 0.578 | 27.5 | 0 | 0.163 | 0 | 0.085 | 0 |
| Cua33 | Cirrhosis | 0 | 4.7 | 0 | 15.1 | 49.3 | 0 | 0.239 | 0 | 0.128 | 0 |
| Cua34 | Cirrhosis | 0 | 1.77 | 0 | 0.879 | 133 | 0 | 0.641 | 1 | 0.343 | 0 |
| Cua35 | Cirrhosis | 0 | 10.2 | 0 | 344 | 10.9 | 0 | 0.188 | 0 | 0.156 | 0 |
| Cua36 | Cirrhosis | 0 |  |  | 618 | 3.08 | 0 | 0.230 | 0 |  |  |
| Cua37 | Cirrhosis | 0 | 2.49 | 0 | 118 | 0.4 | 0 | 0.116 | 0 | 0.069 | 0 |
| Cua38 | Cirrhosis | 0 | 2.3 | 0 | 92.8 | 4.32 | 0 | 0.121 | 0 | 0.070 | 0 |
| Cua39 | Cirrhosis | 0 | 1.8 | 0 | 156 | 1.52 | 0 | 0.125 | 0 | 0.074 | 0 |
| Cua40 | Cirrhosis | 0 | 5.3 | 0 | 64.4 | 0 | 0 | 0.107 | 0 | 0.068 | 0 |
| Cua41 | Cirrhosis | 0 | NA | 0 | 0.868 | 5.45 | 0 | 0.109 | 0 | NA | NA |
| Cua42 | Cirrhosis | 0 | NA | 0 | 0.656 | 6.31 | 0 | 0.111 | 0 | NA | NA |
| Cua43 | Cirrhosis | 0 | 0 | 0 | 1.13 | 14 | 0 | 0.128 | 0 | 0.063 | 0 |
| Cua44 | Cirrhosis | 0 | 5.4 | 0 | 3.73 | 36 | 0 | 0.189 | 0 | 0.105 | 0 |
| Cua45 | Cirrhosis | 0 | 4.8 | 0 | 40.6 | 0 | 0 | 0.104 | 0 | 0.064 | 0 |
| Cua46 | Cirrhosis | 0 |  |  | 10.2 | 16.4 | 0 | 0.135 | 0 | NA | NA |
| Cua47 | Cirrhosis | 0 | 0 | 0 | 58.3 | 5.62 | 0 | 0.118 | 0 | 0.062 | 0 |
| Cua48 | Cirrhosis | 0 | 3.5 | 0 | 104 | 2.54 | 0 | 0.119 | 0 | 0.072 | 0 |
| Cua49 | Cirrhosis | 0 | 2.6 | 0 | 110 | 9.61 | 0 | 0.136 | 0 | 0.079 | 0 |
| Cua50 | Cirrhosis | 0 | 4.8 | 0 | 15.8 | 0.71 | 0 | 0.102 | 0 | 0.061 | 0 |
| T01 | Hepatitis | 0 | 0 | 0 | 0.01 | 0 | 0 | 0.098 | 0 | 0.050 | 0 |
| T02 | Hepatitis | 0 | 0 | 0 | 46.2 | 0 | 0 | 0.105 | 0 | 0.055 | 0 |
| T03 | Hepatitis | 0 | 0 | 0 | 2.4 | 0 | 0 | 0.099 | 0 | 0.051 | 0 |
| T04 | Hepatitis | 0 | 0 | 0 | 25.9 | 0 | 0 | 0.102 | 0 | 0.053 | 0 |
| T05 | Hepatitis | 0 | 0 | 0 | 0 | 0 | 0 | 0.098 | 0 | 0.050 | 0 |
| T06 | Hepatitis | 0 | 0 | 0 | 14.4 | 0 | 0 | 0.100 | 0 | 0.052 | 0 |
| T07 | Hepatitis | 0 | 0 | 0 | 364 | 145 | 0 | 0.800 | 1 | 0.562 | 1 |
| T08 | Hepatitis | 0 | 0 | 0 | 0.27 | 0 | 0 | 0.098 | 0 | 0.050 | 0 |
| T09 | Hepatitis | 0 | 0 | 0 | 25.3 | 0 | 0 | 0.102 | 0 | 0.053 | 0 |
| T10 | Hepatitis | 0 | 0 | 0 | 32.3 | 0 | 0 | 0.103 | 0 | 0.054 | 0 |
| T11 | Hepatitis | 0 | 0 | 0 | 0.19 | 0 | 0 | 0.098 | 0 | 0.050 | 0 |
| T12 | Hepatitis | 0 | 0 | 0 | 10.6 | 0 | 0 | 0.100 | 0 | 0.052 | 0 |
| T13 | Hepatitis | 0 | 0 | 0 | 30.2 | 0 | 0 | 0.102 | 0 | 0.054 | 0 |
| T14 | Hepatitis | 0 | 0 | 0 | 67.6 | 0 | 0 | 0.108 | 0 | 0.058 | 0 |

TABLE 10-continued

Logistic regression of the 3-DNA marker panel for all-stage HCC:

| Code | Diagnosis | Urine-typenumeric (1= HCC, 0 = non-HCC) | AFP ng/ml) | AFP category (1 = >20, 0 = <20) | mGSTP1 (copies/ml) | mRASSF1A (copies/ml) | TP53249T (copies/ml) | JBS3 Predicted probability (based on logistic regression) | JBS3 Predicted group (cutoff = 0.5) | JBS3 + AFP Predicted probability (based on logistic regression) | JBS3 + AFP Predicted group (cutoff = 0.5) |
|---|---|---|---|---|---|---|---|---|---|---|---|
| T15 | Hepatitis | 0 | 0 | 0 | 0.02 | 0 | 0 | 0.098 | 0 | 0.050 | 0 |
| T16 | Hepatitis | 0 | 0 | 0 | 0.78 | 0 | 0 | 0.098 | 0 | 0.051 | 0 |
| T17 | Hepatitis | 0 | 0 | 0 | 0.99 | 0 | 0 | 0.098 | 0 | 0.051 | 0 |
| T18 | Hepatitis | 0 | 0 | 0 | 0 | 0 | 0 | 0.098 | 0 | 0.050 | 0 |
| T19 | Hepatitis | 0 | 0 | 0 | 17.5 | 0 | 0 | 0.101 | 0 | 0.052 | 0 |
| T20 | Hepatitis | 0 | 0 | 0 | 8.92 | 0 | 0 | 0.099 | 0 | 0.051 | 0 |
| T21 | Hepatitis | 0 | 0 | 0 | 101 | 0 | 0 | 0.113 | 0 | 0.062 | 0 |
| T22 | Hepatitis | 0 | 0 | 0 | 0 | 0 | 0 | 0.098 | 0 | 0.050 | 0 |
| T23 | Hepatitis | 0 | 0 | 0 | 1.88 | 0 | 0 | 0.099 | 0 | 0.051 | 0 |
| T24 | Hepatitis | 0 | 0 | 0 | 73.1 | 0 | 0 | 0.109 | 0 | 0.058 | 0 |
| T25 | Hepatitis | 0 | 0 | 0 | 13.9 | 0 | 0 | 0.100 | 0 | 0.052 | 0 |
| T26 | Hepatitis | 0 | 0 | 0 | 0.01 | 0 | 0 | 0.098 | 0 | 0.050 | 0 |
| T27 | Hepatitis | 0 | 0 | 0 | 18.9 | 0 | 0 | 0.101 | 0 | 0.052 | 0 |
| T28 | Hepatitis | 0 | 0 | 0 | 4.96 | 0 | 0 | 0.099 | 0 | 0.051 | 0 |
| T29 | Hepatitis | 0 | 0 | 0 | 1.71 | 0 | 0 | 0.099 | 0 | 0.051 | 0 |
| T30 | Hepatitis | 0 | 0 | 0 | 8.53 | 0 | 0 | 0.099 | 0 | 0.051 | 0 |
| T31 | Hepatitis | 0 | 0 | 0 | 3.23 | 0 | 0 | 0.099 | 0 | 0.051 | 0 |
| T32 | Hepatitis | 0 | 0 | 0 | 0.54 | 13.4 | 0 | 0.126 | 0 | 0.062 | 0 |
| T33 | Hepatitis | 0 | 0 | 0 | 0.02 | 0 | 0 | 0.098 | 0 | 0.050 | 0 |
| T34 | Hepatitis | 0 | 0 | 0 | 3.75 | 7.08 | 0 | 0.113 | 0 | 0.057 | 0 |
| T35 | Hepatitis | 0 | 0 | 0 | 0 | 0 | 0 | 0.098 | 0 | 0.050 | 0 |
| T36 | Hepatitis | 0 | 0 | 0 | 51.9 | 0 | 0 | 0.106 | 0 | 0.056 | 0 |
| T37 | Hepatitis | 0 | 0 | 0 | 5.29 | 12.7 | 0 | 0.125 | 0 | 0.062 | 0 |
| T38 | Hepatitis | 0 | 0 | 0 | 10.8 | 0 | 0 | 0.100 | 0 | 0.052 | 0 |
| T39 | Hepatitis | 0 | 0 | 0 | 1.36 | 0 | 0 | 0.098 | 0 | 0.051 | 0 |
| T40 | Hepatitis | 0 | 0 | 0 | 4.02 | 0 | 0 | 0.099 | 0 | 0.051 | 0 |
| T42 | Hepatitis | 0 | 0 | 0 | 0 | 0 | 0 | 0.098 | 0 | 0.050 | 0 |
| T43 | Hepatitis | 0 | 0 | 0 | 0 | 0 | 0 | 0.098 | 0 | 0.050 | 0 |

TABLE 11

Logistic regression of the 3-DNA marker panel for early-stage HCC

| Code | Diagnosis | Urine-typenumeric (1= HCC, 0 = non-HCC) | AFP ng/ml) | AFP category (1 = >20, 0 = <20) | mGSTP1 (copies/ml) | mRASSF1A (copies/ml) | TP53249T (copies/ml) | JBS3 Predicted probability (based on logistic regression) | JBS3 Predicted group (cutoff = 0.5) | JBS3 + AFP Predicted probability (based on logistic regression) | JBS3 + AFP Predicted group (cutoff = 0.5) |
|---|---|---|---|---|---|---|---|---|---|---|---|
| UB45b | HCC | 1 | 160.33 | 1 | 0 | 91.2 | 0 | 0.259 | 0 | 0.973 | 1 |
| UB46b | HCC | 1 | 113.81 | 1 | 0 | 130 | 44.8 | 1.000 | 1 | 1.000 | 1 |
| UB49b | HCC | 1 | 13.33 | 0 | 0 | 632.73 | 121.3 | 1.000 | 1 | 1.000 | 1 |
| UB50b | HCC | 1 | 1.75 | 0 | 0 | 54.75 | 126.8 | 1.000 | 1 | 1.000 | 1 |
| UB51b | HCC | 1 | 2.58 | 0 | 10700 | 83.06 | 31.6 | 1.000 | 1 | 1.000 | 1 |
| UB52b | HCC | 1 | 18.19 | 0 | 0 | 386.19 | 72.8 | 1.000 | 1 | 1.000 | 1 |
| UB53b | HCC | 1 | 6.45 | 0 | 0 | 68.24 | 0 | 0.183 | 0 | 0.059 | 0 |
| UB54b | HCC | 1 | 22.37 | 1 | 0 | 57.87 | 0 | 0.155 | 0 | 0.089 | 0 |
| UB55b | HCC | 1 | 288.46 | 1 | 0 | 74.15 | 0 | 0.201 | 0 | 1.000 | 1 |
| UB57b | HCC | 1 | 4.76 | 0 | 4850 | 32.39 | 0 | 0.996 | 1 | 1.000 | 1 |
| UB58b | HCC | 1 | 15160 | 1 | 0 | 53.05 | 0 | 0.144 | 0 | 1.000 | 1 |
| UB60b | HCC | 1 | 2.92 | 0 | 0 | 75.91 | 73.6 | 1.000 | 1 | 1.000 | 1 |
| UB61b | HCC | 1 | 373.89 | 1 | 0 | 50.71 | 0 | 0.138 | 0 | 1.000 | 1 |
| UB62b | HCC | 1 | 22.04 | 1 | 0 | 60.3 | 180 | 1.000 | 1 | 1.000 | 1 |
| UB63b | HCC | 1 | 32.69 | 1 | 0 | 74.51 | 35.5 | 1.000 | 1 | 1.000 | 1 |
| UB64b | HCC | 1 | 15.09 | 0 | 0 | ###### | 0 | 1.000 | 1 | 1.000 | 1 |
| UB66b | HCC | 1 | 3.8 | 0 | 0 | 74.27 | 14 | 1.000 | 1 | 1.000 | 1 |
| UB67b | HCC | 1 | 6.89 | 0 | 4920 | 68.15 | 0 | 0.998 | 1 | 1.000 | 1 |
| UB68b | HCC | 1 | 3416 | 1 | 4850 | 43.31 | 0 | 0.997 | 1 | 1.000 | 1 |
| UB70b | HCC | 1 | 192.06 | 1 | 0 | 545.45 | 0 | 1.000 | 1 | 1.000 | 1 |
| UB71b | HCC | 1 | 703.3 | 1 | 4850 | 41.08 | 0 | 0.997 | 1 | 1.000 | 1 |
| UB73b | HCC | 1 | 14.84 | 0 | 8620 | 69.08 | 0 | 1.000 | 1 | 1.000 | 1 |
| UB75b | HCC | 1 | 5.75 | 0 | 0 | 41.22 | 28.9 | 1.000 | 1 | 1.000 | 1 |
| UB79b | HCC | 1 | 147215 | 1 | 4850 | 38.58 | 13.3 | 1.000 | 1 | 1.000 | 1 |
| UB81b | HCC | 1 | 19.09 | 0 | 0 | 101.17 | 30.8 | 1.000 | 1 | 1.000 | 1 |
| UB84b | HCC | 1 | 11.73 | 0 | 4850 | 42.18 | 0 | 0.997 | 1 | 1.000 | 1 |
| UA03 | HCC | 1 | 12.68 | 0 | 15.8 | 0 | 90.9 | 1.000 | 1 | 1.000 | 1 |
| UA05 | HCC | 1 | 24302 | 1 | 275 | 246.9 | NA | NA | NA | NA | NA |

TABLE 11-continued

Logistic regression of the 3-DNA marker panel for early-stage HCC

| Code | Diagnosis | Urine-typenumeric (1= HCC, 0 = non-HCC) | AFP ng/ml | AFP category (1 = >20, 0 = <20) | mGSTP1 (copies/ml) | mRASSF1A (copies/ml) | TP53249T (copies/ml) | JBS3 Predicted probability (based on logistic regression) | JBS3 Predicted group (cutoff = 0.5) | JBS3 + AFP Predicted probability (based on logistic regression) | JBS3 + AFP Predicted group (cutoff = 0.5) |
|---|---|---|---|---|---|---|---|---|---|---|---|
| UA06 | HCC | 1 | 667.1 | 1 | 16300 | 0 | 12.8 | 1.000 | 1 | 1.000 | 1 |
| UA07 | HCC | 1 | 2.91 | 0 | 3620 | 1185 | 53 | 1.000 | 1 | 1.000 | 1 |
| UA10 | HCC | 1 | 4.68 | 0 | 2990 | 0 | 84.6 | 1.000 | 1 | 1.000 | 1 |
| UA11 | HCC | 1 | 15.09 | 0 | 4190 | 0 | 0 | 0.980 | 1 | 1.000 | 1 |
| UA17 | HCC | 1 | 820.6 | 1 | 775 | 0 | 188.8 | 1.000 | 1 | 1.000 | 1 |
| UA18 | HCC | 1 | 3.53 | 0 | 11700 | 121.2 | 553.8 | 1.000 | 1 | 1.000 | 1 |
| UA20 | HCC | 1 | 4.03 | 0 | 9.51 | 14.55 | 100.5 | 1.000 | 1 | 1.000 | 1 |
| UA21 | HCC | 1 | 6.71 | 0 | 117 | 64.5 | 0 | 0.201 | 0 | 0.077 | 0 |
| UA22 | HCC | 1 | 8.57 | 0 | 25.2 | 66.9 | 505.8 | 1.000 | 1 | 1.000 | 1 |
| UA26 | HCC | 1 | 6101 | 1 | 7.92 | 50.1 | 75.2 | 1.000 | 1 | 1.000 | 1 |
| UA29 | HCC | 1 | 219.8 | 1 | 3.45 | 0 | 0 | 0.057 | 0 | 0.988 | 1 |
| UA32 | HCC | 1 | 1607 | 1 | 2.95 | 399 | 2061.1 | 1.000 | 1 | 1.000 | 1 |
| UA34 | HCC | 1 | 270.24 | 1 | 8.9 | 0 | 144.8 | 1.000 | 1 | 1.000 | 1 |
| UA40 | HCC | 1 | 114.77 | 1 | 2.69 | 0 | 0 | 0.057 | 0 | 0.578 | 1 |
| UA45 | HCC | 1 | 8.17 | 0 | 2.92 | 0 | | | | | |
| UA51 | HCC | 1 | 3.1 | 0 | 1430 | 690 | 88.4 | 1.000 | 1 | 1.000 | 1 |
| UA52 | HCC | 1 | 6.01 | 0 | 13200 | 306 | 180 | 1.000 | 1 | 1.000 | 1 |
| UA55 | HCC | 1 | 6.88 | 0 | 0 | 36.9 | NA | NA | NA | NA | NA |
| UA59 | HCC | 1 | 1.7 | 0 | 1650 | 0 | 0 | 0.457 | 0 | 0.677 | 1 |
| UA62 | HCC | 1 | 5.61 | 0 | 7.86 | 0 | 172.5 | 1.000 | 1 | 1.000 | 1 |
| UA63 | HCC | 1 | 29.11 | 1 | ###### | 0 | 0 | 1.000 | 1 | 1.000 | 1 |
| UA64 | HCC | 1 | 40000 | 1 | 9630 | 21.72 | 52.9 | 1.000 | 1 | 1.000 | 1 |
| UA67 | HCC | 1 | 24.74 | 1 | 9.77 | 360 | 0 | 0.984 | 1 | 0.943 | 1 |
| UA68 | HCC | 1 | 4.99 | 0 | 0 | 192 | 14.2 | 1.000 | 1 | 1.000 | 1 |
| UA71 | HCC | 1 | 8.39 | 0 | 77.8 | 135.9 | 0 | 0.483 | 0 | 0.207 | 0 |
| UA73 | HCC | 1 | 147215 | 1 | 0 | 132.3 | 0 | 0.435 | 0 | 1.000 | 1 |
| UA74 | HCC | 1 | 18.27 | 0 | 1590 | 0 | 57.2 | 1.000 | 1 | 1.000 | 1 |
| Cua01 | Cirrhosis | 0 | 3.5 | 0 | 21.2 | 12.2 | 0 | 0.073 | 0 | 0.023 | 0 |
| Cua02 | Cirrhosis | 0 | 2.3 | 0 | 1.37 | 25.6 | 0 | 0.090 | 0 | 0.026 | 0 |
| Cua03 | Cirrhosis | 0 | 112.4 | 1 | 41.3 | 33.3 | 0 | 0.109 | 0 | 0.708 | 1 |
| Cua04 | Cirrhosis | 0 | 8.5 | 0 | 368 | 127 | 0 | 0.555 | 1 | 0.346 | 0 |
| Cua05 | Cirrhosis | 0 | 2.5 | 0 | 14.7 | 17.5 | 0 | 0.080 | 0 | 0.024 | 0 |
| Cua06 | Cirrhosis | 0 | 2.5 | 0 | 4.32 | 38.3 | 0 | 0.113 | 0 | 0.032 | 0 |
| Cua07 | Cirrhosis | 0 | 10.8 | 0 | 154 | 18.8 | 0 | 0.100 | 0 | 0.049 | 0 |
| Cua08 | Cirrhosis | 0 | 3.8 | 0 | 134 | 0.28 | 0 | 0.070 | 0 | 0.026 | 0 |
| Cua09 | Cirrhosis | 0 | 16.3 | 0 | 30 | 7.62 | 0 | 0.069 | 0 | 0.035 | 0 |
| Cua10 | Cirrhosis | 0 | 2 | 0 | 1.64 | 0 | 0 | 0.057 | 0 | 0.017 | 0 |
| Cua11 | Cirrhosis | 0 | 2.3 | 0 | 1.49 | 0.35 | 0 | 0.058 | 0 | 0.017 | 0 |
| Cua12 | Cirrhosis | 0 | 2.1 | 0 | 163 | 15.1 | 0 | 0.095 | 0 | 0.034 | 0 |
| Cua13 | Cirrhosis | 0 | 2.48 | 0 | 0.672 | 45.1 | 0 | 0.126 | 0 | 0.035 | 0 |
| Cua14 | Cirrhosis | 0 | 1.3 | 0 | 164 | 17.1 | 0 | 0.098 | 0 | 0.034 | 0 |
| Cua15 | Cirrhosis | 0 | 4.9 | 0 | 60.5 | 20.3 | 0 | 0.090 | 0 | 0.031 | 0 |
| Cua16 | Cirrhosis | 0 | 3.8 | 0 | 74.4 | 46.9 | 0 | 0.144 | 0 | 0.047 | 0 |
| Cua17 | Cirrhosis | 0 | 4 | 0 | 20.5 | 11.5 | 0 | 0.072 | 0 | 0.023 | 0 |
| Cua18 | Cirrhosis | 0 | 2.6 | 0 | 94.3 | 1.53 | 0 | 0.068 | 0 | 0.023 | 0 |
| Cua19 | Cirrhosis | 0 | 1.4 | 0 | 0.523 | 18.4 | 0 | 0.079 | 0 | 0.022 | 0 |
| Cua20 | Cirrhosis | 0 | 5.4 | 0 | 181 | 62.3 | 0 | 0.211 | 0 | 0.085 | 0 |
| Cua21 | Cirrhosis | 0 | 14.1 | 0 | 638 | 4.87 | 0 | 0.155 | 0 | 0.160 | 0 |
| Cua22 | Cirrhosis | 0 | 8.2 | 0 | 3.76 | 249 | 0 | 0.879 | 1 | 0.577 | 1 |
| Cua23 | Cirrhosis | 0 | 9.7 | 0 | 27.9 | 25.6 | 0 | 0.094 | 0 | 0.037 | 0 |
| Cua24 | Cirrhosis | 0 | 8.2 | 0 | 527 | 5.49 | 0 | 0.135 | 0 | 0.100 | 0 |
| Cua25 | Cirrhosis | 0 | 0 | 0 | 465 | 0.28 | 0 | 0.113 | 0 | 0.058 | 0 |
| Cua26 | Cirrhosis | 0 | 2.3 | 0 | 81.2 | 14.1 | 0 | 0.083 | 0 | 0.027 | 0 |
| Cua27 | Cirrhosis | 0 | 3.3 | 0 | 750 | 19.3 | 0 | 0.225 | 0 | 0.181 | 0 |
| Cua28 | Cirrhosis | 0 | 10.6 | 0 | 6.61 | 19.1 | 0 | 0.081 | 0 | 0.032 | 0 |
| Cua29 | Cirrhosis | 0 | 8.2 | 0 | 26.1 | 17.7 | 0 | 0.081 | 0 | 0.030 | 0 |
| Cua30 | Cirrhosis | 0 | 5.2 | 0 | NA | 19.2 | NA | NA | NA | NA | NA |
| Cua31 | Cirrhosis | 0 | 2.5 | 0 | 0.412 | 17 | 0 | 0.077 | 0 | 0.023 | 0 |
| Cua32 | Cirrhosis | 0 | 2.87 | 0 | 0.578 | 27.5 | 0 | 0.093 | 0 | 0.027 | 0 |
| Cua33 | Cirrhosis | 0 | 4.7 | 0 | 15.1 | 49.3 | 0 | 0.138 | 0 | 0.043 | 0 |
| Cua34 | Cirrhosis | 0 | 1.77 | 0 | 0.879 | 133 | 0 | 0.438 | 0 | 0.133 | 0 |
| Cua35 | Cirrhosis | 0 | 10.2 | 0 | 344 | 10.9 | 0 | 0.114 | 0 | 0.071 | 0 |
| Cua36 | Cirrhosis | 0 | NA | NA | 618 | 3.08 | 0 | 0.147 | 0 | NA | NA |
| Cua37 | Cirrhosis | 0 | 2.49 | 0 | 118 | 0.4 | 0 | 0.069 | 0 | 0.024 | 0 |
| Cua38 | Cirrhosis | 0 | 2.3 | 0 | 92.8 | 4.32 | 0 | 0.071 | 0 | 0.024 | 0 |
| Cua39 | Cirrhosis | 0 | 1.8 | 0 | 156 | 1.52 | 0 | 0.074 | 0 | 0.027 | 0 |
| Cua40 | Cirrhosis | 0 | 5.3 | 0 | 64.4 | 0 | 0 | 0.063 | 0 | 0.023 | 0 |
| Cua41 | Cirrhosis | 0 | NA | NA | 0.868 | 5.45 | 0 | 0.063 | 0 | NA | NA |
| Cua42 | Cirrhosis | 0 | NA | NA | 0.656 | 6.31 | 0 | 0.064 | 0 | NA | NA |
| Cua43 | Cirrhosis | 0 | 0 | 0 | 1.13 | 14 | 0 | 0.074 | 0 | 0.020 | 0 |
| Cua44 | Cirrhosis | 0 | 5.4 | 0 | 3.73 | 36 | 0 | 0.108 | 0 | 0.034 | 0 |

TABLE 11-continued

Logistic regression of the 3-DNA marker panel for early-stage HCC

| Code | Diagnosis | Urine-typenumeric (1= HCC, 0 = non-HCC) | AFP ng/ml) | AFP category (1 = >20, 0 = <20) | mGSTP1 (copies/ml) | mRASSF1A (copies/ml) | TP53249T (copies/ml) | JBS3 Predicted probability (based on logistic regression) | JBS3 Predicted group (cutoff = 0.5) | JBS3 + AFP Predicted probability (based on logistic regression) | JBS3 + AFP Predicted group (cutoff = 0.5) |
|---|---|---|---|---|---|---|---|---|---|---|---|
| Cua45 | Cirrhosis | 0 | 4.8 | 0 | 40.6 | 0 | 0 | 0.061 | 0 | 0.021 | 0 |
| Cua46 | Cirrhosis | 0 | NA | NA | 10.2 | 16.4 | 0 | 0.078 | 0 | NA | NA |
| Cua47 | Cirrhosis | 0 | 0 | 0 | 58.3 | 5.62 | 0 | 0.069 | 0 | 0.020 | 0 |
| Cua48 | Cirrhosis | 0 | 3.5 | 0 | 104 | 2.54 | 0 | 0.070 | 0 | 0.025 | 0 |
| Cua49 | Cirrhosis | 0 | 2.6 | 0 | 110 | 9.61 | 0 | 0.080 | 0 | 0.027 | 0 |
| Cua50 | Cirrhosis | 0 | 4.8 | 0 | 15.8 | 0.71 | 0 | 0.059 | 0 | 0.020 | 0 |
| T01 | Hepatitis | 0 | 0 | 0 | 0.01 | 0 | 0 | 0.057 | 0 | 0.015 | 0 |
| T02 | Hepatitis | 0 | 0 | 0 | 46.2 | 0 | 0 | 0.061 | 0 | 0.018 | 0 |
| T03 | Hepatitis | 0 | 0 | 0 | 2.4 | 0 | 0 | 0.057 | 0 | 0.016 | 0 |
| T04 | Hepatitis | 0 | 0 | 0 | 25.9 | 0 | 0 | 0.059 | 0 | 0.017 | 0 |
| T05 | Hepatitis | 0 | 0 | 0 | 0 | 0 | 0 | 0.057 | 0 | 0.015 | 0 |
| T06 | Hepatitis | 0 | 0 | 0 | 14.4 | 0 | 0 | 0.058 | 0 | 0.016 | 0 |
| T07 | Hepatitis | 0 | 0 | 0 | 364 | 145 | 0 | 0.637 | 1 | 0.336 | 0 |
| T08 | Hepatitis | 0 | 0 | 0 | 0.27 | 0 | 0 | 0.057 | 0 | 0.016 | 0 |
| T09 | Hepatitis | 0 | 0 | 0 | 25.3 | 0 | 0 | 0.059 | 0 | 0.017 | 0 |
| T10 | Hepatitis | 0 | 0 | 0 | 32.3 | 0 | 0 | 0.060 | 0 | 0.017 | 0 |
| T11 | Hepatitis | 0 | 0 | 0 | 0.19 | 0 | 0 | 0.057 | 0 | 0.015 | 0 |
| T12 | Hepatitis | 0 | 0 | 0 | 10.6 | 0 | 0 | 0.058 | 0 | 0.016 | 0 |
| T13 | Hepatitis | 0 | 0 | 0 | 30.2 | 0 | 0 | 0.060 | 0 | 0.017 | 0 |
| T14 | Hepatitis | 0 | 0 | 0 | 67.6 | 0 | 0 | 0.063 | 0 | 0.019 | 0 |
| T15 | Hepatitis | 0 | 0 | 0 | 0.02 | 0 | 0 | 0.057 | 0 | 0.015 | 0 |
| T16 | Hepatitis | 0 | 0 | 0 | 0.78 | 0 | 0 | 0.057 | 0 | 0.016 | 0 |
| T17 | Hepatitis | 0 | 0 | 0 | 0.99 | 0 | 0 | 0.057 | 0 | 0.016 | 0 |
| T18 | Hepatitis | 0 | 0 | 0 | 0 | 0 | 0 | 0.057 | 0 | 0.015 | 0 |
| T19 | Hepatitis | 0 | 0 | 0 | 17.5 | 0 | 0 | 0.059 | 0 | 0.016 | 0 |
| T20 | Hepatitis | 0 | 0 | 0 | 8.92 | 0 | 0 | 0.058 | 0 | 0.016 | 0 |
| T21 | Hepatitis | 0 | 0 | 0 | 101 | 0 | 0 | 0.066 | 0 | 0.021 | 0 |
| T22 | Hepatitis | 0 | 0 | 0 | 0 | 0 | 0 | 0.057 | 0 | 0.015 | 0 |
| T23 | Hepatitis | 0 | 0 | 0 | 1.88 | 0 | 0 | 0.057 | 0 | 0.016 | 0 |
| T24 | Hepatitis | 0 | 0 | 0 | 73.1 | 0 | 0 | 0.064 | 0 | 0.019 | 0 |
| T25 | Hepatitis | 0 | 0 | 0 | 13.9 | 0 | 0 | 0.058 | 0 | 0.016 | 0 |
| T26 | Hepatitis | 0 | 0 | 0 | 0.01 | 0 | 0 | 0.057 | 0 | 0.015 | 0 |
| T27 | Hepatitis | 0 | 0 | 0 | 18.9 | 0 | 0 | 0.059 | 0 | 0.016 | 0 |
| T28 | Hepatitis | 0 | 0 | 0 | 4.96 | 0 | 0 | 0.058 | 0 | 0.016 | 0 |
| T29 | Hepatitis | 0 | 0 | 0 | 1.71 | 0 | 0 | 0.057 | 0 | 0.016 | 0 |
| T30 | Hepatitis | 0 | 0 | 0 | 8.53 | 0 | 0 | 0.058 | 0 | 0.016 | 0 |
| T31 | Hepatitis | 0 | 0 | 0 | 3.23 | 0 | 0 | 0.057 | 0 | 0.016 | 0 |
| T32 | Hepatitis | 0 | 0 | 0 | 0.54 | 13.4 | 0 | 0.073 | 0 | 0.019 | 0 |
| T33 | Hepatitis | 0 | 0 | 0 | 0.02 | 0 | 0 | 0.057 | 0 | 0.015 | 0 |
| T34 | Hepatitis | 0 | 0 | 0 | 3.75 | 7.08 | 0 | 0.065 | 0 | 0.018 | 0 |
| T35 | Hepatitis | 0 | 0 | 0 | 0 | 0 | 0 | 0.057 | 0 | 0.015 | 0 |
| T36 | Hepatitis | 0 | 0 | 0 | 51.9 | 0 | 0 | 0.062 | 0 | 0.018 | 0 |
| T37 | Hepatitis | 0 | 0 | 0 | 5.29 | 12.7 | 0 | 0.072 | 0 | 0.019 | 0 |
| T38 | Hepatitis | 0 | 0 | 0 | 10.8 | 0 | 0 | 0.058 | 0 | 0.016 | 0 |
| T39 | Hepatitis | 0 | 0 | 0 | 1.36 | 0 | 0 | 0.057 | 0 | 0.016 | 0 |
| T40 | Hepatitis | 0 | 0 | 0 | 4.02 | 0 | 0 | 0.057 | 0 | 0.016 | 0 |
| T42 | Hepatitis | 0 | 0 | 0 | 0 | 0 | 0 | 0.057 | 0 | 0.015 | 0 |
| T43 | Hepatitis | 0 | 0 | 0 | 0 | 0 | 0 | 0.057 | 0 | 0.015 | 0 |

TABLE 12

Logistic regression of the 3-DNA marker panel for all-stage HCC

| Code | Diagnosis | Urine-typenumeric (1= HCC, 0 = non-HCC) | AFP ng/ml) | AFP category (1 = >20, 0 = <20) | mGSTP1 (copies/ml) | mRASSF1A (copies/ml) | TP53249T (copies/ml) | JBS3 Predicted probability (based on logistic regression) | JBS3 Predicted group (cutoff = 0.5) | JBS3 + AFP Predicted probability (based on logistic regression) | JBS3 + AFP Predicted group (cutoff = 0.5) |
|---|---|---|---|---|---|---|---|---|---|---|---|
| UB45b | HCC | 1 | 160.33 | 1 | 0 | 91.2 | 0 | 0.425 | 0 | 0.982 | 1 |
| UB46b | HCC | 1 | 113.81 | 1 | 0 | 130 | 44.8 | 1.000 | 1 | 1.000 | 1 |
| UB47b | HCC | 1 | 1.25 | 0 | 0 | 122 | 0 | 0.586 | 1 | 0.299 | 0 |
| UB48b | HCC | 1 | 27.82 | 1 | 0 | 77.2 | 0 | 0.356 | 0 | 0.331 | 0 |
| UB49b | HCC | 1 | 13.33 | 0 | 0 | 632.73 | 121.3 | 1.000 | 1 | 1.000 | 1 |
| UB50b | HCC | 1 | 1.75 | 0 | 0 | 54.75 | 126.8 | 1.000 | 1 | 1.000 | 1 |
| UB51b | HCC | 1 | 2.58 | 0 | 10700 | 83.06 | 31.6 | 1.000 | 1 | 1.000 | 1 |
| UB52b | HCC | 1 | 18.19 | 0 | 0 | 386.19 | 72.8 | 1.000 | 1 | 1.000 | 1 |

TABLE 12-continued

Logistic regression of the 3-DNA marker panel for all-stage HCC

| Code | Diagnosis | Urine-typenumeric (1= HCC, 0 = non-HCC) | AFP ng/ml | AFP category (1 = >20, 0 = <20) | mGSTP1 (copies/ml) | mRASSF1A (copies/ml) | TP53249T (copies/ml) | JBS3 Predicted probability (based on logistic regression) | JBS3 Predicted group (cutoff = 0.5) | JBS3 + AFP Predicted probability (based on logistic regression) | JBS3 + AFP Predicted group (cutoff = 0.5) |
|---|---|---|---|---|---|---|---|---|---|---|---|
| UB53b | HCC | 1 | 6.45 | 0 | 0 | 68.24 | 0 | 0.314 | 0 | 0.171 | 0 |
| UB54b | HCC | 1 | 22.37 | 1 | 0 | 57.87 | 0 | 0.269 | 0 | 0.229 | 0 |
| UB55b | HCC | 1 | 288.46 | 1 | 0 | 74.15 | 0 | 0.341 | 0 | 1.000 | 1 |
| UB56b | HCC | 1 | 231.29 | 1 | 0 | 57.5 | 0 | 0.267 | 0 | 0.997 | 1 |
| UB57b | HCC | 1 | 4.76 | 0 | 4850 | 32.39 | 0 | 0.997 | 1 | 1.000 | 1 |
| UB58b | HCC | 1 | 15160 | 1 | 0 | 53.05 | 0 | 0.249 | 0 | 1.000 | 1 |
| UB60b | HCC | 1 | 2.92 | 0 | 0 | 75.91 | 73.6 | 1.000 | 1 | 1.000 | 1 |
| UB61b | HCC | 1 | 373.89 | 1 | 0 | 50.71 | 0 | 0.240 | 0 | 1.000 | 1 |
| UB62b | HCC | 1 | 22.04 | 1 | 0 | 60.3 | 180 | 1.000 | 1 | 1.000 | 1 |
| UB63b | HCC | 1 | 32.69 | 1 | 0 | 74.51 | 35.5 | 1.000 | 1 | 1.000 | 1 |
| UB64b | HCC | 1 | 15.09 | 0 | 0 | 1008.97 | 0 | 1.000 | 1 | 1.000 | 1 |
| UB65b | HCC | 1 | 3.44 | 0 | 0 | 809.43 | 0 | 0.371 | 0 | 0.186 | 0 |
| UB66b | HCC | 1 | 3.8 | 0 | 0 | 74.27 | 14 | 1.000 | 1 | 1.000 | 1 |
| UB67b | HCC | 1 | 6.89 | 0 | 4920 | 68.15 | 0 | 0.999 | 1 | 1.000 | 1 |
| UB68b | HCC | 1 | 3416 | 1 | 4850 | 43.31 | 0 | 0.998 | 1 | 1.000 | 1 |
| UB69b | HCC | 1 | 6.65 | 0 | 0 | 79.18 | 22 | 1.000 | 1 | 1.000 | 1 |
| UB70b | HCC | 1 | 192.06 | 1 | 0 | 545.45 | 0 | 1.000 | 1 | 1.000 | 1 |
| UB71b | HCC | 1 | 703.3 | 1 | 4850 | 41.08 | 0 | 0.998 | 1 | 1.000 | 1 |
| UB72b | HCC | 1 | 5.16 | 0 | 0 | 40.15 | 0 | 0.202 | 0 | 0.110 | 0 |
| UB73b | HCC | 1 | 14.84 | 0 | 8620 | 69.08 | 0 | 1.000 | 1 | 1.000 | 1 |
| UB74b | HCC | 1 | 3.41 | 0 | 4850 | 35.31 | 0 | 0.997 | 1 | 1.000 | 1 |
| UB75b | HCC | 1 | 5.75 | 0 | 0 | 41.22 | 28.9 | 1.000 | 1 | 1.000 | 1 |
| UB76b | HCC | 1 | 0 | 0 | 6320 | 34.47 | 0 | 1.000 | 1 | 1.000 | 1 |
| UB77b | HCC | 1 | 43.71 | 1 | 4850 | 20.81 | 206.6 | 1.000 | 1 | 1.000 | 1 |
| UB78b | HCC | 1 | 2477 | 1 | 0 | 36.37 | 18 | 1.000 | 1 | 1.000 | 1 |
| UB79b | HCC | 1 | 147215 | 1 | 4850 | 38.58 | 13.3 | 1.000 | 1 | 1.000 | 1 |
| UB80b | HCC | 1 | 1.6 | 0 | 0 | 72.09 | 35.9 | 1.000 | 1 | 1.000 | 1 |
| UB81b | HCC | 1 | 19.09 | 0 | 0 | 101.17 | 30.8 | 1.000 | 1 | 1.000 | 1 |
| UB82b | HCC | 1 | 192.06 | 1 | 0 | 57.18 | 43.7 | 1.000 | 1 | 1.000 | 1 |
| UB83b | HCC | 1 | 1.81 | 0 | 0 | 57.74 | 89.6 | 1.000 | 1 | 1.000 | 1 |
| UB84b | HCC | 1 | 11.73 | 0 | 4850 | 42.18 | 0 | 0.998 | 1 | 1.000 | 1 |
| UA03 | HCC | 1 | 12.68 | 0 | 15.8 | 0 | 90.9 | 1.000 | 1 | 1.000 | 1 |
| UA05 | HCC | 1 | 24302 | 1 | 275 | 246.9 | | | | | |
| UA06 | HCC | 1 | 667.1 | 1 | 16300 | 0 | 12.8 | 1.000 | 1 | 1.000 | 1 |
| UA07 | HCC | 1 | 2.91 | 0 | 3620 | 1185 | 53 | 1.000 | 1 | 1.000 | 1 |
| UA08 | HCC | 1 | 18032 | 1 | 1110 | 115.8 | 0 | 0.871 | 1 | 1.000 | 1 |
| UA10 | HCC | 1 | 4.68 | 0 | 2990 | 0 | 84.6 | 1.000 | 1 | 1.000 | 1 |
| UA11 | HCC | 1 | 15.09 | 0 | 4190 | 0 | 0 | 0.985 | 1 | 0.998 | 1 |
| UA17 | HCC | 1 | 820.6 | 1 | 775 | 0 | 188.8 | 1.000 | 1 | 1.000 | 1 |
| UA18 | HCC | 1 | 3.53 | 0 | 11700 | 121.2 | 553.8 | 1.000 | 1 | 1.000 | 1 |
| UA19 | HCC | 1 | 6.98 | 0 | 14.2 | 3.9 | 76 | 1.000 | 1 | 1.000 | 1 |
| UA20 | HCC | 1 | 4.03 | 0 | 9.51 | 14.55 | 100.5 | 1.000 | 1 | 1.000 | 1 |
| UA21 | HCC | 1 | 6.71 | 0 | 117 | 64.5 | 0 | 0.336 | 0 | 0.200 | 0 |
| UA22 | HCC | 1 | 8.57 | 0 | 25.2 | 66.9 | 505.8 | 1.000 | 1 | 1.000 | 1 |
| UA25 | HCC | 1 | 1.78 | 0 | 3.77 | 134.1 | 41.7 | 1.000 | 1 | 1.000 | 1 |
| UA26 | HCC | 1 | 6101 | 1 | 7.92 | 50.1 | 75.2 | 1.000 | 1 | 1.000 | 1 |
| UA29 | HCC | 1 | 219.8 | 1 | 3.45 | 0 | 0 | 0.099 | 0 | 0.989 | 1 |
| UA32 | HCC | 1 | 1607 | 1 | 2.95 | 399 | 2061.1 | 1.000 | 1 | 1.000 | 1 |
| UA34 | HCC | 1 | 270.24 | 1 | 8.9 | 0 | 144.8 | 1.000 | 1 | 1.000 | 1 |
| UA40 | HCC | 1 | 114.77 | 1 | 2.69 | 0 | 0 | 0.099 | 0 | 0.720 | 1 |
| UA45 | HCC | 1 | 8.17 | 0 | 2.92 | 0 | | | | | |
| UA47 | HCC | 1 | 1.23 | 0 | 2950 | 0 | 0 | 0.907 | 1 | 0.963 | 1 |
| UA48 | HCC | 1 | 12.58 | 0 | 490 | 0 | 0 | 0.187 | 0 | 0.184 | 0 |
| UA51 | HCC | 1 | 3.1 | 0 | 1430 | 690 | 88.4 | 1.000 | 1 | 1.000 | 1 |
| UA52 | HCC | 1 | 6.01 | 0 | 13200 | 306 | 180 | 1.000 | 1 | 1.000 | 1 |
| UA55 | HCC | 1 | 6.88 | 0 | 0 | 36.9 | NA | NA | NA | NA | NA |
| UA57 | HCC | 1 | 1324 | 0 | 0 | 0 | 0 | 0.098 | 0 | 0.077 | 0 |
| UA58 | HCC | 1 | 24401 | 1 | 0.516 | 402 | NA | NA | NA | NA | NA |
| UA59 | HCC | 1 | 1.7 | 0 | 1650 | 0 | 0 | 0.574 | 1 | 0.639 | 1 |
| UA61 | HCC | 1 | 4.28 | 0 | 2500 | 0 | 214.5 | 1.000 | 1 | 1.000 | 1 |
| UA62 | HCC | 1 | 5.61 | 0 | 7.86 | 0 | 172.5 | 1.000 | 1 | 1.000 | 1 |
| UA63 | HCC | 1 | 29.11 | 1 | 2530000 | 0 | 0 | 1.000 | 1 | 1.000 | 1 |
| UA64 | HCC | 1 | 40000 | 1 | 9630 | 21.72 | 52.9 | 1.000 | 1 | 1.000 | 1 |
| UA65 | HCC | 1 | 4.97 | 0 | 11.7 | 36 | 0 | 0.191 | 0 | 09.105 | 0 |
| UA67 | HCC | 1 | 24.74 | 1 | 9.77 | 360 | 0 | 0.995 | 1 | 0.981 | 1 |
| UA68 | HCC | 1 | 4.99 | 0 | 0 | 192 | 14.2 | 1.000 | 1 | 1.000 | 1 |
| UA71 | HCC | 1 | 8.39 | 0 | 77.8 | 135.9 | 0 | 0.681 | 1 | 0.446 | 0 |
| UA72 | HCC | 1 | 60500 | 1 | 6.45 | 0 | 0 | 0.099 | 0 | 1.000 | 1 |
| UA73 | HCC | 1 | 147215 | 1 | 0 | 132.3 | 0 | 0.637 | 1 | 1.000 | 1 |
| UA74 | HCC | 1 | 18.27 | 0 | 1590 | 0 | 57.2 | 1.000 | 1 | 1.000 | 1 |
| Cua01 | Cirrhosis | 0 | 3.5 | 0 | 21.2 | 12.2 | 0 | 0.127 | 0 | 0.071 | 0 |

TABLE 12-continued

Logistic regression of the 3-DNA marker panel for all-stage HCC

| Code | Diagnosis | Urine-typenumeric (1= HCC, 0 = non-HCC) | AFP ng/ml) | AFP category (1 = >20, 0 = <20) | mGSTP1 (copies/ml) | mRASSF1A (copies/ml) | TP53249T (copies/ml) | JBS3 Predicted probability (based on logistic regression) | JBS3 Predicted group (cutoff = 0.5) | JBS3 + AFP Predicted probability (based on logistic regression) | JBS3 + AFP Predicted group (cutoff = 0.5) |
|---|---|---|---|---|---|---|---|---|---|---|---|
| Cua02 | Cirrhosis | 0 | 2.3 | 0 | 1.37 | 25.6 | 0 | 0.158 | 0 | 0.081 | 0 |
| Cua03 | Cirrhosis | 0 | 112.4 | 1 | 41.3 | 33.3 | 0 | 0.189 | 0 | 0.818 | 1 |
| Cua04 | Cirrhosis | 0 | 8.5 | 0 | 368 | 127 | 0 | 0.733 | 1 | 0.561 | 1 |
| Cua05 | Cirrhosis | 0 | 2.5 | 0 | 14.7 | 17.5 | 0 | 0.139 | 0 | 0.074 | 0 |
| Cua06 | Cirrhosis | 0 | 2.5 | 0 | 4.32 | 38.3 | 0 | 0.197 | 0 | 0.100 | 0 |
| Cua07 | Cirrhosis | 0 | 10.8 | 0 | 154 | 18.8 | 0 | 0.170 | 0 | 0.126 | 0 |
| Cua08 | Cirrhosis | 0 | 3.8 | 0 | 134 | 0.28 | 0 | 0.119 | 0 | 0.074 | 0 |
| Cua09 | Cirrhosis | 0 | 16.3 | 0 | 30 | 7.62 | 0 | 0.118 | 0 | 0.100 | 0 |
| Cua10 | Cirrhosis | 0 | 2 | 0 | 1.64 | 0 | 0 | 0.099 | 0 | 0.054 | 0 |
| Cua11 | Cirrhosis | 0 | 2.3 | 0 | 1.49 | 0.35 | 0 | 0.099 | 0 | 0.055 | 0 |
| Cua12 | Cirrhosis | 0 | 2.1 | 0 | 163 | 15.1 | 0 | 0.161 | 0 | 0.094 | 0 |
| Cua13 | Cirrhosis | 0 | 2.48 | 0 | 0.672 | 45.1 | 0 | 0.220 | 0 | 0.110 | 0 |
| Cua14 | Cirrhosis | 0 | 1.3 | 0 | 164 | 17.1 | 0 | 0.167 | 0 | 0.094 | 0 |
| Cua15 | Cirrhosis | 0 | 4.9 | 0 | 60.5 | 20.3 | 0 | 0.155 | 0 | 0.091 | 0 |
| Cua16 | Cirrhosis | 0 | 3.8 | 0 | 74.4 | 46.9 | 0 | 0.246 | 0 | 0.134 | 0 |
| Cua17 | Cirrhosis | 0 | 4 | 0 | 20.5 | 11.5 | 0 | 0.125 | 0 | 0.071 | 0 |
| Cua18 | Cirrhosis | 0 | 2.6 | 0 | 94.3 | 1.53 | 0 | 0.115 | 0 | 0.068 | 0 |
| Cua19 | Cirrhosis | 0 | 1.4 | 0 | 0.523 | 18.4 | 0 | 0.138 | 0 | 0.071 | 0 |
| Cua20 | Cirrhosis | 0 | 5.4 | 0 | 181 | 62.3 | 0 | 0.347 | 0 | 0.209 | 0 |
| Cua21 | Cirrhosis | 0 | 14.1 | 0 | 638 | 4.87 | 0 | 0.242 | 0 | 0.260 | 0 |
| Cua22 | Cirrhosis | 0 | 8.2 | 0 | 3.76 | 249 | 0 | 0.954 | 1 | 0.820 | 1 |
| Cua23 | Cirrhosis | 0 | 9.7 | 0 | 27.9 | 25.6 | 0 | 0.163 | 0 | 0.107 | 0 |
| Cua24 | Cirrhosis | 0 | 8.2 | 0 | 527 | 5.49 | 0 | 0.214 | 0 | 0.188 | 0 |
| Cua25 | Cirrhosis | 0 | 0 | 0 | 465 | 0.28 | 0 | 0.182 | 0 | 0.124 | 0 |
| Cua26 | Cirrhosis | 0 | 2.3 | 0 | 81.2 | 14.1 | 0 | 0.142 | 0 | 0.079 | 0 |
| Cua27 | Cirrhosis | 0 | 3.3 | 0 | 750 | 19.3 | 0 | 0.339 | 0 | 0.282 | 0 |
| Cua28 | Cirrhosis | 0 | 10.6 | 0 | 6.61 | 19.1 | 0 | 0.141 | 0 | 0.096 | 0 |
| Cua29 | Cirrhosis | 0 | 8.2 | 0 | 26.1 | 17.7 | 0 | 0.141 | 0 | 0.091 | 0 |
| Cua30 | Cirrhosis | 0 | 5.2 | 0 |  | 19.2 | NA | NA | NA | NA | NA |
| Cua31 | Cirrhosis | 0 | 2.5 | 0 | 0.412 | 17 | 0 | 0.135 | 0 | 0.071 | 0 |
| Cua32 | Cirrhosis | 0 | 2.87 | 0 | 0.578 | 27.5 | 0 | 0.163 | 0 | 0.085 | 0 |
| Cua33 | Cirrhosis | 0 | 4.7 | 0 | 15.1 | 49.3 | 0 | 0.239 | 0 | 0.128 | 0 |
| Cua34 | Cirrhosis | 0 | 1.77 | 0 | 0.879 | 133 | 0 | 0.641 | 1 | 0.343 | 0 |
| Cua35 | Cirrhosis | 0 | 10.2 | 0 | 344 | 10.9 | 0 | 0.188 | 0 | 0.156 | 0 |
| Cua36 | Cirrhosis | 0 |  |  | 618 | 3.08 | 0 | 0.230 | 0 |  |  |
| Cua37 | Cirrhosis | 0 | 2.49 | 0 | 118 | 0.4 | 0 | 0.116 | 0 | 0.069 | 0 |
| Cua38 | Cirrhosis | 0 | 2.3 | 0 | 92.8 | 4.32 | 0 | 0.121 | 0 | 0.070 | 0 |
| Cua39 | Cirrhosis | 0 | 1.8 | 0 | 156 | 1.52 | 0 | 0.125 | 0 | 0.074 | 0 |
| Cua40 | Cirrhosis | 0 | 5.3 | 0 | 64.4 | 0 | 0 | 0.107 | 0 | 0.068 | 0 |
| Cua41 | Cirrhosis | 0 | NA | 0 | 0.868 | 5.45 | 0 | 0.109 | 0 | NA | NA |
| Cua42 | Cirrhosis | 0 | NA | 0 | 0.656 | 6.31 | 0 | 0.111 | 0 | NA | NA |
| Cua43 | Cirrhosis | 0 | 0 | 0 | 1.13 | 14 | 0 | 0.128 | 0 | 0.063 | 0 |
| Cua44 | Cirrhosis | 0 | 5.4 | 0 | 3.73 | 36 | 0 | 0.189 | 0 | 0.105 | 0 |
| Cua45 | Cirrhosis | 0 | 4.8 | 0 | 40.6 | 0 | 0 | 0.104 | 0 | 0.064 | 0 |
| Cua46 | Cirrhosis | 0 |  |  | 10.2 | 16.4 | 0 | 0.135 | 0 | NA | NA |
| Cua47 | Cirrhosis | 0 | 0 | 0 | 58.3 | 5.62 | 0 | 0.118 | 0 | 0.062 | 0 |
| Cua48 | Cirrhosis | 0 | 3.5 | 0 | 104 | 2.54 | 0 | 0.119 | 0 | 0.072 | 0 |
| Cua49 | Cirrhosis | 0 | 2.6 | 0 | 110 | 9.61 | 0 | 0.136 | 0 | 0.079 | 0 |
| Cua50 | Cirrhosis | 0 | 4.8 | 0 | 15.8 | 0.71 | 0 | 0.102 | 0 | 0.061 | 0 |
| T01 | Hepatitis | 0 | 0 | 0 | 0.01 | 0 | 0 | 0.098 | 0 | 0.050 | 0 |
| T02 | Hepatitis | 0 | 0 | 0 | 46.2 | 0 | 0 | 0.105 | 0 | 0.055 | 0 |
| T03 | Hepatitis | 0 | 0 | 0 | 2.4 | 0 | 0 | 0.099 | 0 | 0.051 | 0 |
| T04 | Hepatitis | 0 | 0 | 0 | 25.9 | 0 | 0 | 0.102 | 0 | 0.053 | 0 |
| T05 | Hepatitis | 0 | 0 | 0 | 0 | 0 | 0 | 0.098 | 0 | 0.050 | 0 |
| T06 | Hepatitis | 0 | 0 | 0 | 14.4 | 0 | 0 | 0.100 | 0 | 0.052 | 0 |
| T07 | Hepatitis | 0 | 0 | 0 | 364 | 145 | 0 | 0.800 | 1 | 0.562 | 1 |
| T08 | Hepatitis | 0 | 0 | 0 | 0.27 | 0 | 0 | 0.098 | 0 | 0.050 | 0 |
| T09 | Hepatitis | 0 | 0 | 0 | 25.3 | 0 | 0 | 0.102 | 0 | 0.053 | 0 |
| T10 | Hepatitis | 0 | 0 | 0 | 32.3 | 0 | 0 | 0.103 | 0 | 0.054 | 0 |
| T11 | Hepatitis | 0 | 0 | 0 | 0.19 | 0 | 0 | 0.098 | 0 | 0.050 | 0 |
| T12 | Hepatitis | 0 | 0 | 0 | 10.6 | 0 | 0 | 0.100 | 0 | 0.052 | 0 |
| T13 | Hepatitis | 0 | 0 | 0 | 30.2 | 0 | 0 | 0.102 | 0 | 0.054 | 0 |
| T14 | Hepatitis | 0 | 0 | 0 | 67.6 | 0 | 0 | 0.108 | 0 | 0.058 | 0 |
| T15 | Hepatitis | 0 | 0 | 0 | 0.02 | 0 | 0 | 0.098 | 0 | 0.050 | 0 |
| T16 | Hepatitis | 0 | 0 | 0 | 0.78 | 0 | 0 | 0.098 | 0 | 0.051 | 0 |
| T17 | Hepatitis | 0 | 0 | 0 | 0.99 | 0 | 0 | 0.098 | 0 | 0.051 | 0 |
| T18 | Hepatitis | 0 | 0 | 0 | 0 | 0 | 0 | 0.098 | 0 | 0.050 | 0 |
| T19 | Hepatitis | 0 | 0 | 0 | 17.5 | 0 | 0 | 0.101 | 0 | 0.052 | 0 |
| T20 | Hepatitis | 0 | 0 | 0 | 8.92 | 0 | 0 | 0.099 | 0 | 0.051 | 0 |
| T21 | Hepatitis | 0 | 0 | 0 | 101 | 0 | 0 | 0.113 | 0 | 0.062 | 0 |
| T22 | Hepatitis | 0 | 0 | 0 | 0 | 0 | 0 | 0.098 | 0 | 0.050 | 0 |

TABLE 12-continued

Logistic regression of the 3-DNA marker panel for all-stage HCC

| Code | Diagnosis | Urine-typenumeric (1= HCC, 0 = non-HCC) | AFP ng/ml | AFP category (1 = >20, 0 = <20) | mGSTP1 (copies/ml) | mRASSF1A (copies/ml) | TP53249T (copies/ml) | JBS3 Predicted probability (based on logistic regression) | JBS3 Predicted group (cutoff = 0.5) | JBS3 + AFP Predicted probability (based on logistic regression) | JBS3 + AFP Predicted group (cutoff = 0.5) |
|---|---|---|---|---|---|---|---|---|---|---|---|
| T23 | Hepatitis | 0 | 0 | 0 | 1.88 | 0 | 0 | 0.099 | 0 | 0.051 | 0 |
| T24 | Hepatitis | 0 | 0 | 0 | 73.1 | 0 | 0 | 0.109 | 0 | 0.058 | 0 |
| T25 | Hepatitis | 0 | 0 | 0 | 13.9 | 0 | 0 | 0.100 | 0 | 0.052 | 0 |
| T26 | Hepatitis | 0 | 0 | 0 | 0.01 | 0 | 0 | 0.098 | 0 | 0.050 | 0 |
| T27 | Hepatitis | 0 | 0 | 0 | 18.9 | 0 | 0 | 0.101 | 0 | 0.052 | 0 |
| T28 | Hepatitis | 0 | 0 | 0 | 4.96 | 0 | 0 | 0.099 | 0 | 0.051 | 0 |
| T29 | Hepatitis | 0 | 0 | 0 | 1.71 | 0 | 0 | 0.099 | 0 | 0.051 | 0 |
| T30 | Hepatitis | 0 | 0 | 0 | 8.53 | 0 | 0 | 0.099 | 0 | 0.051 | 0 |
| T31 | Hepatitis | 0 | 0 | 0 | 3.23 | 0 | 0 | 0.099 | 0 | 0.051 | 0 |
| T32 | Hepatitis | 0 | 0 | 0 | 0.54 | 13.4 | 0 | 0.126 | 0 | 0.062 | 0 |
| T33 | Hepatitis | 0 | 0 | 0 | 0.02 | 0 | 0 | 0.098 | 0 | 0.050 | 0 |
| T34 | Hepatitis | 0 | 0 | 0 | 3.75 | 7.08 | 0 | 0.113 | 0 | 0.057 | 0 |
| T35 | Hepatitis | 0 | 0 | 0 | 0 | 0 | 0 | 0.098 | 0 | 0.050 | 0 |
| T36 | Hepatitis | 0 | 0 | 0 | 51.9 | 0 | 0 | 0.106 | 0 | 0.056 | 0 |
| T37 | Hepatitis | 0 | 0 | 0 | 5.29 | 12.7 | 0 | 0.125 | 0 | 0.062 | 0 |
| T38 | Hepatitis | 0 | 0 | 0 | 10.8 | 0 | 0 | 0.100 | 0 | 0.052 | 0 |
| T39 | Hepatitis | 0 | 0 | 0 | 1.36 | 0 | 0 | 0.098 | 0 | 0.051 | 0 |
| T40 | Hepatitis | 0 | 0 | 0 | 4.02 | 0 | 0 | 0.099 | 0 | 0.051 | 0 |
| T42 | Hepatitis | 0 | 0 | 0 | 0 | 0 | 0 | 0.098 | 0 | 0.050 | 0 |
| T43 | Hepatitis | 0 | 0 | 0 | 0 | 0 | 0 | 0.098 | 0 | 0.050 | 0 |

All references cited in this application are incorporated by reference into this application in their entireties.

REFERENCES CITED

1. Simard, E. P., et al., *Cancers with increasing incidence trends in the United States: 1999 through 2008.* CA: A Cancer Journal for Clinicians, 2012. 62(2): p. 118-128.
2. Jain, S., et al., *Methylation of the CpG Sites Only on the Sense Strand of the <italic>APC</italic> Gene Is Specific for Hepatocellular Carcinoma.* PLoS ONE, 2011. 6(11): p. e26799.
3. Bruix, J. and M. Sherman, *Management of hepatocellular carcinoma.* Hepatology, 2005. 42(5): p. 1208-1236.
4. Nomoto, S., T. Kinoshita, and K. Kato, *Hypermethylation of multiple genes as clonal markers in multicentric hepatocellular carcinoma.* Br J Cancer, 2007. 97(9): p. 1260, 1265.
5. Hanahan, D. and R. A. Weinberg, *The Hallmarks of Cancer.* Cell, 2000. 100(1): p. 57-70.
6. Whittaker, S., R. Marais, and A. X. Zhu, *The role of signaling pathways in the development and treatment of hepatocellular carcinoma.* Oncogene, 2010. 29(36): p. 4989-5005.
7. Boyault, S., et al., *Transcriptome classification of HCC is related to gene alterations and to new therapeutic targets.* Hepatology, 2007. 45 p. 42-45.
8. Bressac, B., et al., *Selective G to T mutations of p53 gene in hepatocellular carcinoma from southern Africa.* Nature, 1991. 350: p. 429-431.
9. Hayashi, H., et al., *The clinical significance of p53 gene mutation in hepatocellular carcinomas from Japan.* Hepatology, 1995. 22(6): p. 1702, 1707.
10. Honda, K., E. SbisÀ, and A. Tullo, *p53 mutation is a poor prognostic indicator for survival in patients with hepatocellular carcinoma undergoing surgical tumour ablation.* Br J Cancer, 1998. 77(5): p. 776, 782.
11. Hussain, S. P., et al., *TP53 mutations and hepatocellular carcinoma: insights into the etiology and pathogenesis of liver cancer.* Oncogene, 2007. 26(15): p. 2166, 2176.
12. Laurent-Puig, P., et al., *Genetic alterations associated with hepatocellular carcinomas define distinct pathways of hepatocarcinogenesis.* Gastroenterology, 2001. 120: p. 1763-1773.
13. Cieply, B., et al., *Unique phenotype of hepatocellular cancers with exon-3 mutations in beta-catenin gene.* Hepatology, 2009. 49(3): p. 821, 831.
14. de La Coste, A., B. Romagnolo, and P. Billuart, *Somatic mutations of the beta-catenin gene are frequent in mouse and human hepatocellular carcinomas.* Proc Natl Acad Sci USA, 1998. 95(15): p. 8847, 8851.
15. Huang, H., H. Fujii, and A. Sankila, *Beta-catenin mutations are frequent in human hepatocellular carcinomas associated with hepatitis C virus infection.* Am J Pathol, 1999. 155(6): p. 1795, 1801.
16. Legoix, P., O. Bluteau, and J. Bayer, *Beta-catenin mutations in hepatocellular carcinoma correlate with a low rate of loss of heterozygosity.* Oncogene, 1999. 18(27): p. 4044, 4046.
17. Miyoshi, Y., K. Iwao, and Y. Nagasawa, *Activation of the beta-catenin gene in primary hepatocellular carcinomas by somatic alterations involving exon 3.* Cancer Res, 1998. 58(12): p. 2524, 2527.
18. Taniguchi, K., L. R. Roberts, and I. N. Aderca, *Mutational spectrum of beta-catenin, AXIN1, and AXIN2 in hepatocellular carcinomas and hepatoblastomas.* Oncogene, 2002. 21(31): p. 4863, 4871.
19. Terris, B., P. Pineau, and L. Bregeaud, *Close correlation between beta-catenin gene alterations and nuclear accumulation of the protein in human hepatocellular carcinomas.* Oncogene, 1999. 18(47): p. 6583, 6588.
20. Wong, C. M., S. T. Fan, and I. O. Ng, *Beta-catenin mutation and overexpression in hepatocellular carcinoma: clinicopathologic and prognostic significance.* Cancer, 2001. 92(1): p. 136, 145.
21. Hu, L., et al., *Clinicopathological significance of RASSF1A reduced expression and hypermethylation in hepatocellular carcinoma.* Hepatology International. 4(1): p. 423-432.

22. Newell, P., et al., *Ras pathway activation in hepatocellular carcinoma and anti-tumoral effect of combined sorafenib and rapamycin in vivo*. Journal of Hepatology, 2009. 51(4): p. 725-733.
23. Oh, B. K., H. Kim, and H. J. Park, *DNA methyltransferase expression and DNA methylation in human hepatocellular carcinoma and their clinicopathological correlation*. Int J Mol Med, 2007. 20(1): p. 65, 73.
24. Yu, J., et al., *Methylation profiling of twenty promoter-CpG islands of genes which may contribute to hepatocellular carcinogenesis*. BMC Cancer, 2002. 2: p. 29-43.
25. Calvisi, D. F., S. Ladu, and A. Gorden, *Ubiquitous activation of Ras and Jak/Stat pathways in human HCC*. Gastroenterology, 2006. 130(4): p. 1117, 1128.
26. Nishida, N., et al., *Aberrant methylation of multiple tumor suppressor genes in aging liver, chronic hepatitis, and hepatocellular carcinoma*. Hepatology, 2008. 47: p. 908-918.
27. Kondo, Y., L. Shen, and S. Suzuki, *Alterations of DNA methylation and histone modifications contribute to gene silencing in hepatocellular carcinomas*. Hepatol Res, 2007. 37(11): p. 974, 983.
28. Zhang, C., et al., *CpG Island Methylator Phenotype Association with Elevated Serum alpha-Fetoprotein Level in Hepatocellular Carcinoma*. Clinical Cancer Research, 2007. 13(3): p. 944-952.
29. Harder, J., et al., *Quantitative promoter methylation analysis of hepatocellular carcinoma, cirrhotic and normal liver*. International Journal of Cancer, 2008. 122(12): p. 2800-2804.
30. Yang, B., et al., *Aberrant Promoter Methylation Profiles of Tumor Suppressor Genes in Hepatocellular Carcinoma*. American Journal of Pathology, 2003. 163(3): p. 1101-1107.
31. Yu, J., et al., *Methylation profiling of twenty promoter-CpG islands of genes which may contribute to hepatocellular carcinogenesis*. BMC Cancer, 2002. 2(1): p. 29.
32. Oh, B. K., et al., *DNA methyltransferase expression and DNA methylation in human hepatocellular carcinoma and their clinicopathological correlation*. International journal of molecular medicine, 2007. 20(1): p. 65-73.
33. Kondo, Y., *Genetic instability and abberrant DNA methylation in chronic hepotitis and cirrhosis—A comprehensive study of loss of heterozygosity and microsatellite instability at 39 loci and DNA hypermethylation on 8 CpG islands in microdissected specimens from patients with hepatocellular carcinoma*. Hepatology, 2000. 32: p. 970-979.
34. Shiraz, O. B. G., Hamid•Yavarian, Majid•Geramizadeh, Bita, *Possible down regulation of the p16 gene promoter in individuals with hepatocellular carcinoma*. Hepatitis Monthly, 2011. 11(9): p. 719-723.
35. Moribe, T., et al., *Methylation of multiple genes as molecular markers for diagnosis of a small, well-differentiated hepatocellular carcinoma*. Int. J. Cancer, 2009. 125: p. 388-397.
36. Takagi, H., et al., *Frequent epigenetic inactivation of SFRP genes in hepatocellular carcinoma*. Journal of Gastroenterology, 2008. 43(5): p. 378-389.
37. Huang, J., et al., *Down-regulation of SFRP1 as a putative tumor suppressor gene can contribute to human hepatocellular carcinoma*. BMC Cancer, 2007. 7(1): p. 126.
38. Feng, Q., et al., *DNA methylation changes in normal liver tissues and hepatocellular carcinoma with different viral infection*. Experimental and Molecular Pathology, 2010. 88(2): p. 287-292.
39. Y. Wu, J. L., C. Y. Sun, Y. Zhou, Y. F. Zhao, S. J. Zhang, *Epigenetic inactivation of the canonical wnt antagonist secreted frizzled-related protein 1 in hepatocellular carcinoma cells*. Neoplasma, 2012. 59(3): p. 326-332.
40. Toyota, M., H. Suzuki, and Y. Shinomura, *The epigenome of colorectal cancer*. Current Colorectal Cancer Reports, 2009. 5(2): p. 84-89.
41. Zhong, S., et al., *Silencing of GSTP1 Gene by CpG Island DNA Hypermethylation in HBV-associated Hepatocellular Carcinomas*. Clinical Cancer Research, 2002. 8(4): p. 1087-1092.
42. Lambert, M.-P., et al., *Aberrant DNA methylation distinguishes hepatocellular carcinoma associated with HBV and HCV infection and alcohol intake*. Journal of Hepatology, 2011. 54(4): p. 705-715.
43. Jain, S., et al., *Impact of the Location of CpG Methylation within the <italic>GSTP1</italic> Gene on Its Specificity as a DNA Marker for Hepatocellular Carcinoma*. PLoS ONE, 2012. 7(4): p. e35789.
44. Chan, K. C. A., et al., *Quantitative Analysis of Circulating Methylated DNA as a Biomarker for Hepatocellular Carcinoma*. Clin Chem, 2008. 54(9): p. 1528-1536.
45. Di Gioia, S., et al., *Quantitative evaluation of RASSF1A methylation in the non-lesional, regenerative and neoplastic liver*. BMC Cancer, 2006. 6(1): p. 89.
46. Yeo, W., et al., *High frequency of promoter hypermethylation of RASSF1A in tumor and plasma of patients with hepatocellular carcinoma*. Liver International, 2005. 25(2): p. 266-272.
47. Marilyn Gordon, S. B., *RASSF1A: Not a prototypical Ras effector*. Small GTPases, 2011. 2(3): p. 148-157.
48. Su, Y. H., et al., *Human urine contains small, 150 to 250 nucleotide-sized, soluble DNA derived from the circulation and may be useful in the detection of colorectal cancer*. Journal of Molecular Diagnostics, 2004. 6(2): p. 101-107.
49. Su, Y.-H., et al., *Removal of high molecular weight DNA by carboxylated magnetic beads enhances the detection of mutated K-ras DNA in urine*. Annals of the New York Academy of Sciences, 2008. 1137: p. 82-91.
50. Su, Y.-H., et al., *Detection of K-ras mutation in urine of patients with colorectal cancer*. Cancer Biomarkers, 2005. 1: p. 177-182.
51. Song, B. P., et al., *Detection of Hypermethylated Vimentin in Urine of Patients with Colorectal Cancer*. Journal of Molecular Diagnostics, 2012. 14(2): p. in press.
52. Lin, S. Y., et al., *A locked nucleic acid clamp-mediated PCR assay for detection of a p53 codon 249 hotspot mutation in urine*. Journal of Molecular Diagnostics, 2011. 13(5): p. 474-484.
53. Abner, C. W. and P. J. McKinnon, *The DNA double-strand break response in the nervous system*. DNA Repair, 2004. 3(8-9): p. 1141-1147.
54. Yan, P. S., et al., *Differential Distribution of DNA Methylation within the RASSF1A CpG Island in Breast Cancer*. Cancer Research, 2003. 63(19): p. 6178-6186.
55. Chan, K. C. A., et al., *Quantitative Analysis of Circulating Methylated DNA as a Biomarker for Hepatocellular Carcinoma*. Clinical Chemistry, 2008. 54(9): p. 1528-1536.
56. Wong, I. H. N., et al., *Quantitative Analysis of Tumor-derived Methylated p16INK4a Sequences in Plasma, Serum, and Blood Cells of Hepatocellular Carcinoma Patients*. Clinical Cancer Research, 2003. 9(3): p. 1047-1052.

57. Tsutsui, M., et al., *Methylated cyclin D2 gene circulating in the blood as a prognosis predictor of hepatocellular carcinoma*. Clinica Chimica Acta, 2010. 411(7-8): p. 516-520.
58. Kirk, G. D., et al., *249ser TP53 mutation in plasma DNA, hepatitis B viral infection, and risk of hepatocellular carcinoma*. Oncogene, 2005. 24(38): p. 5858-5867.
59. Melkonyan, H. S., et al., *Transrenal nucleic acids: from proof of principle to clinical tests; problems and solutions*. Annals of the New York Academy of Sciences, 2008. 1137: p. 73-81.
60. Shekhtman, E. M., et al., *Optimization of transrenal DNA analysis: detection of fetal DNA in maternal urine*. Clin Chem, 2009. 55(4): p. 723-729.
61. Serdyuk, O. I., et al., *Detection of mutant k-ras sequences in the urine of cancer patients*. Bull. Exp. Biol. Med., 2001. 131: p. 283-284.
62. Chan, A. K. C., R. W. K. Chiu, and Y. M. D. Lo, *Cell-free nucleic acids in plasma, serum and urine: a new tool in molecular diagnosis*. Ann Clin Biochem, 2003. 40: p. 122-130.
63. Botezatu, I., et al., *Genetic analysis of DNA excreted in Urine: A new approach for detecting specific genomic DNA sequences from cells dying in an organism*. Clinical Chemistry, 2000. 46: p. 1078-1084.
64. Lichtenstein, A. V., et al., *Circulating nucleic acids and apoptosis*. Annals of the New York Academy of Sciences, 2001. 945: p. 239-249.
65. Jahr, S., et al., *DNA fragments in the blood plasma of cancer patients: quantitations and evidence for their origin from apoptotic and necrotic cells*. Cancer Research, 2001. 61: p. 1659-1665.
66. Su, Y.-H., et al., *Detection of mutated K-ras DNA in urine, plasma and serum from patients with colorectal carcinoma or adenomatous polyps*. Annals of the New York Academy of Sciences, 2008. 1137: p. 197-201.
67. Sikora, A., et al., *Detection of increased amounts of cell-free fetal DNA with short PCR amplicons*. Clinical Chemistry 2010. 56 (1): p. 136-138.

---

What is claimed is:

1. A method of detecting the presence or absence of hepatocellular carcinoma (HCC) in a subject in need thereof, comprising:
   (1) preparing a DNA sample from a urine sample of the subject;
   (2) determining a level of methylation of RASSF1A from the DNA sample of the subject by a two-step short-amplicon methylation specific PCR (shMSP), wherein the two-step short-amplicon methylation specific PCR (shMSP) uses primers of the nucleotide sequences as set forth in SEQ ID NO: 15 and SEQ ID NO:16 for a first step PCR and SEQ ID NO:17 and SEQ ID NO:18 for a second step PCR;
   (3) comparing the level of methylation of RASSF1A with a level of methylation of RASSF1A in one or more control samples from subjects known not to have HCC; and
   (4) detecting the presence or absence of HCC, with elevated methylation levels in RASSF1A of the individual as compared to the level of methylation in RASSF1A in the one or more control samples indicating the presence of HCC, and the absence of elevated methylation levels indicating the absence of HCC.

2. The method of claim 1, wherein the level of methylation is deemed elevated when number of copies of methylated RASSF1A (mRASSF1A) is greater than 50 copies per milliliter of urine.

3. A method of determining a probability of hepatocellular carcinoma (HCC) for a subject in need thereof, comprising:
   (1) preparing a DNA sample from a urine sample of the subject;
   (2) determining a level of mutation of TP53, a level of methylation of one or more regulatory regions of RASSF1A and a level of methylation of one or more regulatory regions of GSTP1 from the DNA sample of the subject, wherein
      the level of methylation of one or more regulatory regions of RASSF1A is determined by two-step short-amplicon methylation specific PCR (shMSP) over RASSF1A, wherein the shMSP over RASSF1A uses primers of the nucleotide sequences as set forth in SEQ ID NO: 15 and SEQ ID NO:16 for a first step PCR over RASSF1A and SEQ ID NO:17 and SEQ ID NO:18 for a second step PCR over RASSF1A; or
      the level of methylation of one or more regulatory regions of GSTP1 is determined by two-step short-amplicon methylation specific PCR (shMSP) over SEQ ID NO: 29, wherein the shMSP uses primers of the nucleotide sequences as set forth in SEQ ID NO:19 and SEQ ID NO:20 for a first step PCR and in SEQ ID NO:21, SEQ ID NO:22 and SEQ ID NO:23 for a second step PCR reaction;
   (3) calculating the probability of HCC by logistic regression modeling based on predictor variables comprising the level of mutation of TP53, the level of methylation of RASSF1A and the level of methylation of GSTP1 from the DNA sample of the subject.

4. The method of claim 3, wherein the level of mutation of TP53 is number of copies of mutated TP53 per milliliter of urine; the level of methylation of one or more regulatory regions of RASSF1A is number of copies of methylated RASSF1A per milliliter of urine; and the level of methylation of one or more regulatory regions of GSTP1 is number of copies of methylated GSTP1 per milliliter of urine.

5. The method of claim 4, wherein the logistic regression modeling further comprises a fourth predictor variable, wherein the fourth predictor variable is 1 when concentration of alpha-fetoprotein (AFP) in the urine sample of the subject is above 20 ng/ml, and the fourth variable is 0 when the AFP concentration in the urine sample of the subject is below 20 ng/ml.

6. A method for identifying and quantifying at least one nucleic acid sequence from a biological sample of a subject, comprising:
   (1) isolating the at least one nucleic acid sequence from the biological sample;
   (2) amplifying the at least one nucleic acid sequence with primers of the nucleotide sequences as set forth in SEQ ID NO: 24 and SEQ ID NO: 25 for a first step PCR;
   (3) contacting one or more LNA clamps of the nucleotide sequences as set forth in SEQ ID NO: 27 with the at least one nucleic acid sequence, wherein the one or more LNA clamps correspond to wildtype allele of the at least one nucleic acid sequence and thereby prevents amplification of wildtype sequence but not non-wildtype sequence;

(4) amplifying the at least one nucleic acid sequence with primers of the nucleotide sequences as set forth in SEQ ID NO: 24 and SEQ ID NO: 26 for a second step PCR;

(5) performing a melting curve analysis with a probe specific to the non-wildtype sequence; and (6) identifying and quantifying the at least one nucleic acid sequence.

7. The method claim of 6, wherein the biological sample comprises tissue or body fluid wherein the tissue or body fluid is selected from the group consisting of serum, plasma, and urine, wherein the LNA clamp comprises a methylene bridge connecting a 2'-oxygen and 4'-carbon (locked nucleic acid (LNA) clamp) in the wildtype nucleic acid sequence.

* * * * *

UNITED STATES PATENT AND TRADEMARK OFFICE
CERTIFICATE OF CORRECTION

PATENT NO. : 9,598,735 B2  
APPLICATION NO. : 14/079649  
DATED : March 21, 2017  
INVENTOR(S) : Wei Song et al.

Page 1 of 1

It is certified that error appears in the above-identified patent and that said Letters Patent is hereby corrected as shown below:

In the Specification

Column 1, Line 13, replace "FUNDING" with --SUPPORT--;

Column 1, Lines 15-17, replace the whole paragraph, which reads "This work was funded in part by the grants from the National Cancer Institute (R43 CA165312 and and 2R44CA165312-02).", with the paragraph --This invention was made with government support under R43CA165312 and R44CA165312 awarded by the National Institute of Health. The government has certain rights in the invention.--.

Signed and Sealed this  
Sixth Day of June, 2017

Michelle K. Lee  
*Director of the United States Patent and Trademark Office*

SEQUENCE LISTING

<160> NUMBER OF SEQ ID NOS: 29

<210> SEQ ID NO 1
<211> LENGTH: 21
<212> TYPE: DNA
<213> ORGANISM: Homo sapiens

<400> SEQUENCE: 1
gtaggttaag tgtgttgttt t                                           21

<210> SEQ ID NO 2
<211> LENGTH: 20
<212> TYPE: DNA
<213> ORGANISM: Homo sapiens

<400> SEQUENCE: 2
ttacccttcc ttccctcctt                                             20

<210> SEQ ID NO 3
<211> LENGTH: 20
<212> TYPE: DNA
<213> ORGANISM: Homo sapiens

<400> SEQUENCE: 3
aggagggaag gaagggtaag                                             20

<210> SEQ ID NO 4
<211> LENGTH: 20
<212> TYPE: DNA
<213> ORGANISM: Homo sapiens

<400> SEQUENCE: 4
taactttaaa cgctaacaaa                                             20

<210> SEQ ID NO 5
<211> LENGTH: 24
<212> TYPE: DNA
<213> ORGANISM: Homo sapiens

<400> SEQUENCE: 5
aagtcggggt tcgttttgtg gttt                                        24

-continued

```
<210> SEQ ID NO 6
<211> LENGTH: 24
<212> TYPE: DNA
<213> ORGANISM: Homo sapiens

<400> SEQUENCE: 6 cccccaaataa aatcgccaca aaaa                                              24

<210> SEQ ID NO 7
<211> LENGTH: 20
<212> TYPE: DNA
<213> ORGANISM: Homo sapiens

<400> SEQUENCE: 7
agaaatacgg gtattttcgc                                                    20

<210> SEQ ID NO 8
<211> LENGTH: 18
<212> TYPE: DNA
<213> ORGANISM: Homo sapiens

<400> SEQUENCE: 8
caccccgaac gaccacaa                                                      18

<210> SEQ ID NO 9
<211> LENGTH: 20
<212> TYPE: DNA
<213> ORGANISM: Homo sapiens

<400> SEQUENCE: 9
accacaacga cgacgaccgc                                                    20

<210> SEQ ID NO 10
<211> LENGTH: 18
<212> TYPE: DNA
<213> ORGANISM: Homo sapiens

<400> SEQUENCE: 10
gggttttgcg agagcgcg                                                      18

<210> SEQ ID NO 11
<211> LENGTH: 19
<212> TYPE: DNA
<213> ORGANISM: Homo sapiens

<400> SEQUENCE: 11
aaaccgcgca ataaaaacc                                                     19

<210> SEQ ID NO 12
<211> LENGTH: 15
<212> TYPE: DNA
<213> ORGANISM: Homo sapiens

<400> SEQUENCE: 12
cgcgaaccga acgaa                                                         15

<210> SEQ ID NO 13
<211> LENGTH: 20
<212> TYPE: DNA
<213> ORGANISM: Homo sapiens

<400> SEQUENCE: 13
gtgttaacgc gttgcgtatc                                                    20
```

<210> SEQ ID NO 14
<211> LENGTH: 21
<212> TYPE: DNA
<213> ORGANISM: Homo sapiens

<400> SEQUENCE: 14
aaccccgcga actaaaaacg a                                              21

<210> SEQ ID NO 15
<211> LENGTH: 18
<212> TYPE: DNA
<213> ORGANISM: Homo sapiens

<400> SEQUENCE: 15
aaatacgggt attttcgc                                                  18

<210> SEQ ID NO 16
<211> LENGTH: 36
<212> TYPE: DNA
<213> ORGANISM: Homo sapiens

<400> SEQUENCE: 16
gctcttcgtg gtgtggtgga ccacaacgac gacgac                              36

<210> SEQ ID NO 17
<211> LENGTH: 17
<212> TYPE: DNA
<213> ORGANISM: Homo sapiens

<400> SEQUENCE: 17
acgggtattt tcgcgtg                                                   17

<210> SEQ ID NO 18
<211> LENGTH: 17
<212> TYPE: DNA
<213> ORGANISM: Homo sapiens

<400> SEQUENCE: 18
ttcgtggtgt ggtggac                                                   17

<210> SEQ ID NO 19
<211> LENGTH: 45
<212> TYPE: DNA
<213> ORGANISM: Homo sapiens

<400> SEQUENCE: 19
ctgtgtgctc ttcgtgtgtg gtgtaaggtt ttttcggtta gttgc                    45

<210> SEQ ID NO 20
<211> LENGTH: 17
<212> TYPE: DNA
<213> ORGANISM: Homo sapiens
<220> FEATURE:
<221> NAME/KEY: Locked
<222> LOCATION: (11)..(11)
<223> OTHER INFORMATION: position 11 "G" is a locked nucleic acid
<220> FEATURE:
<221> NAME/KEY: Locked
<222> LOCATION: (11)..(11)
<223> OTHER INFORMATION: position 11 "G" is a  LNA (locked nucleic acid)
      nucleotide.

<400> SEQUENCE: 20
taaaatcccc gaaatcg                                                   17

```
<210> SEQ ID NO 21
<211> LENGTH: 22
<212> TYPE: DNA
<213> ORGANISM: Homo sapiens

<400> SEQUENCE: 21
tcttcgtgtg tggtgtaagg tt                                              22

<210> SEQ ID NO 22
<211> LENGTH: 19
<212> TYPE: DNA
<213> ORGANISM: Homo sapiens

<400> SEQUENCE: 22
gccctaaaat ccccgaaat                                                  19

<210> SEQ ID NO 23
<211> LENGTH: 21
<212> TYPE: DNA
<213> ORGANISM: Homo sapiens

<400> SEQUENCE: 23
tcggttagtt gcgcggcgat t                                               21

<210> SEQ ID NO 24
<211> LENGTH: 16
<212> TYPE: DNA
<213> ORGANISM: Homo sapiens

<400> SEQUENCE: 24
ctgcatgggc ggcatg                                                     16

<210> SEQ ID NO 25
<211> LENGTH: 19
<212> TYPE: DNA
<213> ORGANISM: Homo sapiens

<400> SEQUENCE: 25
tgaggatggg cctccggtt                                                  19

<210> SEQ ID NO 26
<211> LENGTH: 15
<212> TYPE: DNA
<213> ORGANISM: Homo sapiens

<400> SEQUENCE: 26
tgatggtgag gatgg                                                      15

<210> SEQ ID NO 27
<211> LENGTH: 7
<212> TYPE: DNA
<213> ORGANISM: Homo sapiens
<220> FEATURE:
<221> NAME/KEY: Locked
<222> LOCATION: (1)..(7)
<223> OTHER INFORMATION: positions 1-7 are LNA(locked nucleic acid)
      nucleotides.

<400> SEQUENCE: 27 ggaggcc                                                                7

<210> SEQ ID NO 28
<211> LENGTH: 12
<212> TYPE: DNA
```

```
<213> ORGANISM: Homo sapiens
<220> FEATURE:
<221> NAME/KEY: locked
<222> LOCATION: (5)..(5)
<223> OTHER INFORMATION: position 5 is a LNA (locked nucleic acid)
      nucleotide.
<220> FEATURE:
<221> NAME/KEY: locked
<222> LOCATION: (7)..(8)
<223> OTHER INFORMATION: position 7-8 are LNA (locked nucleic acid)
      nucleotides.

<400> SEQUENCE: 28
accggagtcc ca                                                              12

<210> SEQ ID NO 29
<211> LENGTH: 42
<212> TYPE: DNA
<213> ORGANISM: Homo sapiens

<400> SEQUENCE: 29
aaggcttccc cggccagctg cgcggcgact ccggggactc ca                             42
```